United States Patent
Baldino et al.

(10) Patent No.: US 9,073,903 B2
(45) Date of Patent: Jul. 7, 2015

(54) IMIDAZOLE-2,4-DIONE INHIBITORS OF CASEIN KINASE 1

(75) Inventors: Carmen M. Baldino, Woburn, MA (US); Justin L. Caserta, Billerica, MA (US); Chee-Seng Lee, Somerville, MA (US); Robert B. Nicewonger, Tyngsboro, MA (US)

(73) Assignee: Jasco Pharmaceuticals, LLC, Woburn, MA (US)

( * ) Notice: Subject to any disclaimer, the term of this patent is extended or adjusted under 35 U.S.C. 154(b) by 263 days.

(21) Appl. No.: 13/577,535

(22) PCT Filed: Feb. 17, 2011

(86) PCT No.: PCT/US2011/025246
§ 371 (c)(1),
(2), (4) Date: Aug. 23, 2012

(87) PCT Pub. No.: WO2011/103289
PCT Pub. Date: Aug. 25, 2011

(65) Prior Publication Data
US 2012/0316155 A1     Dec. 13, 2012

Related U.S. Application Data

(60) Provisional application No. 61/305,326, filed on Feb. 17, 2010.

(51) Int. Cl.
| | |
|---|---|
| A61K 31/506 | (2006.01) |
| A61K 31/497 | (2006.01) |
| A61K 31/5377 | (2006.01) |
| A61K 31/551 | (2006.01) |
| C07D 403/06 | (2006.01) |
| C07D 403/14 | (2006.01) |
| C07D 401/14 | (2006.01) |
| C07D 413/14 | (2006.01) |
| C07D 409/14 | (2006.01) |
| C07D 405/14 | (2006.01) |

(52) U.S. Cl.
CPC ............ *C07D 401/14* (2013.01); *C07D 403/14* (2013.01); *C07D 405/14* (2013.01); *C07D 413/14* (2013.01)

(58) Field of Classification Search
CPC .. C07D 403/06; C07D 403/14; C07D 401/14; C07D 413/14; C07D 409/14; C07D 405/14; A61K 31/506; A61K 31/497; A61K 31/5377; A61K 31/551
USPC ......... 514/218, 252.18, 252.19, 235.8, 230.8, 514/275; 544/295, 331, 332, 122, 121, 296; 540/575
See application file for complete search history.

(56) References Cited

U.S. PATENT DOCUMENTS

| | | | | |
|---|---|---|---|---|
| 8,173,808 | B2 * | 5/2012 | Ashwell et al. | ............... 544/331 |
| 8,563,539 | B2 * | 10/2013 | Baldino et al. | ............. 514/210.2 |
| 8,609,688 | B2 * | 12/2013 | Ashwell et al. | ............... 514/303 |
| 8,815,854 | B2 * | 8/2014 | Ashwell et al. | ............. 514/234.2 |

FOREIGN PATENT DOCUMENTS

| | | |
|---|---|---|
| CA | 1323629 C | 10/1993 |
| JP | 2003-081970 A | 3/2003 |
| JP | 2003-081971 A | 3/2003 |

OTHER PUBLICATIONS

Thenmozhiyal, J. C. et al, "Anticonvulsant Activity of Phenylmethylenehydantoins: A Structure-Activity Relationship Study", *J. Med. Chem.*, 47(6):1524-1535 (American Chemical Society, USA, 2004).
International Search Report of the International Searching Authority from parent PCT application PCT/US2011/025246 dated Nov. 30, 2011.
International Preliminary Report on Patentability and Written Opinion of the International Searching Authority from parent PCT application PCT/US2011/025246 dated Aug. 21, 2012.

* cited by examiner

*Primary Examiner* — James O Wilson
*Assistant Examiner* — Ebenezer O Sackey
(74) *Attorney, Agent, or Firm* — Dana M. Gordon; Foley Hoag LLP

(57) ABSTRACT

Disclosed are compounds, pharmaceutical compositions containing those compounds, and uses of the compounds and compositions as modulators of casein kinase 1 (e.g., CK1γ), the TGFβ pathway and/or the Wnt pathway. Uses are also disclosed for the treatment or prevention of a range of therapeutic indications due at least in part to aberrant physiological activity of casein kinase 1 (e.g., CK1γ), the TGFβ pathway and/or the Wnt pathway.

30 Claims, 5 Drawing Sheets

IMIDAZOLE-2,4-DIONE INHIBITORS OF CASEIN KINASE 1

RELATED APPLICATIONS

This application is the U.S. national phase of International Patent Application No. PCT/US2011/025246, filed Feb. 17, 2011, which claims the benefit of priority to U.S. Provisional Patent Application Ser. No. 61/305,326, filed Feb. 17, 2010.

BACKGROUND

Casein kinase 1 (CK1) is a family of evolutionarily conserved serine/threonine kinases including seven known members in vertebrates (CK1α, -β, -γ1, -γ2, -γ3, -δ and -ε). The CK1s contain a typical kinase domain followed by a C-terminal tail region, which has been implicated in the regulation of CK1 localization, substrate selectivity and kinase activity. Myriad proteins have been found to be phosphorylated by CK1s, which are involved in a wide range of cellular functions including vesicular trafficking, DNA damage repair, cell cycle progression, cytokinesis and circadian rhythms (reviewed by Gross and Anderson (1998); Vielhaber and Virshup (2001); Knippschild et al. (2005)). Moreover, CK1 family members (-α, -δ/ε and -γ) modulate the activities of major signaling pathways (for example, Wnt and Shh) through several mechanisms (Peters et al., 1999; Liu et al., 2002; Price and Kalderon, 2002; Davidson et al., 2005; Zeng et al., 2005 and reviewed by Price (2006)).

In mammals seven CK1 isoforms, namely CK1α, β, $\gamma_{1-3}$, δ and ε, and several splice variants have been described. They all contain a highly conserved kinase domain, a short N-terminal domain of 6 to 76 amino acids and a highly variable C-terminal domain of 24 to more than 200 amino acids. The constitutive phosphotransferase activity of CK1 isoforms is tightly controlled by several mechanisms. For example, the closely related isoforms CK1δ and ε, which share a 98% identity at the amino acid level in their catalytic domain, are regulated by autophosphorylation, dephosphorylation and proteolytic cleavage. Members of the CK1 family are found in the nucleus, the cytoplasm and in the plasma membrane. By phosphorylating many different substrates bearing either a canonical or non-canonical consensus sequence they modulate the activity of key regulator proteins involved in many cellular processes such as cell differentiation, cell proliferation, apoptosis, circadian rhythm, chromosome segregation, and vesicle transport.

SUMMARY

One aspect of the present invention relates to compounds that inhibit casein kinase 1. For example, one embodiment relates to a compound of formula 1:

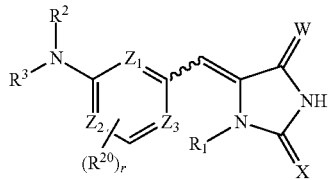

or a pharmaceutically acceptable salt thereof, wherein independently for each occurrence:
W and X are independently oxygen or sulfur;
$Z^1$, $Z^2$ and $Z^3$ are independently C—$R^{21}$ or N, provided that at least one of $Z^1$ and $Z^2$ is N;

$R^1$ is selected from the group consisting of hydrogen, alkyl, alkenyl, alkynyl, aralkyl, heteroaralkyl, —$COR^6$, and —C(O)$OR^6$;

$R^2$ is selected from the group consisting of alkyl, alkenyl, alkynyl, aryl, heteroaryl, heterocyclyl, aralkyl, heteroaralkyl, heterocyclylalkyl, —[C($R^4$)$_2$]$_p$—$R^5$, —$COR^6$, —C(O)$OR^6$, —SO$_2$($R^6$), —C(O)N($R^6$)($R^7$), —SO$_2$N($R^6$)($R^7$), —P(O)(O$R^6$)(O$R^7$);

$R^3$ is selected from the group consisting of hydrogen, alkyl, alkenyl, alkynyl, aryl, heteroaryl, heterocyclyl, aralkyl, heteroaralkyl, heterocyclylalkyl, —[C($R^4$)$_2$]$_p$—$R^5$, —$COR^6$, —C(O)$OR^6$, —SO$_2$($R^6$), —C(O)N($R^6$)($R^7$), —SO$_2$N($R^6$)($R^7$), —P(O)(O$R^6$)(O$R^7$); or $R^2$ and $R^3$ are joined together to form an optionally substituted heterocyclic ring;

$R^4$ is selected from the group consisting of hydrogen, alkyl, alkenyl, alkynyl, aryl, heterocyclylalkyl, aralkyl, heteroaryl, heteroaralkyl, halo, hydroxy, alkoxy, hydroxyalkyl, and alkoxyalkyl;

$R^5$ is selected from the group consisting of aryl, heteroaryl, heterocyclyl, —N($R^8$)($R^9$), —N($R^8$)$COR^9$, —N($R^8$)C(O)$OR^9$, —N($R^8$)SO$_2$($R^9$), —CON($R^8$)($R^9$), —OC(O)N($R^8$)($R^9$), —SO$_2$N($R^8$)($R^9$), —OC(O)$OR^8$, —COO$R^9$, —C(O)N(OH)($R^8$), —OS(O)$_2$$OR^8$, —S(O)$_2$$OR^8$, —S(O)$_2$$R^8$, —$OR^8$, —$COR^8$, —OP(O)(O$R^8$)(O$R^8$), —P(O)(O$R^8$)(O$R^8$) and —N($R^8$)P(O)(O$R^9$)(O$R^9$);

p is 1, 2, 3, 4, 5, or 6;

$R^6$ is selected from the group consisting of hydrogen, alkyl, alkenyl, alkynyl, aryl, heteroaryl, heterocyclyl, aralkyl, heteroaralkyl, and heterocyclylalkyl;

$R^7$ is selected from the group consisting of hydrogen, alkyl, alkenyl, alkynyl, aryl, heteroaryl, heterocyclyl, aralkyl, heteroaralkyl, and heterocyclylalkyl;

$R^8$ is selected from the group consisting of hydrogen, alkyl, alkenyl, alkynyl, aryl, heteroaryl, heterocyclyl, aralkyl, heteroaralkyl, and heterocyclylalkyl;

$R^9$ is selected from the group consisting of hydrogen, alkyl, alkenyl, alkynyl, aryl, heteroaryl, heterocyclyl, aralkyl, heteroaralkyl, and heterocyclylalkyl; or $R^8$ and $R^9$ are joined together to form a heterocyclic ring;

$R^{20}$ is selected from the group consisting of alkyl, alkenyl, alkynyl, aryl, heteroaryl, heterocyclyl, aralkyl, heteroaralkyl, heterocyclylalkyl, halo, haloalkyl, trifluoromethyl, fluoroalkyl, perfluoroalkyl, thio, cyano, hydroxy, methoxy, alkoxy, phenoxy, aryloxy, heteroaryloxy, carboxyl, alkoxycarbonyl, acyl, nitro, amino, alkylamino, arylamino, heteroarylamino, amido, acylamino, sulfate, sulfonate, sulfonyl, sulfoxido, sulfonamido, sulfamoyl, —[C($R^4$)$_2$]$_p$—$R^5$, $NR^{14}R^{15}$, $OR^{16}$, O—[C($R^4$)$_2$]$_p$—$R^5$, $NR^{14}$—[C($R^4$)$_2$]$_p$—$R^5$ and $SR^{16}$;

$R^{21}$ is selected from the group consisting of hydrogen, alkyl, alkenyl, alkynyl, aryl, heteroaryl, heterocyclyl, aralkyl, heteroaralkyl, heterocyclylalkyl, halo, haloalkyl, thio, cyano, carboxyl, alkoxycarbonyl, acyl, nitro, amino, amido, acylamino, sulfate, sulfonate, sulfonyl, sulfoxido, sulfonamido, sulfamoyl, $NR^{14}R^{15}$, $OR^{16}$, and $SR^{16}$;

$R^{14}$ and $R^{15}$ are each independently selected from the group consisting of hydrogen, alkyl, alkenyl, alkynyl, aryl, heteroaryl, heterocyclyl, aralkyl, heteroaralkyl, heterocyclylalkyl, —[C($R^4$)$_2$]$_p$—$R^5$, —$COR^6$, —C(O)$OR^6$, —SO$_2$($R^6$), —C(O)N($R^6$)($R^7$), —SO$_2$N($R^6$)($R^7$), and —P(O)(O$R^6$)(O$R^7$); or $R^{14}$ and $R^{15}$ are joined together to form an optionally substituted heterocyclic ring;

$R^{16}$ is selected from the group consisting of hydrogen, alkyl, alkenyl, alkynyl, aryl, heteroaryl, heterocyclyl, aralkyl, heteroaralkyl, heterocyclylalkyl, —[C($R^4$)$_2$]$_p$—$R^5$, —$COR^6$, and —C(O)N($R^6$)($R^7$); and r is 0 or 1;

wherein any one of the aforementioned alkyl, alkenyl, alkynyl, aryl, heteroaryl, heterocyclyl, aralkyl, heteroaralkyl, and heterocyclylalkyl may be optionally substituted.

Another embodiment relates to a compound of formula 2:

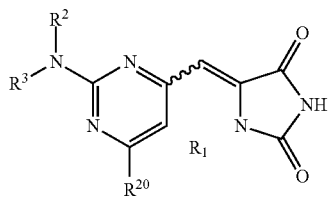

or a pharmaceutically acceptable salt thereof, wherein independently for each occurrence:

$R^1$ is selected from the group consisting of hydrogen, alkyl, alkenyl, alkynyl, aralkyl, heteroaralkyl, —$COR^6$, and —$C(O)OR^6$;

$R^2$ is selected from the group consisting of alkyl, alkenyl, alkynyl, aryl, heteroaryl, heterocyclyl, aralkyl, heteroaralkyl, heterocyclylalkyl, —$[C(R^4)_2]_p$—$R^5$, —$COR^6$, —$C(O)OR^6$, —$SO_2(R^6)$, —$C(O)N(R^6)(R^7)$, —$SO_2N(R^6)(R^7)$, —$P(O)(OR^6)(OR^7)$;

$R^3$ is selected from the group consisting of hydrogen, alkyl, alkenyl, alkynyl, aryl, heteroaryl, heterocyclyl, aralkyl, heteroaralkyl, heterocyclylalkyl, —$[C(R^4)_2]_p$—$R^5$, —$COR^6$, —$C(O)OR^6$, —$SO_2(R^6)$, —$C(O)N(R^6)(R^7)$, —$SO_2N(R^6)(R^7)$, —$P(O)(OR^6)(OR^7)$; or $R^2$ and $R^3$ are joined together to form an optionally substituted heterocyclic ring;

$R^4$ is selected from the group consisting of hydrogen, alkyl, alkenyl, alkynyl, aryl, heterocyclylalkyl, aralkyl, heteroaryl, heteroaralkyl, halo, hydroxy, alkoxy, hydroxyalkyl, and alkoxyalkyl;

$R^5$ is selected from the group consisting of aryl, heteroaryl, heterocyclyl, —$N(R^8)(R^9)$, —$N(R^8)COR^9$, —$N(R^8)C(O)OR^9$, —$N(R^8)SO_2(R^9)$, —$CON(R^8)(R^9)$, —$OC(O)N(R^8)(R^9)$, —$SO_2N(R^8)(R^9)$, —$OC(O)OR^8$, —$COOR^9$, —$C(O)N(OH)(R^8)$, —$OS(O)_2OR^8$, —$S(O)_2OR^8$, —$S(O)_2R^8$, —$OR^8$, —$COR^8$, —$OP(O)(OR^8)(OR^8)$, —$P(O)(OR^8)(OR^8)$ and —$N(R^8)P(O)(OR^9)(OR^9)$;

p is 1, 2, 3, 4, 5, or 6;

$R^6$ is selected from the group consisting of hydrogen, alkyl, alkenyl, alkynyl, aryl, heteroaryl, heterocyclyl, aralkyl, heteroaralkyl, and heterocyclylalkyl;

$R^7$ is selected from the group consisting of hydrogen, alkyl, alkenyl, alkynyl, heteroaryl, heterocyclyl, aralkyl, heteroaralkyl, and heterocyclylalkyl;

$R^8$ is selected from the group consisting of hydrogen, alkyl, alkenyl, alkynyl, aryl, heteroaryl, heterocyclyl, aralkyl, heteroaralkyl, and heterocyclylalkyl;

$R^9$ is selected from the group consisting of hydrogen, alkyl, alkenyl, alkynyl, aryl, heteroaryl, heterocyclyl, aralkyl, heteroaralkyl, and heterocyclylalkyl; or $R^8$ and $R^9$ are joined together to form a heterocyclic ring; and $R^{20}$ is selected from the group consisting of hydrogen, alkyl, alkenyl, alkynyl, aryl, heteroaryl, heterocyclyl, aralkyl, heteroaralkyl, heterocyclylalkyl, halo, haloalkyl, trifluoromethyl, fluoroalkyl, perfluoroalkyl, thio, cyano, hydroxy, methoxy, alkoxy, phenoxy, aryloxy, heteroaryloxy, carboxyl, alkoxycarbonyl, acyl, nitro, amino, alkylamino, arylamino, heteroarylamino, amido, acylamino, sulfate, sulfonate, sulfonyl, sulfoxido, sulfonamido, sulfamoyl, —$[C(R^4)_2]_p$—$R^5$, $NR^{14}R^{15}$, $OR^{16}$, O—$[C(R^4)_2]_p$—$R^5$, $NR^{14}$—$[C(R^4)_2]_p$—$R^5$ and $SR^{16}$;

wherein any one of the aforementioned alkyl, alkenyl, alkynyl, aryl, heteroaryl, heterocyclyl, aralkyl, heteroaralkyl, and heterocyclylalkyl may be optionally substituted.

Another embodiment relates to a pharmaceutical composition, comprising at least one pharmaceutically acceptable excipient; and any one of the aforementioned compounds.

Another embodiment relates to a method of inhibiting CK1 (e.g., CK1γ, CK1γ1, CK1γ2, or CK1γ3) activity, comprising contacting CK1 (e.g., CK1γ, CK1γ1, CK1γ2, or CK1γ3) with any one of the aforementioned compounds or pharmaceutical compositions.

Another embodiment relates to treating or preventing a condition associated with aberrant CK1 (e.g., CK1γ) activity, comprising the step of administering to a mammal in need thereof a therapeutically effective amount of any one of the aforementioned compounds or compositions.

Another embodiment relates to a method of treating cancer, comprising administering to a mammal in need thereof a therapeutically effective amount of any one of the aforementioned compounds or compositions.

Another embodiment relates to a method of treating Alzheimer's disease, comprising administering to a mammal in need thereof a therapeutically effective amount of any one of the aforementioned compounds or compositions.

Another embodiment relates to a method of treating a Wnt dependent disease, comprising administering to a mammal in need thereof a therapeutically effective amount of any one of the aforementioned compounds or compositions.

Another embodiment relates to a method of treating a TGFβ dependent disease, comprising administering to a mammal in need thereof a therapeutically effective amount of any one of the aforementioned compounds or compositions.

Another embodiment relates to a method of treating or preventing inflammation, inflammatory diseases (e.g., osteoarthritis and rheumatoid arthritis), neurological conditions (e.g., Alzheimer's disease) and neurodegeneration, comprising administering to a mammal in need thereof a therapeutically effective amount of any one of the aforementioned compounds or compositions.

Another embodiment relates to a method of treating or preventing bone-related diseases and conditions, including osteoporosis and bone formation, or facilitating bone restoration, comprising administering to a mammal in need thereof a therapeutically effective amount of any one of the aforementioned compounds or compositions.

Another embodiment relates to a method of treating or preventing hypoglycemia, metabolic syndrome and diabetes, comprising administering to a mammal in need thereof a therapeutically effective amount of any one of the aforementioned compounds or compositions.

Another embodiment relates to a method of influencing apoptosis (e.g., increasing the rate of apoptosis in cancerous cells), comprising administering to a mammal in need thereof a therapeutically effective amount of any one of the aforementioned compounds or compositions.

Another embodiment relates to a method of treating or preventing aberrant embryonic development, comprising administering to a mammal in need thereof a therapeutically effective amount of any one of the aforementioned compounds or compositions.

DETAILED DESCRIPTION

Definitions

Figure 1:
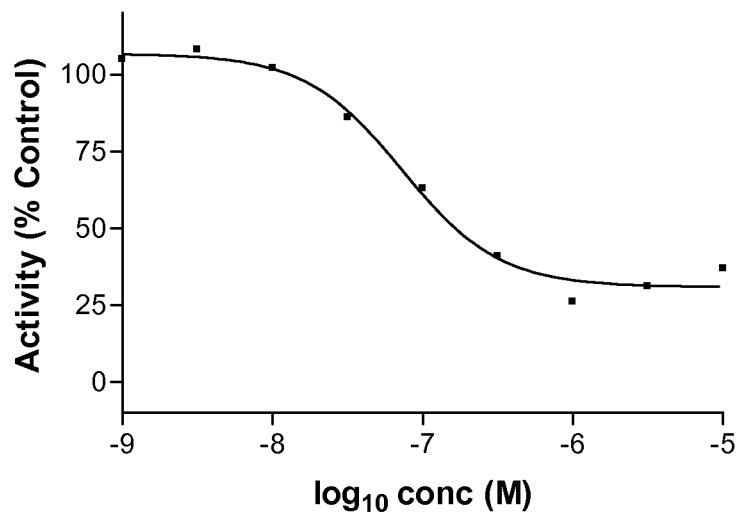
FIG. 1 depicts the relative activity of CK1γ1(h) as a function of the concentration of compound 5114.

The definitions of terms used herein are meant to incorporate the present state-of-the-art definitions recognized for each term in the chemical and pharmaceutical fields. Where appropriate, illustration is provided. The definitions apply to the terms as they are used throughout this specification, unless otherwise limited in specific instances, either individually or as part of a larger group.

Where stereochemistry is not specifically indicated, all stereoisomers of the inventive compounds are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

As used herein, the term "isolated" in connection with a compound of the present invention means the compound is not in a cell or organism and the compound is separated from some or all of the components that typically accompany it in nature.

As used herein, the term "pure" in connection with an isolated sample of a compound of the present invention means the isolated sample contains at least 60% by weight of the compound. Preferably, the isolated sample contains at least 70% by weight of the compound. More preferably, the isolated sample contains at least 80% by weight of the compound. Even more preferably, the isolated sample contains at least 90% by weight of the compound. Most preferably, the isolated sample contains at least 95% by weight of the compound. The purity of an isolated sample of a compound of the present invention may be assessed by a number of methods or a combination of them; e.g., thin-layer, preparative or flash chromatography, mass spectrometry, HPLC, NMR analysis, and the like.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, piperonyl, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "optionally substituted" refers to a chemical group, such as alkyl, cycloalkyl aryl, and the like, wherein one or more hydrogen may be replaced with a with a substituent as described herein, including but not limited to halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

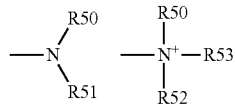

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

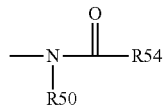

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

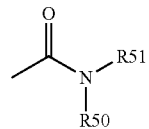

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

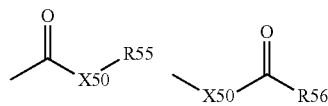

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

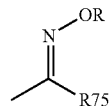

wherein R75 is hydrogen, alkyl, cycloalkyl, alkenyl, alkynyl, aryl, aralkyl, or —(CH$_2$)$_m$—R61. The moiety is an "oxime"

when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O—(CH$_2$)$_m$—R61, where m and R61 are described above.

The term "sulfonate" is art recognized and refers to a moiety that may be represented by the general formula:

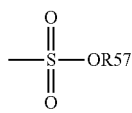

in which R57 is an electron pair, hydrogen, alkyl, cycloalkyl, or aryl.

The term "sulfate" is art recognized and includes a moiety that may be represented by the general formula:

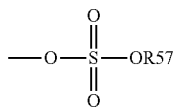

in which R57 is as defined above.

The term "sulfonamido" is art recognized and includes a moiety that may be represented by the general formula:

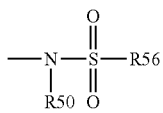

in which R50 and R56 are as defined above.

The term "sulfamoyl" is art-recognized and refers to a moiety that may be represented by the general formula:

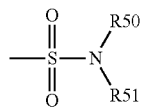

in which R50 and R51 are as defined above.

The term "sulfonyl" is art-recognized and refers to a moiety that may be represented by the general formula:

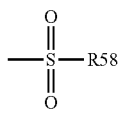

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

The term "phosphoryl" is art-recognized and may in general be represented by the formula:

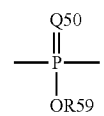

wherein Q50 represents S or O, and R59 represents hydrogen, a lower alkyl or an aryl. When used to substitute, e.g., an alkyl, the phosphoryl group of the phosphorylalkyl may be represented by the general formulas:

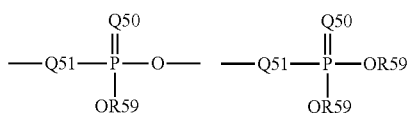

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

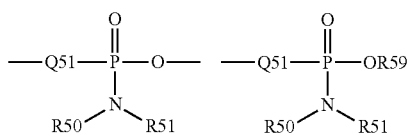

wherein Q51, R50, R51 and R59 are as defined above.

The term "phosphonamidite" is art-recognized and may be represented in the general formulas:

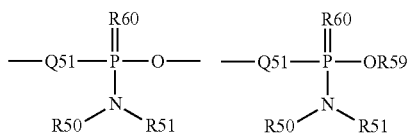

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. Examples of nitrogen protecting groups include an amide (—NRC(=O)R) or a urethane (—NRC(=O)OR), for example, as: a methyl amide (—NHC(=O)CH$_3$); a benzyloxy amide (—NHC(=O)OCH$_2$C$_6$H$_5$NHCbz); as a t-butoxy amide (—NHC=(=O)OC(CH$_3$)$_3$, —NHBoc); a 2-biphenyl-2-propoxy amide (—NHC(=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical. The field of protecting group chemistry has been reviewed (Greene, T. W.; Wuts, P. G. M. *Protective Groups in Organic Synthesis, 2$^{nd}$* ed.; Wiley: New York, 1991). Protected forms of the inventive compounds are included within the scope of this invention.

For purposes of this invention, the chemical elements are identified in accordance with the Periodic Table of the Elements, CAS version, *Handbook of Chemistry and Physics*, 67th Ed., 1986-87, inside cover.

The term "pharmaceutically acceptable salt" or "salt" refers to a salt of one or more compounds. Suitable pharmaceutically acceptable salts of compounds include acid addition salts, such as those formed with mineral acids such as hydrochloric acid and hydrobromic acid, and also those formed with organic acids such as maleic acid. For example, acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like.

Where the compounds carry one or more acidic moieties, pharmaceutically acceptable salts may be formed by treatment of a solution of the compound with a solution of a pharmaceutically acceptable base. Suitable bases for forming pharmaceutically acceptable salts with acidic functional groups include, but are not limited to, hydroxides and carbonates of alkali metals such as sodium, potassium, and lithium; alkaline earth metal such as calcium and magnesium; and other metals, such as aluminum and zinc. Suitable bases also include ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di alkyl-N-(hydroxy alkyl)-amines, such as N,N-dimethyl-N-(2-hydroxyethyl) amine, or tri-(2-hydroxyethyl)amine; N-methyl-D-glucamine; and amino acids such as arginine, lysine, and the like.

Certain compounds of the invention and their salts may exist in more than one crystalline form (i.e., polymorph); the present invention includes each of the crystal forms and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures thereof. The enantiomers may be resolved by methods known to those skilled in the art; for example, enantiomers may be resolved by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example, via enzymatic esterification; or gas-liquid or liquid chromatography in a chiral environment, for example, on a chiral support; suitable include chiral supports (e.g., silica with a bound chiral ligand) or in the presence of a chiral solvent. Where the desired enantiomer is converted into another chemical entity by one of the separation procedures described above, a further step may be used to liberate the desired purified enantiomer. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art (for example, chromatography or crystallization) and the individual enantiomers may be separated as described above. The present invention includes the various diastereoisomers of compounds of the invention, and mixtures thereof. Compounds of the invention may exist in different tautomeric forms or as different geometric isomers, and the present invention includes each tautomer and/or geometric isomer of compounds of the invention, and mixtures thereof. For example, any olefins present in the compounds may exist as either the E- or Z-geometric isomers, or a mixture thereof unless stated otherwise. Compounds of the invention may exist in zwitterionic form. The present invention includes each zwitterionic form of compounds of the invention, and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs release an amine of a compound of the invention wherein the free hydrogen of an amine or alcohol is replaced by $(C_1-C_6)$alkanoyloxymethyl, 1-(($C_1-C_6$)alkanoyloxy)ethyl, 1-methyl-1-($C_1-C_6$)alkanoyloxy)ethyl, ($C_1-C_6$)alkoxycarbonyl-oxymethyl, N—($C_1-C_6$)alkoxycarbonylamino-methyl, succinoyl, ($C_1-C_6$)alkanoyl, α-amino($C_1-C_4$)alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O($C_1-C_6$)alkyl)$_2$ or glycosyl (the radical resulting from detachment of the hydroxyl of the hemiacetal of a carbohydrate).

Other exemplary pro-drugs upon cleavage release a corresponding free acid, and such hydrolyzable ester-forming residues of the compounds of this invention include but are not limited to carboxylic acid substituents (e.g., —(CH$_2$)C(O) OH or a moiety that contains a carboxylic acid) wherein the free hydrogen is replaced by ($C_1-C_4$)alkyl, ($C_2-C_{12}$)alkanoyloxymethyl, ($C_4-C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1-C_2$)alkylamino($C_2-C_3$)alkyl (such as β-dimethylaminoethyl), carbamoyl-($C_1-C_2$)alkyl, N,N-di($C_1-C_2$)-alkylcarbamoyl-($C_1-C_2$)alkyl and piperidino-, pyrrolidino- or morpholino($C_2-C_3$) alkyl.

The term "subject" as used herein, refers to an animal, typically a mammal or a human, that will be or has been the object of treatment, observation, and/or experiment. When the term is used in conjunction with administration of a compound or drug, then the subject has been the object of treatment, observation, and/or administration of the compound or drug.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "therapeutically effective amount" as used herein, means that amount of active compound or pharmaceutical agent that elicits a biological or medicinal response in a cell culture, tissue system, animal, or human that is being sought by a researcher, veterinarian, clinician, or physician, which includes alleviation of the symptoms of the disease, condition, or disorder being treated.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

Compounds

One embodiment of the invention relates to a compound of formula 1:

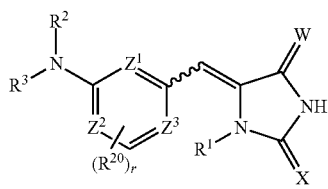

1 or a pharmaceutically acceptable salt thereof, wherein independently for each occurrence:

W and X are independently oxygen or sulfur;

$Z^1$, $Z^2$ and $Z^3$ are independently $C-R^{21}$ or N, provided that at least one of $Z^1$ and $Z^2$ is N;

$R^1$ is selected from the group consisting of hydrogen, alkyl, alkenyl, alkynyl, aralkyl, heteroaralkyl, $-COR^6$, and $-C(O)OR^6$;

$R^2$ is selected from the group consisting of alkyl, alkenyl, alkynyl, aryl, heteroaryl, heterocyclyl, aralkyl, heteroaralkyl, heterocyclylalkyl, $-[C(R^4)_2]_p-R^5$, $-COR^6$, $-C(O)OR^6$, $-SO_2(R^6)$, $-C(O)N(R^6)(R^7)$, $-SO_2N(R^6)(R^7)$, $-P(O)(OR^6)(OR^7)$;

$R^3$ is selected from the group consisting of hydrogen, alkyl, alkenyl, alkynyl, aryl, heteroaryl, heterocyclyl, aralkyl, heteroaralkyl, heterocyclylalkyl, $-[C(R^4)_2]_p-R^5$, $-COR^6$, $-C(O)OR^6$, $-SO_2(R^6)$, $-C(O)N(R^6)(R^7)$, $-SO_2N(R^6)(R^7)$, $-P(O)(OR^6)(OR^7)$; or $R^2$ and $R^3$ are joined together to form an optionally substituted heterocyclic ring;

$R^4$ is selected from the group consisting of hydrogen, alkyl, alkenyl, alkynyl, aryl, heterocyclylalkyl, aralkyl, heteroaryl, heteroaralkyl, halo, hydroxy, alkoxy, hydroxyalkyl, and alkoxyalkyl;

$R^5$ is selected from the group consisting of aryl, heteroaryl, heterocyclyl, $-N(R^8)(R^9)$, $-N(R^8)COR^9$, $-N(R^8)C(O)OR^9$, $-N(R^8)SO_2(R^9)$, $-CON(R^8)(R^9)$, $-OC(O)N(R^8)-(R^9)$, $-SO_2N(R^8)(R^9)$, $-OC(O)OR^8$, $-COOR^9$, $-C(O)N(OH)(R^8)$, $-OS(O)_2OR^8$, $-S(O)_2OR^8$, $-S(O)_2R^8$, $-COR^8$, $-OP(O)(OR^8)(OR^8)$, $-P(O)(OR^8)(OR^8)$ and $-N(R^8)P(O)(OR^9)(OR^9)$;

p is 1, 2, 3, 4, 5, or 6;

$R^6$ is selected from the group consisting of hydrogen, alkyl, alkenyl, alkynyl, aryl, heteroaryl, heterocyclyl, aralkyl, heteroaralkyl, and heterocyclylalkyl;

$R^7$ is selected from the group consisting of hydrogen, alkyl, alkenyl, alkynyl, aryl, heteroaryl, heterocyclyl, aralkyl, heteroaralkyl, and heterocyclylalkyl;

$R^8$ is selected from the group consisting of hydrogen, alkyl, alkenyl, alkynyl, aryl, heteroaryl, heterocyclyl, aralkyl, heteroaralkyl, and heterocyclylalkyl;

$R^9$ is selected from the group consisting of hydrogen, alkyl, alkenyl, alkynyl, aryl, heteroaryl, heterocyclyl, aralkyl, heteroaralkyl, and heterocyclylalkyl; or $R^8$ and $R^9$ are joined together to form a heterocyclic ring;

$R^{20}$ is selected from the group consisting of alkyl, alkenyl, alkynyl, aryl, heteroaryl, heterocyclyl, aralkyl, heteroaralkyl, heterocyclylalkyl, halo, haloalkyl, trifluoromethyl, fluoroalkyl, perfluoroalkyl, thio, cyano, hydroxy, methoxy, alkoxy, phenoxy, aryloxy, heteroaryloxy, carboxyl, alkoxycarbonyl, acyl, nitro, amino, alkylamino, arylamino, heteroarylamino, amido, acylamino, sulfate, sulfonate, sulfonyl, sulfoxido, sulfonamido, sulfamoyl, $-[C(R^4)_2]_p-R^5$, $NR^{14}R^{15}$, $-OR^{16}$, $O-[C(R^4)_2]_p-R^5$, $NR^{14}-[C(R^4)_2]_p-R^5$ and $SR^{16}$;

$R^{21}$ is selected from the group consisting of hydrogen, alkyl, alkenyl, alkynyl, aryl, heteroaryl, heterocyclyl, aralkyl, heteroaralkyl, heterocyclylalkyl, halo, haloalkyl, thio, cyano, carboxyl, alkoxycarbonyl, acyl, nitro, amino, amido, acylamino, sulfate, sulfonate, sulfonyl, sulfoxido, sulfonamido, sulfamoyl, $NR^{14}R^{15}$, $OR^{16}$, and $SR^{16}$;

$R^{14}$ and $R^{15}$ are each independently selected from the group consisting of hydrogen, alkyl, alkenyl, alkynyl, aryl, heteroaryl, heterocyclyl, aralkyl, heteroaralkyl, heterocyclylalkyl, $-[C(R^4)_2]_p-R^5$, $-COR^6$, $-C(O)OR^6$, $-SO_2(R^6)$, $-C(O)N(R^6)(R^7)$, $-SO_2N(R^6)(R^7)$, and $-P(O)(OR^6)(OR^7)$; or $R^{14}$ and $R^{15}$ are joined together to form an optionally substituted heterocyclic ring;

$R^{16}$ is selected from the group consisting of hydrogen, alkyl, alkenyl, alkynyl, aryl, heteroaryl, heterocyclyl, aralkyl, heteroaralkyl, heterocyclylalkyl, $-[C(R^4)_2]_p-R^5$, $-COR^6$, and $-C(O)N(R^6)(R^7)$; and r is 0 or 1;

wherein any one of the aforementioned alkyl, alkenyl, alkynyl, aryl, heteroaryl, heterocyclyl, aralkyl, heteroaralkyl, and heterocyclylalkyl may be optionally substituted.

In another embodiment, W and X are oxygen.

In another embodiment, $Z^1$ and $Z^2$ are nitrogen; and $Z^3$ is $C-R^{21}$.

In another embodiment, $Z^1$, $Z^2$ and $Z^3$ are nitrogen.

In another embodiment, $Z^1$ is nitrogen; and $Z^2$ and $Z^3$ are each $C-R^{21}$.

In another embodiment, $Z^2$ is nitrogen; and $Z^1$ and $Z^3$ are each $C-R^{21}$.

In another embodiment, $R^1$ is hydrogen, alkyl, or aralkyl.

In another embodiment, W and X are oxygen, $Z^1$ and $Z^2$ are each nitrogen, $Z^3$ is $C-R^{21}$, and $R^1$ is hydrogen, alkyl, or aralkyl.

In another embodiment, $R^1$ is hydrogen.

In another embodiment, $R^2$ and $R^3$ are joined together to form an optionally substituted heterocyclic ring.

In another embodiment, the optionally substituted heterocyclic ring is selected from the group consisting of piperazinyl, homopiperizinyl, pyrrolidinyl, piperidinyl, homopiperidinyl, morpholinyl, and quinolinyl.

In another embodiment, $R^2$ is selected from the group consisting of alkyl, alkenyl, alkynyl, aryl, heteroaryl, heterocyclyl, $-[C(R^4)_2]_p-R^5$, $-COR^6$, $-C(O)OR^6$, $-SO_2(R^6)$, $-C(O)N(R^6)(R^7)$, and $-SO_2N(R^6)(R^7)$, and $R^3$ is selected from the group consisting of hydrogen, alkyl, alkenyl, alkynyl, aryl, heteroaryl, heterocyclyl, $-[C(R^4)_2]_p-R^5$, $-COR^6$, $-C(O)OR^6$, $-SO_2(R^6)$, $-C(O)N(R^6)(R^7)$, and $-SO_2N(R^6)(R^7)$, wherein the alkyl, alkenyl, alkynyl, aryl, heteroaryl, and heterocyclyl may be optionally substituted.

In another embodiment, $R^2$ is $-[C(R^4)_2]_p-R^5$, and $R^3$ is selected from the group consisting of alkyl, alkenyl, alkynyl, aryl, heteroaryl, heterocyclyl, $-COR^6$, $-C(O)OR^6$, $-SO_2(R^6)$, $-C(O)N(R^6)(R^7)$, and $-SO_2N(R^6)(R^7)$, wherein the alkyl, alkenyl, alkynyl, aryl, heteroaryl, and heterocyclyl may be optionally substituted.

In another embodiment, $R^5$ is aryl or heteroaryl, each of which may be optionally substituted.

In another embodiment, $R^5$ is $-N(R^8)(R^9)$.

In another embodiment, $R^4$ is hydrogen.

In another embodiment, r is 0.

Another aspect of the invention relates to a compound of formula 2:

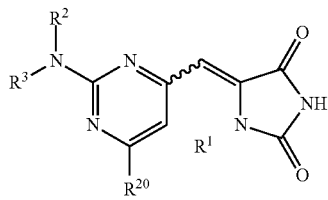

or a pharmaceutically acceptable salt thereof, wherein independently for each occurrence:

$R^1$ is selected from the group consisting of hydrogen, alkyl, alkenyl, alkynyl, aralkyl, heteroaralkyl, —$COR^6$, and —$C(O)OR^6$;

$R^2$ is selected from the group consisting of alkyl, alkenyl, alkynyl, aryl, heteroaryl, heterocyclyl, aralkyl, heteroaralkyl, heterocyclylalkyl, —$[C(R^4)_2]_p$—$R^5$, —$COR^6$, —$C(O)OR^6$, —$SO_2(R^6)$, —$C(O)N(R^6)(R^7)$, —$SO_2N(R^6)(R^7)$, —$P(O)(OR^6)(OR^7)$;

$R^3$ is selected from the group consisting of hydrogen, alkyl, alkenyl, alkynyl, aryl, heteroaryl, heterocyclyl, aralkyl, heteroaralkyl, heterocyclylalkyl, —$[C(R^4)_2]_p$—$R^5$, —$COR^6$, —$C(O)OR^6$, —$SO_2(R^6)$, —$C(O)N(R^6)(R^7)$, —$SO_2N(R^6)(R^7)$, —$P(O)(OR^6)(OR^7)$; or $R^2$ and $R^3$ are joined together to form an optionally substituted heterocyclic ring;

$R^4$ is selected from the group consisting of hydrogen, alkyl, alkenyl, alkynyl, aryl, heterocyclylalkyl, aralkyl, heteroaryl, heteroaralkyl, halo, hydroxy, alkoxy, hydroxyalkyl, and alkoxyalkyl;

$R^5$ is selected from the group consisting of aryl, heteroaryl, heterocyclyl, —$N(R^8)(R^9)$, —$N(R^8)COR^9$, —$N(R^8)C(O)OR^9$, —$N(R^8)SO_2(R^9)$, —$CON(R^8)(R^9)$, —$OC(O)N(R^8)$—$(R^9)$, —$SO_2N(R^8)(R^9)$, —$OC(O)OR^8$, —$COOR^9$, —$C(O)N(OH)(R^8)$, —$OS(O)_2OR^8$, —$S(O)_2OR^8$, —$S(O)_2R^8$, —$OR^8$, —$COR^8$, —$OP(O)(OR^8)(OR^8)$, —$P(O)(OR^8)(OR^8)$ and —$N(R^8)P(O)(OR^9)(OR^9)$;

p is 1, 2, 3, 4, 5, or 6;

$R^6$ is selected from the group consisting of hydrogen, alkyl, alkenyl, alkynyl, aryl, heteroaryl, heterocyclyl, aralkyl, heteroaralkyl, and heterocyclylalkyl;

$R^7$ is selected from the group consisting of hydrogen, alkyl, alkenyl, alkynyl, aryl, heteroaryl, heterocyclyl, aralkyl, heteroaralkyl, and heterocyclylalkyl;

$R^8$ is selected from the group consisting of hydrogen, alkyl, alkenyl, alkynyl, aryl, heteroaryl, heterocyclyl, aralkyl, heteroaralkyl, and heterocyclylalkyl;

$R^9$ is selected from the group consisting of hydrogen, alkyl, alkenyl, alkynyl, aryl, heteroaryl, heterocyclyl, aralkyl, heteroaralkyl, and heterocyclylalkyl; or $R^8$ and $R^9$ are joined together to form a heterocyclic ring; and $R^{20}$ is selected from the group consisting of hydrogen, alkyl, alkenyl, alkynyl, aryl, heteroaryl, heterocyclyl, aralkyl, heteroaralkyl, heterocyclylalkyl, halo, haloalkyl, trifluoromethyl, fluoroalkyl, perfluoroalkyl, thio, cyano, hydroxy, methoxy, alkoxy, phenoxy, aryloxy, heteroaryloxy, carboxyl, alkoxycarbonyl, acyl, nitro, amino, alkylamino, arylamino, heteroarylamino, amido, acylamino, sulfate, sulfonate, sulfonyl, sulfoxido, sulfonamido, sulfamoyl, —$[C(R^4)_2]_p$—$R^5$, $NR^{14}R^{15}$, $OR^{16}$, O—$[C(R^4)_2]_p$—$R^5$, $NR^{14}$—$[C(R^4)_2]_p$—$R^5$, and $SR^{16}$;

wherein any one of the aforementioned alkyl, alkenyl, alkynyl, aryl, heteroaryl, heterocyclyl, aralkyl, heteroaralkyl, and heterocyclylalkyl may be optionally substituted.

In another embodiment, $R^1$ is hydrogen, alkyl, or aralkyl.

In another embodiment, $R^1$ is hydrogen, methyl, or benzyl.

In another embodiment, $R^2$ and $R^3$ are joined together to form an optionally substituted heterocyclic ring.

In another embodiment, $R^2$ and $R^3$ are joined together to form an optionally substituted heterocyclic ring selected from the group consisting of:

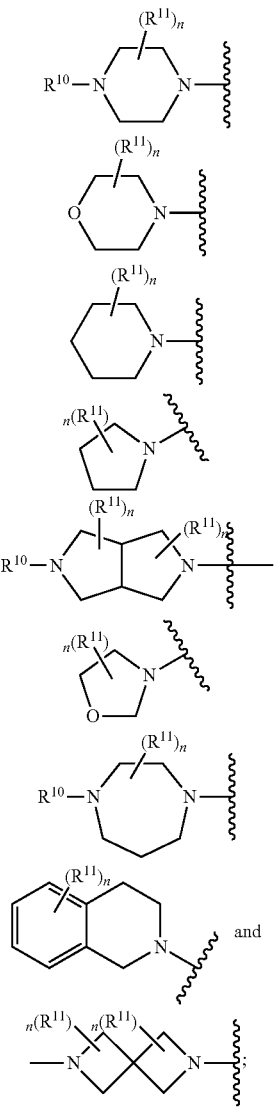

wherein, independently for each occurrence:

$R^{10}$ is selected from the group consisting of hydrogen, alkyl, alkenyl, alkynyl, aryl, heteroaryl, heterocyclyl, aralkyl, heteroaralkyl, heterocyclylalkyl, —$[C(R^4)_2]_p$—$R^5$, —$COR^6$, —$C(O)OR^6$, —$SO_2(R^6)$, —$C(O)N(R^6)(R^7)$, —$SO_2N(R^6)(R^7)$; and —$P(O)(OR^6)(OR^7)$;

$R^{11}$ is selected from the group consisting of alkyl, alkenyl, alkynyl, aryl, heteroaryl, heterocyclyl, halo, haloalkyl, thio, cyano, alkylthio, nitro, —$N(R^8)(R^9)$, —$N(R^8)COR^9$, —$N(R^8)C(O)OR^9$, —$N(R^8)SO_2(R^9)$, —$CON(R^8)(R^9)$, —$OC(O)N(R^8)$—$(R^9)$, —$SO_2N(R^8)(R^9)$, —$OC(O)OR^8$, —COOR$^9$, —C(O)N(OH)(R$^8$), —OS(O)$_2$OR$^8$, —S(O)$_2$OR$^8$, —S(O)$_2$R$^8$, —OR$^8$, —COR$^8$, —OP(O)(OR$^8$)(OR$^8$), —P(O)(OR$^8$)(OR$^8$), —N(R$^8$)P(O)(OR$^9$)(OR$^9$) and —[C(R$^4$)$_2$]$_p$—R$^5$;
and —[C(R$^4$)$_2$]$_p$—R$^5$; and
n is 0, 1, 2, or 3;
wherein any one of the aforementioned alkyl, alkenyl, alkynyl, aryl, heteroaryl, heterocyclyl, aralkyl, heteroaralkyl, and heterocyclylalkyl may be optionally substituted.

In another embodiment, R$^2$ and R$^3$ are joined together to form an optionally substituted heterocyclic ring of the formula:

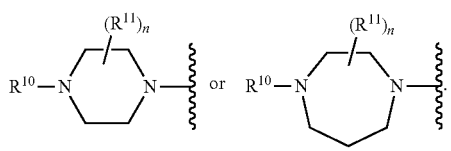

In another embodiment, wherein n is 0.

In another embodiment, R$^{10}$ is hydrogen, alkyl, aryl, heteroaryl, —COR$^6$, —C(O)OR$^6$, or —SO$_2$(R$^6$), or —[C(R$^4$)$_2$]$_p$—R$^5$.

In another embodiment, R$^2$ and R$^3$ are joined together to form an optionally substituted heterocyclic ring of the formula:

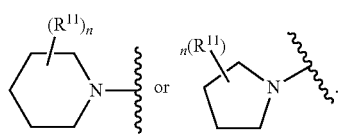

In another embodiment, n is 0 or 1.

In another embodiment, R$^{11}$ is alkyl, aryl, heteroaryl, heterocyclyl, —N(R$^8$)(R$^9$), —N(R$^8$)COR$^9$, —N(R$^8$)C(O)OR$^9$, —N(R$^8$)SO$_2$(R$^9$) and —[C(R$^4$)$_2$]$_p$—R$^5$.

In another embodiment, R$^{11}$ is —[C(R$^4$)$_2$]$_p$—R$^5$, wherein p is 1 or 2, R$^4$ is hydrogen, and R$^5$ is selected from the group consisting of aryl, heteroaryl, heterocyclyl, —N(R$^8$)(R$^9$), —N(R$^8$)COR$^9$, —N(R$^8$)C(O)OR$^9$, and —N(R$^8$)SO$_2$(R$^9$).

In another embodiment, R$^2$ and R$^3$ are each independently selected from the group consisting of alkyl, alkenyl, alkynyl, aryl, heteroaryl, heterocyclyl, —[C(R$^4$)$_2$]$_p$—R$^5$, —COR$^6$, —C(O)OR$^6$, —SO$_2$(R$^6$), —C(O)N(R$^6$)(R$^7$), and —SO$_2$N(R$^6$)(R$^7$), wherein the alkyl, alkenyl, alkynyl, aryl, heteroaryl, and heterocyclyl may be optionally substituted.

In another embodiment, R$^2$ is selected from the group consisting of alkyl, alkenyl, alkynyl, aryl, heteroaryl, heterocyclyl, —COR$^6$, —C(O)OR$^6$, —SO$_2$(R$^6$), —C(O)N(R$^6$)(R$^7$), and —SO$_2$N(R$^6$)(R$^7$); and R$^3$ is —[C(R$^4$)$_2$]$_p$—R$^5$.

In another embodiment, R$^2$ is optionally substituted alkyl.

In another embodiment, R$^3$ is aryl, heteroaryl, heterocyclyl, each of which may be optionally substituted.

In another embodiment, at least one of R$^2$ and R$^3$ is —[C(R$^4$)$_2$]$_p$—R$^5$.

In another embodiment, R$^4$ is hydrogen.

In another embodiment, R$^5$ is selected from the group consisting of aryl, heteroaryl, —N(R$^8$)(R$^9$), —N(R$^8$)COR$^9$, —N(R$^8$)C(O)OR$^9$, —N(R$^8$)SO$_2$(R$^9$), —CON(R$^8$)(R$^9$), —OC(O)N(R$^8$)—(R$^9$), —SO$_2$N(R$^8$)(R$^9$), —OC(O)OR$^8$, —COOR$^9$, —C(O)N(OH)(R$^8$), —OS(O)$_2$OR$^8$, —S(O)$_2$OR$^8$, —S(O)$_2$R$^8$, —OR$^8$, —COR$^8$, —OP(O)(OR$^8$)(OR$^8$), —P(O)(OR$^8$)(OR$^8$) and —N(R$^8$)P(O)(OR$^9$)(OR$^9$).

In another embodiment, R$^5$ is —N(R$^8$)(R$^9$).

In another embodiment, R$^5$ is aryl or heteroaryl.

In another embodiment, R$^{20}$ is hydrogen.

Another aspect of the invention relates to a compound, or a pharmaceutically acceptable salt thereof, selected from the group consisting of:

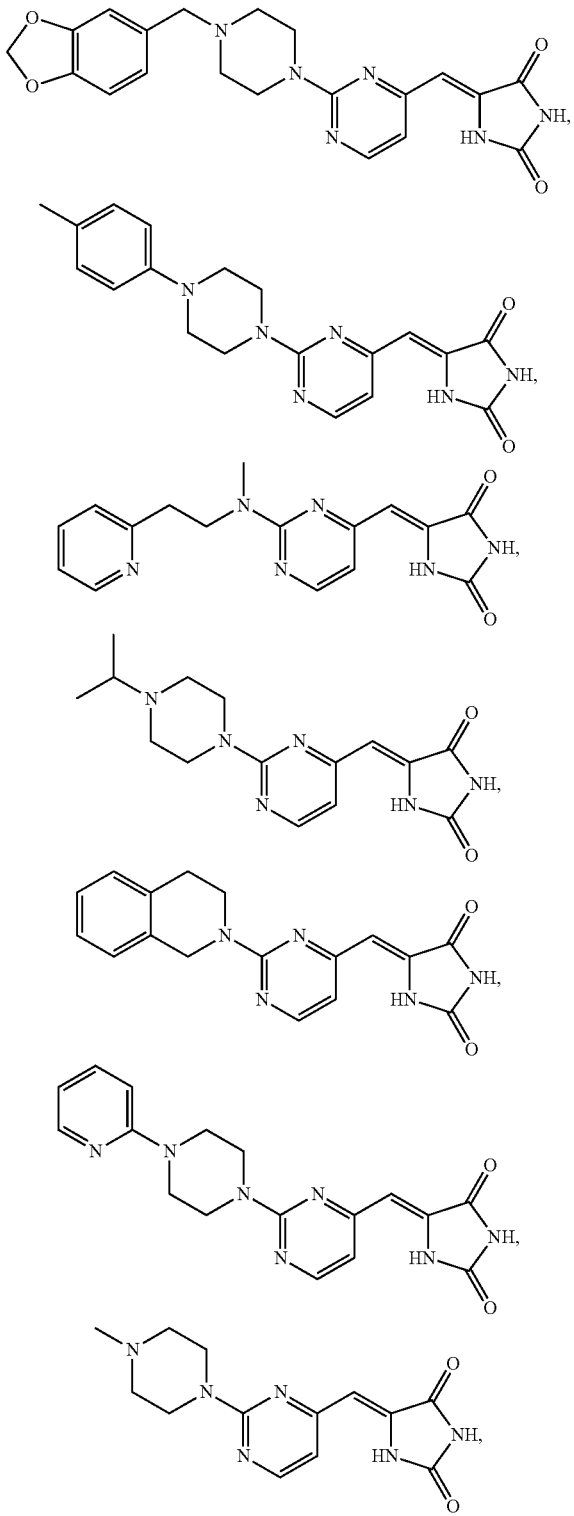

21
-continued
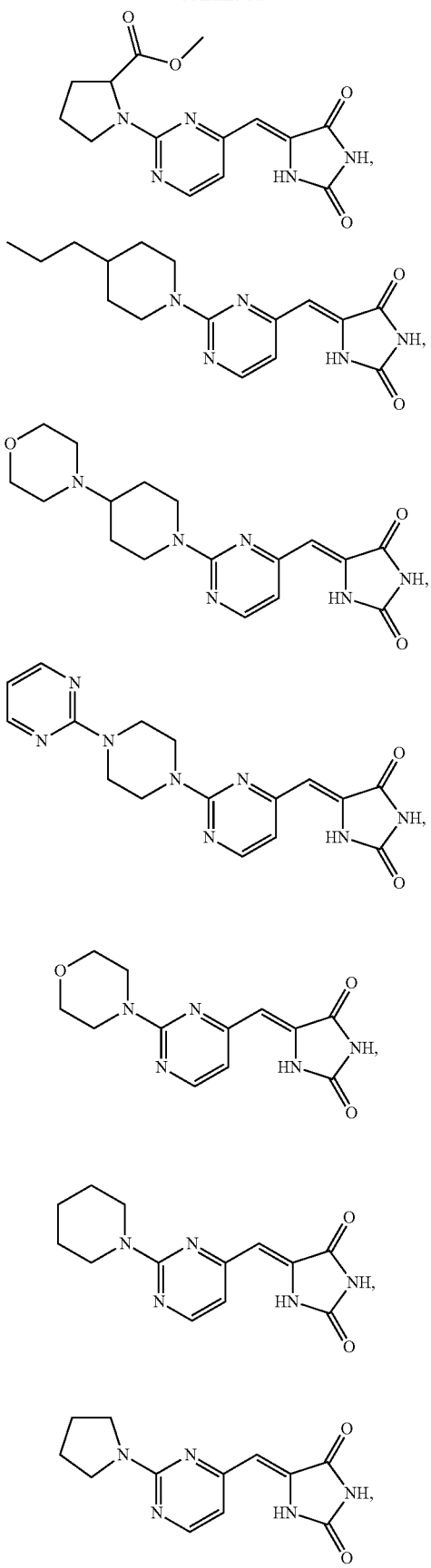
22
-continued
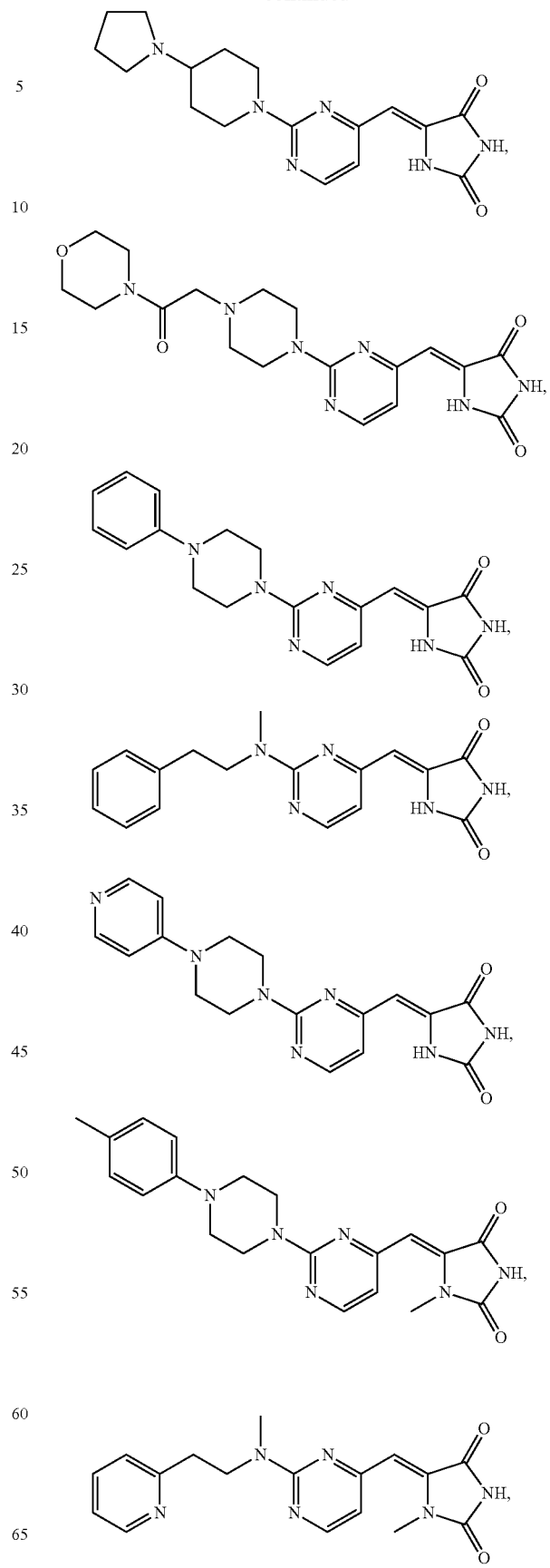

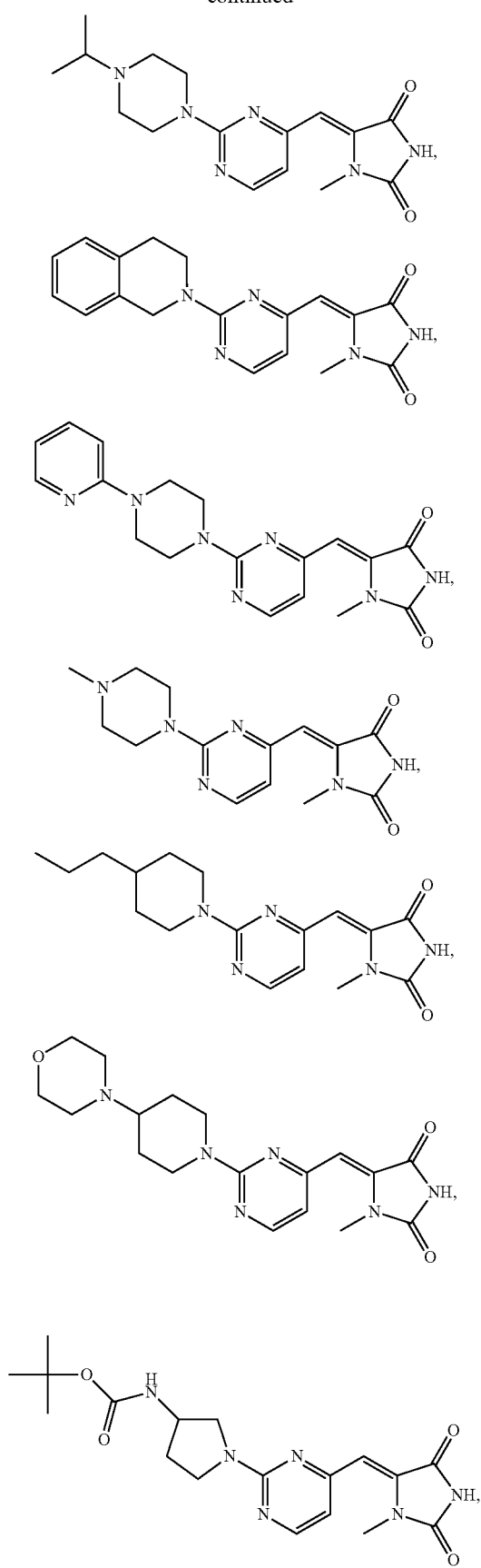
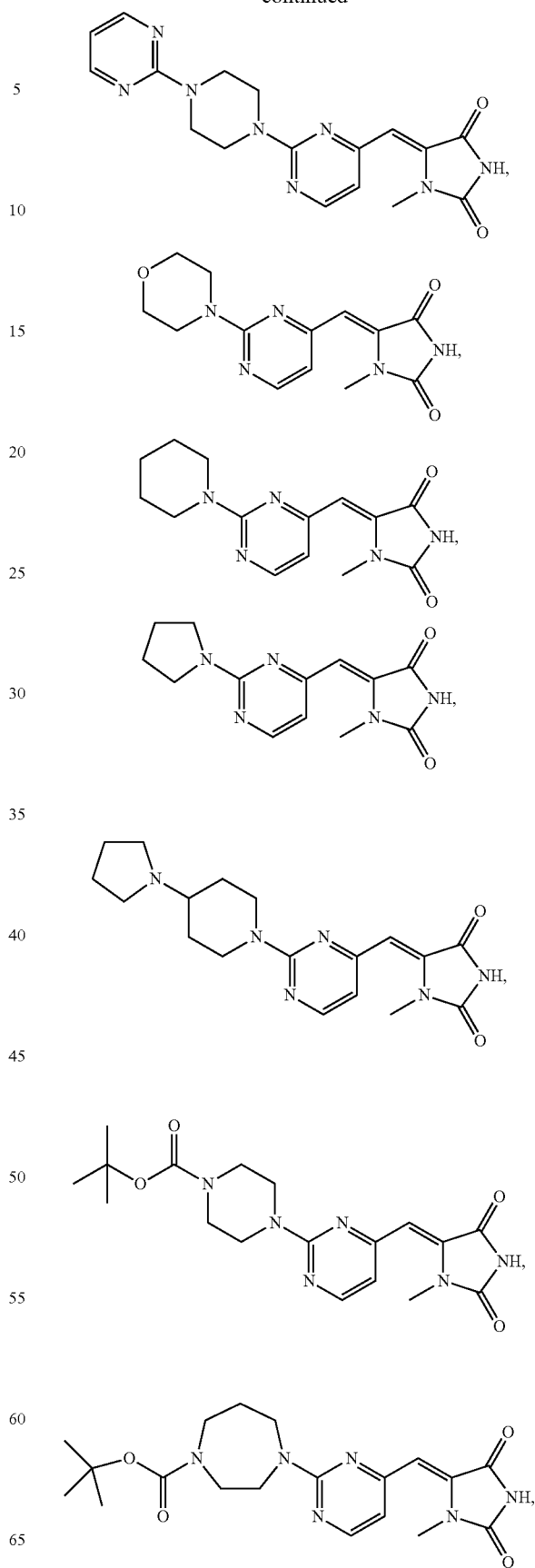

25
-continued
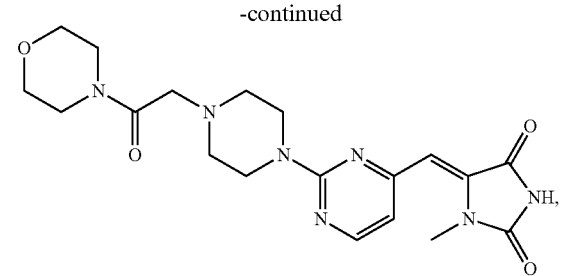
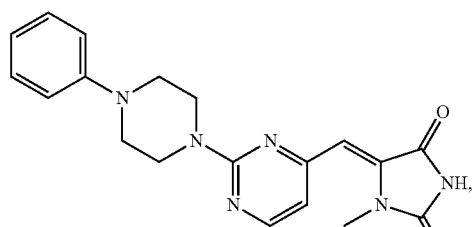
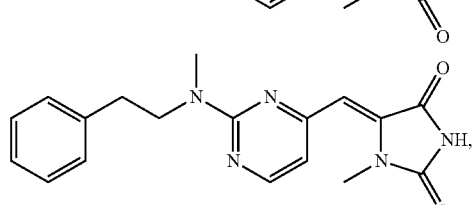
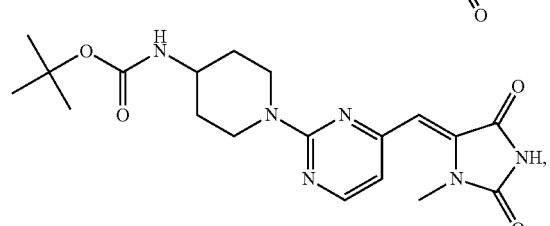
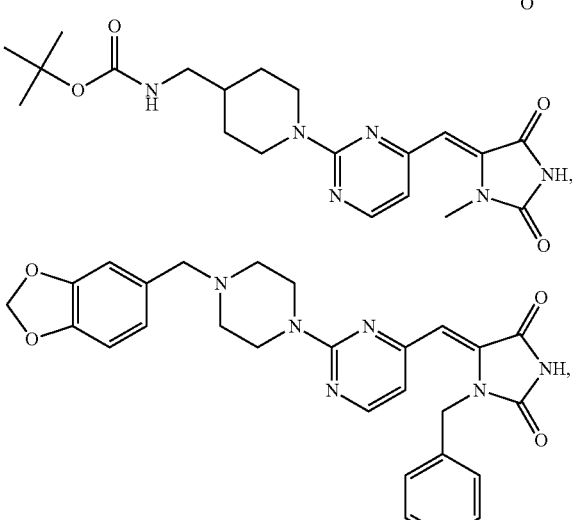
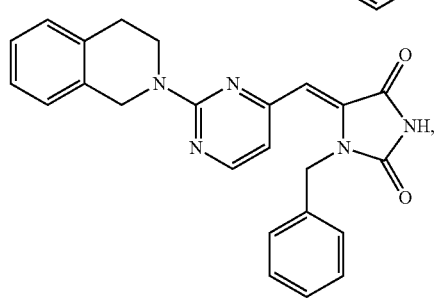
26
-continued
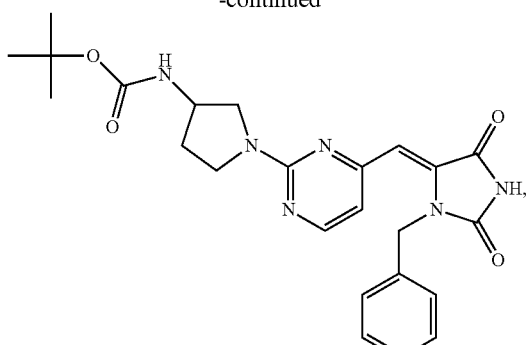
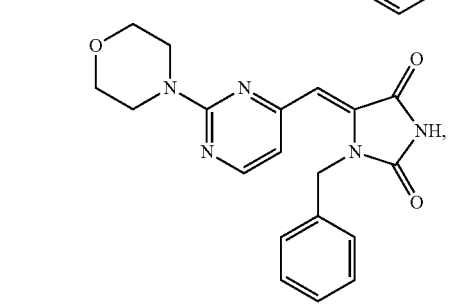
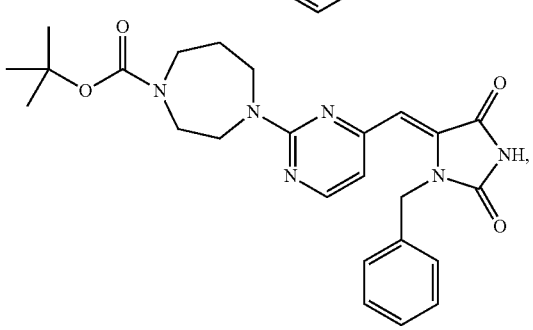
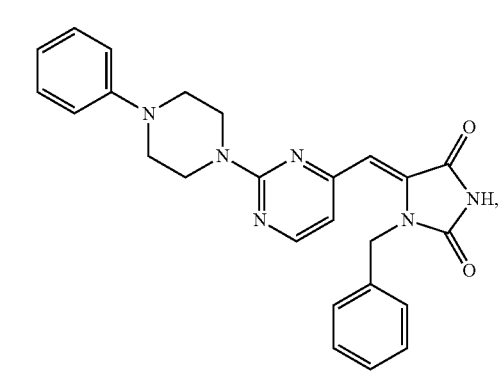
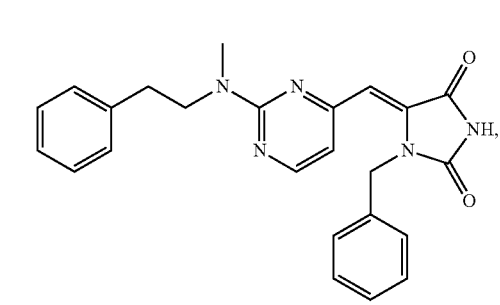

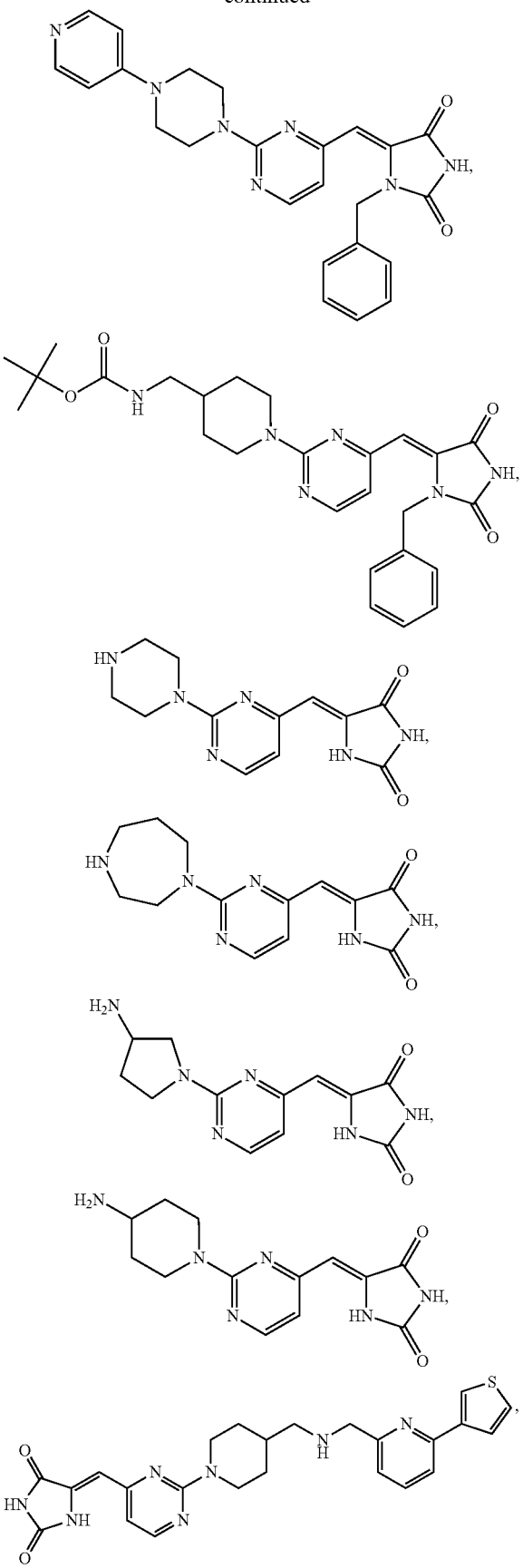
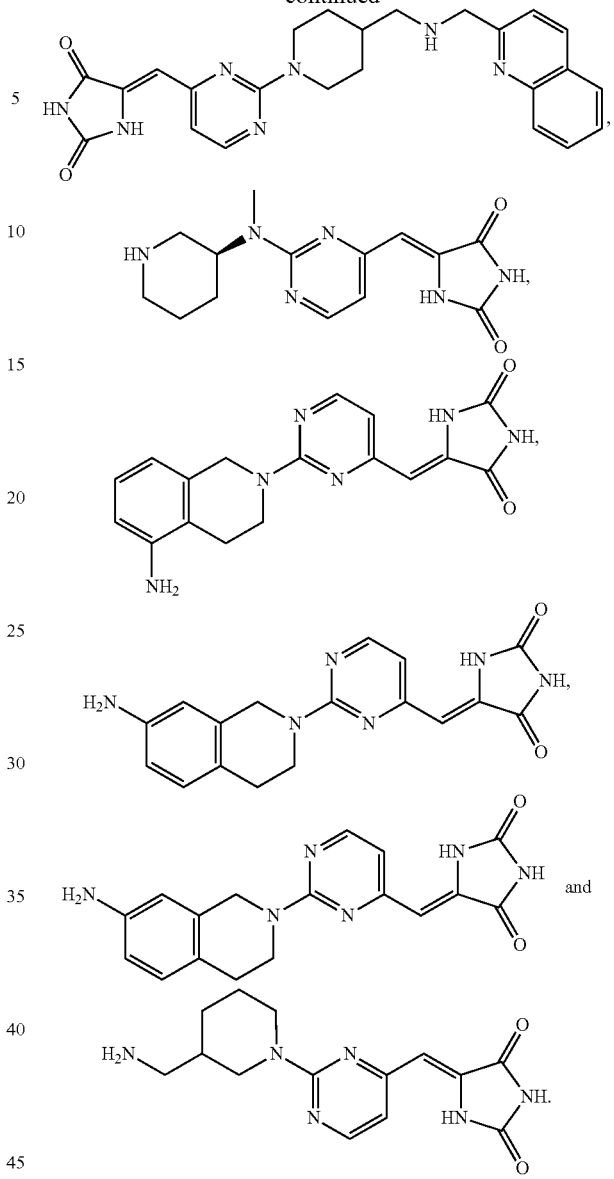

Any one of the aforementioned compounds may exist as the E-geometric isomer, the Z-geometric isomer, or mixtures thereof. For example, in one embodiment, " " in the aforementioned structures represents the E-isomer of the particular compound. In another embodiment, " " represents the Z-isomer of the particular compound. In yet another embodiment, " " represents a mixture of E and Z isomers of the particular compound.

In another embodiment, any one of the aforementioned compounds is an inhibitor of CK1γ1, CK1γ2, or CK1γ3.

In another embodiment, any one of the aforementioned compounds is an inhibitor of the Wnt pathway.

In another embodiment, any one of the aforementioned compounds is an inhibitor of the TGFβ pathway.

In some embodiments, the compound has an $IC_{50}$ of less than 5000 nM for CK1γ1, CK1γ2, or CK1γ3.

In some embodiments, the compound has an $IC_{50}$ of less than 1000 nM for CK1γ1, CK1γ2, or CK1γ3.

In some embodiments, the compound has an $IC_{50}$ of less than 500 nM for CK1γ1, CK1γ2, or CK1γ3.

General Synthetic Schemes

The general synthetic schemes that were utilized to prepare compounds disclosed in this application are described below. For example, compounds of the invention may be prepared as shown in Scheme I:

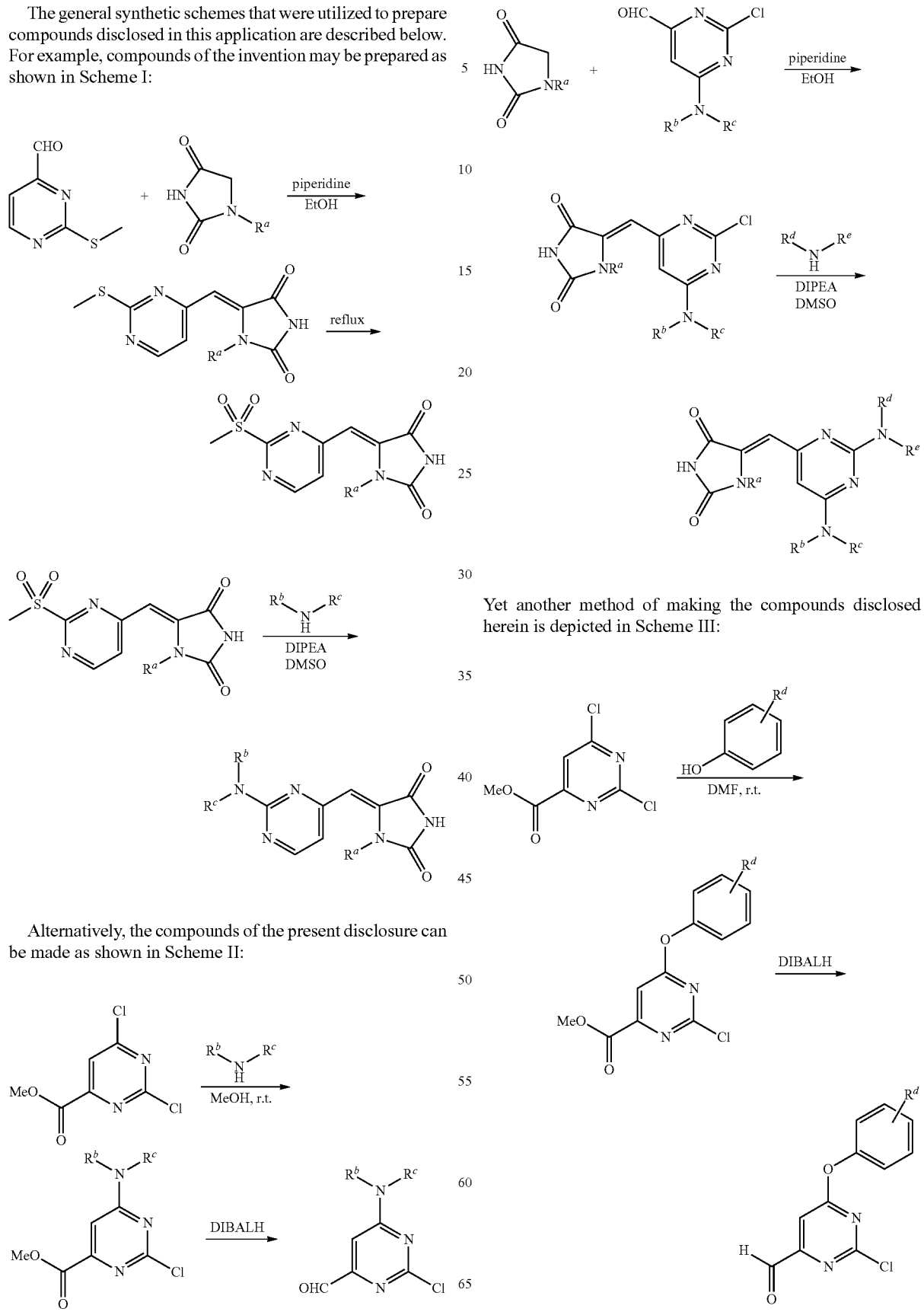

Alternatively, the compounds of the present disclosure can be made as shown in Scheme II:

Yet another method of making the compounds disclosed herein is depicted in Scheme III:

-continued

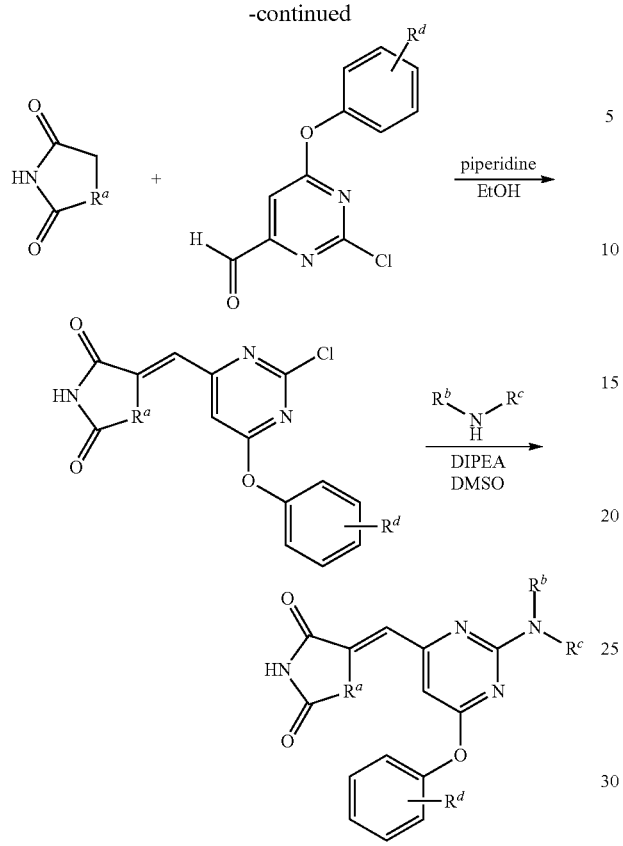

Another method of making the compounds disclosed herein is depicted in Scheme IV:

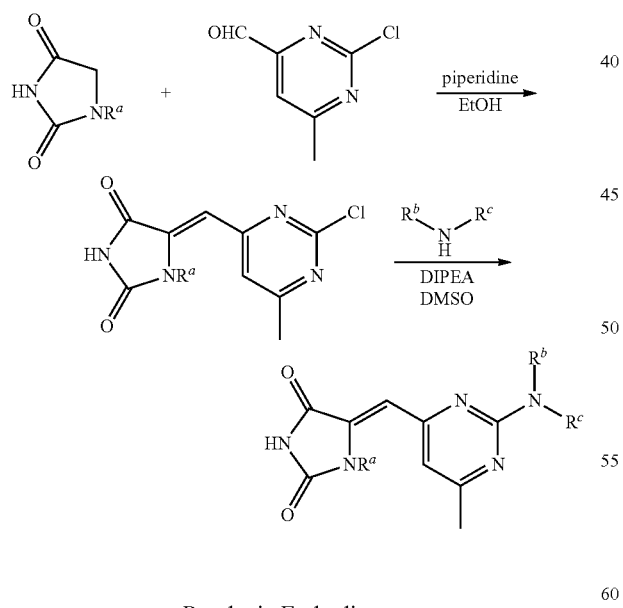

Prophetic Embodiments

Certain compounds of the invention could be made in accordance with the above schemes by reacting an amine (Reactant A) with the hydantoin core (Reactant B). Non-limiting prophetic examples of Reactant A and Reactant B are shown in Table 1 and Table 2, respectively.

TABLE 1

Reactant A Prophetic Examples.

Reactant A #1
Structure

| Molecular Weight | 162.232 |
| Molecular Formula | $C_{10}H_{14}N_2$ |
| Chemical name | 1-phenylpiperazine |

Reactant A #2
Structure

| Molecular Weight | 163.22 |
| Molecular Formula | $C_9H_{13}N_3$ |
| Chemical name | 1-(pyridin-3-yl)piperazine |

Reactant A #3
Structure

| Molecular Weight | 164.208 |
| Molecular Formula | $C_8H_{12}N_4$ |
| Chemical name | 5-(piperazin-1-yl)pyrimidine |

Reactant A #4
Structure

| Molecular Weight | 164.208 |
| Molecular Formula | $C_8H_{12}N_4$ |
| Chemical name | 2-(piperazin-1-yl)pyrimidine |

Reactant A #5
Structure

| Molecular Weight | 205.256 |
| Molecular Formula | $C_{11}H_{15}N_3O$ |
| Chemical name | N-phenylpiperazine-1-carboxamide |

Reactant A #6
Structure

| Molecular Weight | 197.32 |
| Molecular Formula | $C_{11}H_{23}N_3$ |
| Chemical name | 1-(1-ethylpiperidin-4-yl)piperazine |

Reactant A #7
Structure

TABLE 1-continued

Reactant A Prophetic Examples.

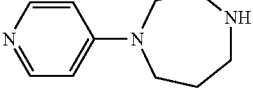

Molecular Weight 177.246
Molecular Formula $C_{10}H_{15}N_3$
Chemical name 1-(pyridin-4-yl)-1,4-diazepane
Reactant A #8
Structure

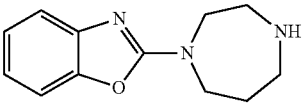 [SMILES: c1ccc2oc(N3CCCNCC3)nc2c1]

Molecular Weight 217.267
Molecular Formula $C_{12}H_{15}N_3O$
Chemical name 2-(1,4-diazepan-1-yl)benzo[d]oxazole
Reactant A #9
Structure

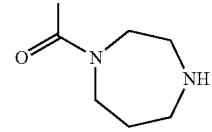

Molecular Weight 219.283
Molecular Formula $C_{12}H_{17}N_3O$
Chemical name N-phenyl-1,4-diazepane-1-carboxamide
Reactant A #10
Structure

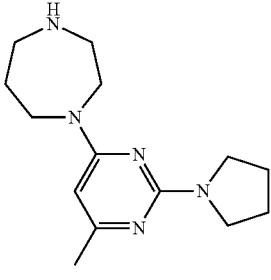 [SMILES: Cc1cc(N2CCCNCC2)nc(N2CCCC2)n1]

Molecular Weight 261.366
Molecular Formula $C_{14}H_{23}N_5$
Chemical name 1-(6-methyl-2-(pyrrolidin-1-yl)pyrimidin-4-yl)-1,4-diazepane
Reactant A #11
Structure

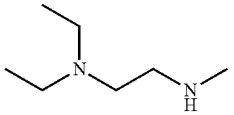

Molecular Weight 130.231
Molecular Formula $C_7H_{18}N_2$
Chemical name N1,N1-diethyl-N2-methylethane-1,2-diamine
Reactant A #12
Structure TABLE 1-continued Reactant A Prophetic Examples.

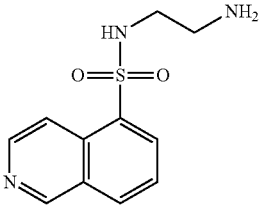 [SMILES: NCCNS(=O)(=O)c1cccc2cnccc12]

Molecular Weight 251.305
Molecular Formula $C_{11}H_{13}O_2S$
Chemical name N-(2-aminoethyl)isoquinoline-5-sulfonamide
Reactant A #13
Structure

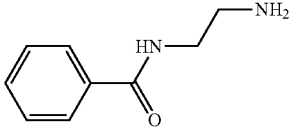 [SMILES: NCCNC(=O)c1ccccc1]

Molecular Weight 164.204
Molecular Formula $C_9H_{12}N_2O$
Chemical name N-(2-aminoethyl)benzamide
Reactant A #14
Structure

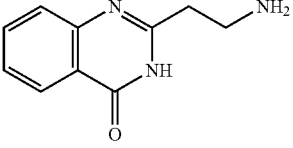 [SMILES: NCCc1nc2ccccc2c(=O)[nH]1]

Molecular Weight 189.214
Molecular Formula $C_{10}H_{11}N_3O$
Chemical name 2-(2-aminoethyl)quinazolin-4(3H)-one
Reactant A #15
Structure

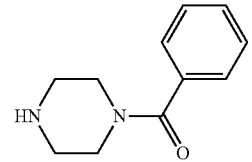 [SMILES: O=C(c1ccccc1)N1CCNCC1]

Molecular Weight 190.242
Molecular Formula $C_{11}H_{14}N_2O$
Chemical name phenyl(piperazin-1-yl)methanone
Reactant A #16
Structure

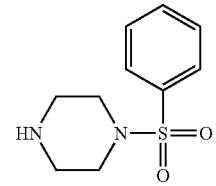 [SMILES: O=S(=O)(c1ccccc1)N1CCNCC1]

Molecular Weight 226.295
Molecular Formula $C_{10}H_{14}N_2O_2S$
Chemical name 1-(phenylsulfonyl)piperazine
Reactant A #17
Structure TABLE 1-continued Reactant A Prophetic Examples.

Molecular Weight 216.279
Molecular Formula C₁₃H₁₆N₂O
Chemical name (hexahydropyrrolo[3,4-c]pyrrol-2(1H)-yl)(phenyl)methanone
Reactant A #18
Structure Molecular Weight 252.333
Molecular Formula C₁₂H₁₆N₂O₂S
Chemical name 2-(phenylsulfonyl)octahydropyrrolo[3,4-c]pyrrole
Reactant A #19
Structure Molecular Weight 231.294
Molecular Formula C₁₃H₁₇N₃O
Chemical name N-phenylhexahydropyrrolo[3,4-c]pyrrole-2(1H)-carboxamide
Reactant A #20
Structure Molecular Weight 217.267
Molecular Formula C₁₂H₁₅N₃O
Chemical name N-phenyl-2,6-diazaspiro[3.3]heptane-2-carboxamide
Reactant A #21
Structure Molecular Weight 202.252
Molecular Formula C₁₂H₁₄N₂O
Chemical name phenyl(2,6-diazaspiro[3.3]heptan-2-yl)methanone
Reactant A #22
Structure TABLE 1-continued Reactant A Prophetic Examples.

Molecular Weight 238306
Molecular Formula C₁₁H₁₄N₂O₂S
Chemical name 2-(phenylsulfony)-2,6-diazaspiro[3.3]heptane

TABLE 2

Reactant B Prophetic Examples.

Reactant B #1
Structure

Molecular Weight 309.708
Molecular Formula C₁₂H₁₂ClN₅O₃
Chemical_name (Z)-5-((2-chloro-6-morpholinopyrimidin-4-yl)methylene)imidazolidine-2,4-dione
Reactant B #2
Structure Molecular Weight 322.75
Molecular Formula C₁₃H₁₅ClN₆O₂
Chemical_name (Z)-5-((2-chloro-6-(4-methylpiperazin-1-yl)pyrimidin-4-yl)methylene)imidazolidine-2,4-dione
Reactant B #3
Structure Molecular Weight 343.768
Molecular Formula C₁₆H₁₄ClN₅O₂
Chemical_name (Z)-5-((6-(benzyl(methyl)amino)-2-chloropyrimidin-4-yl)methylene)imidazolidine-2,4-dione
Reactant B #4
Structure

TABLE 2-continued

Reactant B Prophetic Examples.

Molecular Weight 297.698
Molecular Formula C$_{11}$H$_{12}$ClN$_5$O$_3$
Chemical_name (Z)-5-((2-chloro-6-((2-hydroxyethyl)(methyl)amino)pyrimidin-4-yl)methylene)imidazolidine-2,4-dione
Reactant B #5
Structure Molecular Weight 329.741
Molecular Formula C$_{15}$H$_{12}$ClN$_5$O$_2$
Chemical_name (Z)-5-((2-chloro-6-(methyl(phenyl)amino)pyrimidin-4-yl)methylene)imidazolidine-2,4-dione
Reactant B #6
Structure Molecular Weight 320.688
Molecular Formula C$_{13}$H$_9$ClN$_4$O$_4$
Chemical_name (Z)-5-((2-chloro-6-(furan-2-ylmethoxy)pyrimidin-4-yl)methylene)imidazolidine-2,4-dione
Reactant B #7
Structure Molecular Weight 316.699
Molecular Formula C$_{14}$H$_9$ClN$_4$O$_3$
Chemical_name (Z)-5-((2-chloro-6-phenoxypyrimidin-4-yl)methylene)imidazolidine-2,4-dione
Reactant B #8
Structure

TABLE 2-continued

Reactant B Prophetic Examples.

Molecular Weight 330.726
Molecular Formula C$_{15}$H$_{11}$ClN$_4$O$_3$
Chemical_name (Z)-5-((6-(benzyloxy)-2-chloropyrimidin-4-yl)methylene)imidazolidine-2,4-dione
Reactant B #9
Structure Molecular Weight 298.682
Molecular Formula C$_{11}$H$_{11}$ClN$_4$O$_4$
Chemical_name (Z)-5-((2-chloro-6-(2-methoxyethoxy)pyrimidin-4-yl)methylene)imidazolidine-2,4-dione
Reactant B #10
Structure Molecular Weight 311.724
Molecular Formula C$_{12}$H$_{14}$ClN$_5$O$_3$
Chemical_name (Z)-5-((2-chloro-6-(2-(dimethylamino)ethoxy)pyrimidin-4-yl)methylene)imidazolidine-2,4-dione
Reactant B #11
Structure Molecular Weight 224.604
Molecular Formula C$_8$H$_5$ClN$_4$O$_2$
Chemical_name (Z)-5-((2-chloropyrimidin-4-yl)methylene)imidazolidine-2,4-dione
Reactant B #12
Structure Molecular Weight 225.592
Molecular Formula C$_7$H$_4$ClN$_5$O$_2$
Chemical_name (Z)-5-((4-chloro-1,3,5-triazin-2-yl)methylene)imidazolidine-2,4-dione Additional prophetic embodiments of the invention that may be made in accordance with the above reaction schemes using Reactants A and B are listed in Table 3. The geometric isomers listed in Table 3 are believed to reflect the actual geometry of the prophetic compounds if they were to be made; however, final structural assignments may only be made if the compounds are synthesized and subjected to appropriate 2D NMR experiments. Further, although the compounds are listed as the "Z" geometric isomer, both the E and Z geometric isomers and mixtures thereof are contemplated.

TABLE 3

Additional prophetic embodiments of the invention.

| No | Chemical Name | Formula | Mol Weight | Reactant A | Reactant B |
|---|---|---|---|---|---|
| 1 | (Z)-5-((6-morpholino-2-(4-phenylpiperazin-1-yl)pyrimidin-4-yl)methylene)imidazolidine-2,4-dione | C22H25N7O3 | 435.479 | 1 | 1 |
| 2 | (Z)-5-((6-morpholino-2-(4-(pyridin-3-yl)piperazin-1-yl)pyrimidin-4-yl)methylene)imidazolidine-2,4-dione | C21H24N8O3 | 436.467 | 2 | 1 |
| 3 | (Z)-5-((6-morpholino-2-(4-(pyrimidin-5-yl)piperazin-1-yl)pyrimidin-4-yl)methylene)imidazolidine-2,4-dione | C20H23N9O3 | 437.455 | 3 | 1 |
| 4 | (Z)-5-((6-morpholino-2-(4-(pyrimidin-2-yl)piperazin-1-yl)pyrimidin-4-yl)methylene)imidazolidine-2,4-dione | C20H23N9O3 | 437.455 | 4 | 1 |
| 5 | (Z)-4-(4-((2,4-dioxoimidazolidin-5-ylidene)methyl)-6-morpholinopyrimidin-2-yl)-N-phenylpiperazine-1-carboxamide | C23H26N8O4 | 478.504 | 5 | 1 |
| 6 | (Z)-5-((2-(4-(1-ethylpiperidin-4-yl)piperazin-1-yl)-6-morpholinopyrimidin-4-yl)methylene)imidazolidine-2,4-dione | C23H34N8O3 | 470.568 | 6 | 1 |
| 7 | (Z)-5-((6-morpholino-2-(4-(pyridin-4-yl)-1,4-diazepan-1-yl)pyrimidin-4-yl)methylene)imidazolidine-2,4-dione | C22H26N8O3 | 450.494 | 7 | 1 |
| 8 | (Z)-5-((2-(4-(benzo[d]oxazol-2-yl)-1,4-diazepan-1-yl)-6-morpholinopyrimidin-4-yl)methylene)imidazolidine-2,4-dione | C24H26N8O4 | 490.514 | 8 | 1 |
| 9 | (Z)-4-(4-((2,4-dioxoimidazolidin-5-ylidene)methyl)-6-morpholinopyrimidin-2-yl)-N-phenyl-1,4-diazepane-1-carboxamide | C24H28N8O4 | 492.53 | 9 | 1 |
| 10 | (Z)-5-((2-(4-(6-methyl-2-(pyrrolidin-1-yl)pyrimidin-4-yl)-1,4-diazepan-1-yl)-6-morpholinopyrimidin-4-yl)methylene)imidazolidine-2,4-dione | C26H34N10O3 | 534.613 | 10 | 1 |
| 11 | (Z)-5-((2-((2-(diethylamino)ethyl)(methyl)amino)-6-morpholinopyrimidin-4-yl)methylene)imidazolidine-2,4-dione | C19H29N7O3 | 403.479 | 11 | 1 |
| 12 | (Z)-N-(2-((4-((2,4-dioxoimidazolidin-5-ylidene)methyl)-6-morpholinopyrimidin-2-yl)amino)ethyl)isoquinoline-5-sulfonamide | C23H24N8O5S | 524.552 | 12 | 1 |
| 13 | (Z)-N-(2-((4-((2,4-dioxoimidazolidin-5-ylidene)methyl)-6-morpholinopyrimidin-2-yl)amino)ethyl)benzamide | C21H23N7O4 | 437.452 | 13 | 1 |
| 14 | (Z)-5-((6-morpholino-2-((2-(4-oxo-3,4-dihydroquinazolin-2-yl)ethyl)amino)pyrimidin-4-yl)methylene)imidazolidine-2,4-dione | C22H22N8O4 | 462.461 | 14 | 1 |
| 15 | (Z)-5-((2-(4-benzoylpiperazin-1-yl)-6-morpholinopyrimidin-4-yl)methylene)imidazolidine-2,4-dione | C23H25N7O4 | 463.489 | 15 | 1 |
| 16 | (Z)-5-((6-morpholino-2-(4-(phenylsulfonyl)piperazin-1-yl)pyrimidin-4-yl)methylene)imidazolidine-2,4-dione | C22H25N7O5S | 499.543 | 16 | 1 |
| 17 | (Z)-5-((2-(5-benzoylhexahydropyrrolo[3,4-c]pyrrol-2(1H)-yl)-6-morpholinopyrimidin-4-yl)methylene)imidazolidine-2,4-dione | C25H27N7O4 | 489.526 | 17 | 1 |
| 18 | (Z)-5-((6-morpholino-2-(5-(phenylsulfonyl)hexahydropyrrolo[3,4-c]pyrrol-2(1H)-yl)pyrimidin-4-yl)methylene)imidazolidine-2,4-dione | C24H27N7O5S | 525.58 | 18 | 1 |
| 19 | (Z)-5-(4-((2,4-dioxoimidazolidin-5-ylidene)methyl)-6-morpholinopyrimidin-2-yl)-N-phenylhexahydropyrrolo[3,4-c]pyrrole-2(1H)-carboxamide | C25H28N8O4 | 504.541 | 19 | 1 |
| 20 | (Z)-6-(4-((2,4-dioxoimidazolidin-5-ylidene)methyl)-6-morpholinopyrimidin-2-yl)-N-phenyl-2,6-diazaspiro[3.3]heptane-2-carboxamide | C24H26N8O4 | 490.514 | 20 | 1 |

TABLE 3-continued

Additional prophetic embodiments of the invention.

| No | Chemical Name | Formula | Mol Weight | Reactant A | Reactant B |
|---|---|---|---|---|---|
| 21 | (Z)-5-((2-(6-benzoyl-2,6-diazaspiro[3.3]heptan-2-yl)-6-morpholinopyrimidin-4-yl)methylene)imidazolidine-2,4-dione | C24H25N7O4 | 475.5 | 21 | 1 |
| 22 | (Z)-5-((6-morpholino-2-(6-(phenylsulfonyl)-2,6-diazaspiro[3.3]heptan-2-yl)pyrimidin-4-yl)methylene)imidazolidine-2,4-dione | C23H25N7O5S | 511.554 | 22 | 1 |
| 23 | (Z)-5-((6-(4-methylpiperazin-1-yl)-2-(4-phenylpiperazin-1-yl)pyrimidin-4-yl)methylene)imidazolidine-2,4-dione | C23H28N8O2 | 448.521 | 1 | 2 |
| 24 | (Z)-5-((6-(4-methylpiperazin-1-yl)-2-(4-(pyridin-3-yl)piperazin-1-yl)pyrimidin-4-yl)methylene)imidazolidine-2,4-dione | C22H27N9O2 | 449.509 | 2 | 2 |
| 25 | (Z)-5-((6-(4-methylpiperazin-1-yl)-2-(4-(pyrimidin-5-yl)piperazin-1-yl)pyrimidin-4-yl)methylene)imidazolidine-2,4-dione | C21H26N10O2 | 450.497 | 3 | 2 |
| 26 | (Z)-5-((6-(4-methylpiperazin-1-yl)-2-(4-(pyrimidin-2-yl)piperazin-1-yl)pyrimidin-4-yl)methylene)imidazolidine-2,4-dione | C21H26N10O2 | 450.497 | 4 | 2 |
| 27 | (Z)-4-(4-((2,4-dioxoimidazolidin-5-ylidene)methyl)-6-(4-methylpiperazin-1-yl)pyrimidin-2-yl)-N-phenylpiperazine-1-carboxamide | C24H29N9O3 | 491.546 | 5 | 2 |
| 28 | (Z)-5-((2-(4-(1-ethylpiperidin-4-yl)piperazin-1-yl)-6-(4-methylpiperazin-1-yl)pyrimidin-4-yl)methylene)imidazolidine-2,4-dione | C24H37N9O2 | 483.61 | 6 | 2 |
| 29 | (Z)-5-((6-(4-methylpiperazin-1-yl)-2-(4-(pyridin-4-yl)-1,4-diazepan-1-yl)pyrimidin-4-yl)methylene)imidazolidine-2,4-dione | C23H29N9O2 | 463.535 | 7 | 2 |
| 30 | (Z)-5-((2-(4-(benzo[d]oxazol-2-yl)-1,4-diazepan-1-yl)-6-(4-methylpiperazin-1-yl)pyrimidin-4-yl)methylene)imidazolidine-2,4-dione | C25H29N9O3 | 503.556 | 8 | 2 |
| 31 | (Z)-4-(4-((2,4-dioxoimidazolidin-5-ylidene)methyl)-6-(4-methylpiperazin-1-yl)pyrimidin-2-yl)-N-phenyl-1,4-diazepane-1-carboxamide | C25H31N9O3 | 505.572 | 9 | 2 |
| 32 | (Z)-5-((2-(4-(6-methyl-2-(pyrrolidin-1-yl)pyrimidin-4-yl)-1,4-diazepan-1-yl)-6-(4-methylpiperazin-1-yl)pyrimidin-4-yl)methylene)imidazolidine-2,4-dione | C27H37N11O2 | 547.655 | 10 | 2 |
| 33 | (Z)-5-((2-((2-(diethylamino)ethyl)(methyl)amino)-6-(4-methylpiperazin-1-yl)pyrimidin-4-yl)methylene)imidazolidine-2,4-dione | C20H32N8O2 | 416.52 | 11 | 2 |
| 34 | (Z)-N-(2-((4-((2,4-dioxoimidazolidin-5-ylidene)methyl)-6-(4-methylpiperazin-1-yl)pyrimidin-2-yl)amino)ethyl)isoquinoline-5-sulfonamide | C24H27N9O4S | 537.594 | 12 | 2 |
| 35 | (Z)-N-(2-((4-((2,4-dioxoimidazolidin-5-ylidene)methyl)-6-(4-methylpiperazin-1-yl)pyrimidin-2-yl)amino)ethyl)benzamide | C22H26N8O3 | 450.494 | 13 | 2 |
| 36 | (Z)-5-((6-(4-methylpiperazin-1-yl)-2-((2-(4-oxo-3,4-dihydroquinazolin-2-yl)ethyl)amino)pyrimidin-4-yl)methylene)imidazolidine-2,4-dione | C23H25N9O3 | 475.503 | 14 | 2 |
| 37 | (Z)-5-((2-(4-benzoylpiperazin-1-yl)-6-(4-methylpiperazin-1-yl)pyrimidin-4-yl)methylene)imidazolidine-2,4-dione | C24H28N8O3 | 476.531 | 15 | 2 |
| 38 | (Z)-5-((6-(4-methylpiperazin-1-yl)-2-(4-(phenylsulfonyl)piperazin-1-yl)pyrimidin-4-yl)methylene)imidazolidine-2,4-dione | C23H28N8O4S | 512.585 | 16 | 2 |
| 39 | (Z)-5-((2-(5-benzoylhexahydropyrrolo[3,4-c]pyrrol-2(1H)-yl)-6-(4-methylpiperazin-1-yl)pyrimidin-4-yl)methylene)imidazolidine-2,4-dione | C26H30N8O3 | 502.568 | 17 | 2 |
| 40 | (Z)-5-((6-(4-methylpiperazin-1-yl)-2-(5-(phenylsulfonyl)hexahydropyrrolo[3,4-c]pyrrol-2(1H)-yl)pyrimidin-4-yl)methylene)imidazolidine-2,4-dione | C25H30N8O4S | 538.622 | 18 | 2 |
| 41 | (Z)-5-(4-((2,4-dioxoimidazolidin-5-ylidene)methyl)-6-(4-methylpiperazin-1-yl)pyrimidin-2-yl)-N-phenylhexahydropyrrolo[3,4-c]pyrrole-2(1H)-carboxamide | C26H31N9O3 | 517.583 | 19 | 2 |

TABLE 3-continued

Additional prophetic embodiments of the invention.

| No | Chemical Name | Formula | Mol Weight | Reactant A | Reactant B |
|---|---|---|---|---|---|
| 42 | (Z)-6-(4-((2,4-dioxoimidazolidin-5-ylidene)methyl)-6-(4-methylpiperazin-1-yl)pyrimidin-2-yl)-N-phenyl-2,6-diazaspiro[3.3]heptane-2-carboxamide | C25H29N9O3 | 503.556 | 20 | 2 |
| 43 | (Z)-5-((2-(6-benzoyl-2,6-diazaspiro[3.3]heptan-2-yl)-6-(4-methylpiperazin-1-yl)pyrimidin-4-yl)methylene)imidazolidine-2,4-dione | C25H28N8O3 | 488.542 | 21 | 2 |
| 44 | (Z)-5-((6-(4-methylpiperazin-1-yl)-2-(6-(phenylsulfonyl)-2,6-diazaspiro[3.3]heptan-2-yl)pyrimidin-4-yl)methylene)imidazolidine-2,4-dione | C24H28N8O4S | 524.595 | 22 | 2 |
| 45 | (Z)-5-((6-(benzyl(methyl)amino)-2-(4-phenylpiperazin-1-yl)pyrimidin-4-yl)methylene)imidazolidine-2,4-dione | C26H27N7O2 | 469.538 | 1 | 3 |
| 46 | (Z)-5-((6-(benzyl(methyl)amino)-2-(4-(pyridin-3-yl)piperazin-1-yl)pyrimidin-4-yl)methylene)imidazolidine-2,4-dione | C25H26N8O2 | 470.526 | 2 | 3 |
| 47 | (Z)-5-((6-(benzyl(methyl)amino)-2-(4-(pyrimidin-5-yl)piperazin-1-yl)pyrimidin-4-yl)methylene)imidazolidine-2,4-dione | C24H25N9O2 | 471.514 | 3 | 3 |
| 48 | (Z)-5-((6-(benzyl(methyl)amino)-2-(4-(pyrimidin-2-yl)piperazin-1-yl)pyrimidin-4-yl)methylene)imidazolidine-2,4-dione | C24H25N9O2 | 471.514 | 4 | 3 |
| 49 | (Z)-4-(4-(benzyl(methyl)amino)-6-((2,4-dioxoimidazolidin-5-ylidene)methyl)pyrimidin-2-yl)-N-phenylpiperazine-1-carboxamide | C27H28N8O3 | 512.563 | 5 | 3 |
| 50 | (Z)-5-((6-(benzyl(methyl)amino)-2-(4-(1-ethylpiperidin-4-yl)piperazin-1-yl)pyrimidin-4-yl)methylene)imidazolidine-2,4-dione | C27H36N8O2 | 504.627 | 6 | 3 |
| 51 | (Z)-5-((6-(benzyl(methyl)amino)-2-(4-(pyridin-4-yl)-1,4-diazepan-1-yl)pyrimidin-4-yl)methylene)imidazolidine-2,4-dione | C26H28N8O2 | 484.553 | 7 | 3 |
| 52 | (Z)-5-((2-(4-(benzo[d]oxazol-2-yl)-1,4-diazepan-1-yl)-6-(benzyl(methyl)amino)pyrimidin-4-yl)methylene)imidazolidine-2,4-dione | C28H28N8O3 | 524.574 | 8 | 3 |
| 53 | (Z)-4-(4-(benzyl(methyl)amino)-6-((2,4-dioxoimidazolidin-5-ylidene)methyl)pyrimidin-2-yl)-N-phenyl-1,4-diazepane-1-carboxamide | C28H30N8O3 | 526.59 | 9 | 3 |
| 54 | (Z)-5-((6-(benzyl(methyl)amino)-2-(4-(6-methyl-2-(pyrrolidin-1-yl)pyrimidin-4-yl)-1,4-diazepan-1-yl)pyrimidin-4-yl)methylene)imidazolidine-2,4-dione | C30H36N10O2 | 568.673 | 10 | 3 |
| 55 | (Z)-5-((6-(benzyl(methyl)amino)-2-((2-(diethylamino)ethyl)(methyl)amino)pyrimidin-4-yl)methylene)imidazolidine-2,4-dione | C23H31N7O2 | 437.538 | 11 | 3 |
| 56 | (Z)-N-(2-((4-(benzyl(methyl)amino)-6-((2,4-dioxoimidazolidin-5-ylidene)methyl)pyrimidin-2-yl)amino)ethyl)isoquinoline-5-sulfonamide | C27H26N8O4S | 558.612 | 12 | 3 |
| 57 | (Z)-N-(2-((4-(benzyl(methyl)amino)-6-((2,4-dioxoimidazolidin-5-ylidene)methyl)pyrimidin-2-yl)amino)ethyl)benzamide | C25H25N7O3 | 471.511 | 13 | 3 |
| 58 | (Z)-5-((6-(benzyl(methyl)amino)-2-((2-(4-oxo-3,4-dihydroquinazolin-2-yl)ethyl)amino)pyrimidin-4-yl)methylene)imidazolidine-2,4-dione | C26H24N8O3 | 496.521 | 14 | 3 |
| 59 | (Z)-5-((2-(4-benzoylpiperazin-1-yl)-6-(benzyl(methyl)amino)pyrimidin-4-yl)methylene)imidazolidine-2,4-dione | C27H27N7O3 | 497.548 | 15 | 3 |
| 60 | (Z)-5-((6-(benzyl(methyl)amino)-2-(4-(phenylsulfonyl)piperazin-1-yl)pyrimidin-4-yl)methylene)imidazolidine-2,4-dione | C26H27N7O4S | 533.602 | 16 | 3 |
| 61 | (Z)-5-((2-(5-benzoylhexahydropyrrolo[3,4-c]pyrrol-2(1H)-yl)-6-(benzyl(methyl)amino)pyrimidin-4-yl)methylene)imidazolidine-2,4-dione | C29H29N7O3 | 523.586 | 17 | 3 |
| 62 | (Z)-5-((6-(benzyl(methyl)amino)-2-(5-(phenylsulfonyl)hexahydropyrrolo[3,4-c]pyrrol-2(1H)-yl)pyrimidin-4-yl)methylene)imidazolidine-2,4-dione | C28H29N7O4S | 559.639 | 18 | 3 |
| 63 | (Z)-5-(4-(benzyl(methyl)amino)-6-((2,4-dioxoimidazolidin-5-ylidene)methyl)pyrimidin-2-yl)-N-phenylhexahydropyrrolo[3,4-c]pyrrole-2(1H)-carboxamide | C29H30N8O3 | 538.6 | 19 | 3 |

TABLE 3-continued

Additional prophetic embodiments of the invention.

| No | Chemical Name | Formula | Mol Weight | Reactant A | Reactant B |
|----|---------------|---------|------------|------------|------------|
| 64 | (Z)-6-(4-(benzyl(methyl)amino)-6-((2,4-dioxoimidazolidin-5-ylidene)methyl)pyrimidin-2-yl)-N-phenyl-2,6-diazaspiro[3.3]heptane-2-carboxamide | C28H28N8O3 | 524.574 | 20 | 3 |
| 65 | (Z)-5-((2-(6-benzoyl-2,6-diazaspiro[3.3]heptan-2-yl)-6-(benzyl(methyl)amino)pyrimidin-4-yl)methylene)imidazolidine-2,4-dione | C28H27N7O3 | 509.559 | 21 | 3 |
| 66 | (Z)-5-((6-(benzyl(methyl)amino)-2-(6-(phenylsulfonyl)-2,6-diazaspiro[3.3]heptan-2-yl)pyrimidin-4-yl)methylene)imidazolidine-2,4-dione | C27H27N7O4S | 545.613 | 22 | 3 |
| 67 | (Z)-5-((6-((2-hydroxyethyl)(methyl)amino)-2-(4-phenylpiperazin-1-yl)pyrimidin-4-yl)methylene)imidazolidine-2,4-dione | C21H25N7O3 | 423.468 | 1 | 4 |
| 68 | (Z)-5-((6-((2-hydroxyethyl)(methyl)amino)-2-(4-(pyridin-3-yl)piperazin-1-yl)pyrimidin-4-yl)methylene)imidazolidine-2,4-dione | C20H24N8O3 | 424.456 | 2 | 4 |
| 69 | (Z)-5-((6-((2-hydroxyethyl)(methyl)amino)-2-(4-(pyrimidin-5-yl)piperazin-1-yl)pyrimidin-4-yl)methylene)imidazolidine-2,4-dione | C19H23N9O3 | 425.444 | 3 | 4 |
| 70 | (Z)-5-((6-((2-hydroxyethyl)(methyl)amino)-2-(4-(pyrimidin-2-yl)piperazin-1-yl)pyrimidin-4-yl)methylene)imidazolidine-2,4-dione | C19H23N9O3 | 425.444 | 4 | 4 |
| 71 | (Z)-4-(4-((2,4-dioxoimidazolidin-5-ylidene)methyl)-6-((2-hydroxyethyl)(methyl)amino)pyrimidin-2-yl)-N-phenylpiperazine-1-carboxamide | C22H26N8O4 | 466.493 | 5 | 4 |
| 72 | (Z)-5-((2-(4-(1-ethylpiperidin-4-yl)piperazin-1-yl)-6-((2-hydroxyethyl)(methyl)amino)pyrimidin-4-yl)methylene)imidazolidine-2,4-dione | C22H34N8O3 | 458.557 | 6 | 4 |
| 73 | (Z)-5-((6-((2-hydroxyethyl)(methyl)amino)-2-(4-(pyridin-4-yl)-1,4-diazepan-1-yl)pyrimidin-4-yl)methylene)imidazolidine-2,4-dione | C21H26N8O3 | 438.483 | 7 | 4 |
| 74 | (Z)-5-((2-(4-(benzo[d]oxazol-2-yl)-1,4-diazepan-1-yl)-6-((2-hydroxyethyl)(methyl)amino)pyrimidin-4-yl)methylene)imidazolidine-2,4-dione | C23H26N8O4 | 478.504 | 8 | 4 |
| 75 | (Z)-4-(4-((2,4-dioxoimidazolidin-5-ylidene)methyl)-6-((2-hydroxyethyl)(methyl)amino)pyrimidin-2-yl)-N-phenyl-1,4-diazepane-1-carboxamide | C23H28N8O4 | 480.52 | 9 | 4 |
| 76 | (Z)-5-((6-((2-hydroxyethyl)(methyl)amino)-2-(4-(6-methyl-2-(pyrrolidin-1-yl)pyrimidin-4-yl)-1,4-diazepan-1-yl)pyrimidin-4-yl)methylene)imidazolidine-2,4-dione | C25H34N10O3 | 522.603 | 10 | 4 |
| 77 | (Z)-5-((2-((2-(diethylamino)ethyl)(methyl)amino)-6-((2-hydroxyethyl)(methyl)amino)pyrimidin-4-yl)methylene)imidazolidine-2,4-dione | C18H29N7O3 | 391.468 | 11 | 4 |
| 78 | (Z)-N-(2-((4-((2,4-dioxoimidazolidin-5-ylidene)methyl)-6-((2-hydroxyethyl)(methyl)amino)pyrimidin-2-yl)amino)ethyl)isoquinoline-5-sulfonamide | C22H24N8O5S | 512.542 | 12 | 4 |
| 79 | (Z)-N-(2-((4-((2,4-dioxoimidazolidin-5-ylidene)methyl)-6-((2-hydroxyethyl)(methyl)amino)pyrimidin-2-yl)amino)ethyl)benzamide | C20H23N7O4 | 425.441 | 13 | 4 |
| 80 | (Z)-5-((6-((2-hydroxyethyl)(methyl)amino)-2-((2-(4-oxo-3,4-dihydroquinazolin-2-yl)ethyl)amino)pyrimidin-4-yl)methylene)imidazolidine-2,4-dione | C21H22N8O4 | 450.451 | 14 | 4 |
| 81 | (Z)-5-((2-(4-benzoylpiperazin-1-yl)-6-((2-hydroxyethyl)(methyl)amino)pyrimidin-4-yl)methylene)imidazolidine-2,4-dione | C22H25N7O4 | 451.478 | 15 | 4 |
| 82 | (Z)-5-((6-((2-hydroxyethyl)(methyl)amino)-2-(4-(phenylsulfonyl)piperazin-1-yl)pyrimidin-4-yl)methylene)imidazolidine-2,4-dione | C21H25N7O5S | 487.532 | 16 | 4 |
| 83 | (Z)-5-((2-(5-benzoylhexahydropyrrolo[3,4-c]pyrrol-2(1H)-yl)-6-((2-hydroxyethyl)(methyl)amino)pyrimidin-4-yl)methylene)imidazolidine-2,4-dione | C24H27N7O4 | 477.516 | 17 | 4 |

TABLE 3-continued

Additional prophetic embodiments of the invention.

| No | Chemical Name | Formula | Mol Weight | Reactant A | Reactant B |
|---|---|---|---|---|---|
| 84 | (Z)-5-((6-((2-hydroxyethyl)(methyl)amino)-2-(5-(phenylsulfonyl)hexahydropyrrolo[3,4-c]pyrrol-2(1H)-yl)pyrimidin-4-yl)methylene)imidazolidine-2,4-dione | C23H27N7O5S | 513.569 | 18 | 4 |
| 85 | (Z)-5-(4-((2,4-dioxoimidazolidin-5-ylidene)methyl)-6-((2-hydroxyethyl)(methyl)amino)pyrimidin-2-yl)-N-phenylhexahydropyrrolo[3,4-c]pyrrole-2(1H)-carboxamide | C24H28N8O4 | 492.53 | 19 | 4 |
| 86 | (Z)-6-(4-((2,4-dioxoimidazolidin-5-ylidene)methyl)-6-((2-hydroxyethyl)(methyl)amino)pyrimidin-2-yl)-N-phenyl-2,6-diazaspiro[3.3]heptane-2-carboxamide | C23H26N8O4 | 478.504 | 20 | 4 |
| 87 | (Z)-5-((2-(6-benzoyl-2,6-diazaspiro[3.3]heptan-2-yl)-6-((2-hydroxyethyl)(methyl)amino)pyrimidin-4-yl)methylene)imidazolidine-2,4-dione | C23H25N7O4 | 463.489 | 21 | 4 |
| 88 | (Z)-5-((6-((2-hydroxyethyl)(methyl)amino)-2-(6-(phenylsulfonyl)-2,6-diazaspiro[3.3]heptan-2-yl)pyrimidin-4-yl)methylene)imidazolidine-2,4-dione | C22H25N7O5S | 499.543 | 22 | 4 |
| 89 | (Z)-5-((6-(methyl(phenyl)amino)-2-(4-phenylpiperazin-1-yl)pyrimidin-4-yl)methylene)imidazolidine-2,4-dione | C25H25N7O2 | 455.512 | 1 | 5 |
| 90 | (Z)-5-((6-(methyl(phenyl)amino)-2-(4-(pyridin-3-yl)piperazin-1-yl)pyrimidin-4-yl)methylene)imidazolidine-2,4-dione | C24H24N8O2 | 456.5 | 2 | 5 |
| 91 | (Z)-5-((6-(methyl(phenyl)amino)-2-(4-(pyrimidin-5-yl)piperazin-1-yl)pyrimidin-4-yl)methylene)imidazolidine-2,4-dione | C23H23N9O2 | 457.488 | 3 | 5 |
| 92 | (Z)-5-((6-(methyl(phenyl)amino)-2-(4-(pyrimidin-2-yl)piperazin-1-yl)pyrimidin-4-yl)methylene)imidazolidine-2,4-dione | C23H23N9O2 | 457.488 | 4 | 5 |
| 93 | (Z)-4-(4-((2,4-dioxoimidazolidin-5-ylidene)methyl)-6-(methyl(phenyl)amino)pyrimidin-2-yl)-N-phenylpiperazine-1-carboxamide | C26H26N8O3 | 498.536 | 5 | 5 |
| 94 | (Z)-5-((2-(4-(1-ethylpiperidin-4-yl)piperazin-1-yl)-6-(methyl(phenyl)amino)pyrimidin-4-yl)methylene)imidazolidine-2,4-dione | C26H34N8O2 | 490.601 | 6 | 5 |
| 95 | (Z)-5-((6-(methyl(phenyl)amino)-2-(4-(pyridin-4-yl)-1,4-diazepan-1-yl)pyrimidin-4-yl)methylene)imidazolidine-2,4-dione | C25H26N8O2 | 470.526 | 7 | 5 |
| 96 | (Z)-5-((2-(4-(benzo[d]oxazol-2-yl)-1,4-diazepan-1-yl)-6-(methyl(phenyl)amino)pyrimidin-4-yl)methylene)imidazolidine-2,4-dione | C27H26N8O3 | 510.547 | 8 | 5 |
| 97 | (Z)-4-(4-((2,4-dioxoimidazolidin-5-ylidene)methyl)-6-(methyl(phenyl)amino)pyrimidin-2-yl)-N-phenyl-1,4-diazepane-1-carboxamide | C27H28N8O3 | 512.563 | 9 | 5 |
| 98 | (Z)-5-((6-(methyl(phenyl)amino)-2-(4-(6-methyl-2-(pyrrolidin-1-yl)pyrimidin-4-yl)-1,4-diazepan-1-yl)pyrimidin-4-yl)methylene)imidazolidine-2,4-dione | C29H34N10O2 | 554.646 | 10 | 5 |
| 99 | (Z)-5-((2-((2-(diethylamino)ethyl)(methyl)amino)-6-(methyl(phenyl)amino)pyrimidin-4-yl)methylene)imidazolidine-2,4-dione | C22H29N7O2 | 423.511 | 11 | 5 |
| 100 | (Z)-N-(2-((4-((2,4-dioxoimidazolidin-5-ylidene)methyl)-6-(methyl(phenyl)amino)pyrimidin-2-yl)amino)ethyl)isoquinoline-5-sulfonamide | C26H24N8O4S | 544.585 | 12 | 5 |
| 101 | (Z)-N-(2-((4-((2,4-dioxoimidazolidin-5-ylidene)methyl)-6-(methyl(phenyl)amino)pyrimidin-2-yl)amino)ethyl)benzamide | C24H23N7O3 | 457.485 | 13 | 5 |
| 102 | (Z)-5-((6-(methyl(phenyl)amino)-2-((2-(4-oxo-3,4-dihydroquinazolin-2-yl)ethyl)amino)pyrimidin-4-yl)methylene)imidazolidine-2,4-dione | C25H22N8O3 | 482.494 | 14 | 5 |

TABLE 3-continued

Additional prophetic embodiments of the invention.

| No | Chemical Name | Formula | Mol Weight | Reactant A | Reactant B |
|---|---|---|---|---|---|
| 103 | (Z)-5-((2-(4-benzoylpiperazin-1-yl)-6-(methyl(phenyl)amino)pyrimidin-4-yl)methylene)imidazolidine-2,4-dione | C26H25N7O3 | 483.522 | 15 | 5 |
| 104 | (Z)-5-((6-(methyl(phenyl)amino)-2-(4-(phenylsulfonyl)piperazin-1-yl)pyrimidin-4-yl)methylene)imidazolidine-2,4-dione | C25H25N7O4S | 519.575 | 16 | 5 |
| 105 | (Z)-5-((2-(5-benzoylhexahydropyrrolo[3,4-c]pyrrol-2(1H)-yl)-6-(methyl(phenyl)amino)pyrimidin-4-yl)methylene)imidazolidine-2,4-dione | C28H27N7O3 | 509.559 | 17 | 5 |
| 106 | (Z)-5-((6-(methyl(phenyl)amino)-2-(5-(phenylsulfonyl)hexahydropyrrolo[3,4-c]pyrrol-2(1H)-yl)pyrimidin-4-yl)methylene)imidazolidine-2,4-dione | C27H27N7O4S | 545.613 | 18 | 5 |
| 107 | (Z)-5-(4-((2,4-dioxoimidazolidin-5-ylidene)methyl)-6-(methyl(phenyl)amino)pyrimidin-2-yl)-N-phenylhexahydropyrrolo[3,4-c]pyrrole-2(1H)-carboxamide | C28H28N8O3 | 524.574 | 19 | 5 |
| 108 | (Z)-6-(4-((2,4-dioxoimidazolidin-5-ylidene)methyl)-6-(methyl(phenyl)amino)pyrimidin-2-yl)-N-phenyl-2,6-diazaspiro[3.3]heptane-2-carboxamide | C27H26N8O3 | 510.547 | 20 | 5 |
| 109 | (Z)-5-((2-(6-benzoyl-2,6-diazaspiro[3.3]heptan-2-yl)-6-(methyl(phenyl)amino)pyrimidin-4-yl)methylene)imidazolidine-2,4-dione | C27H25N7O3 | 495.533 | 21 | 5 |
| 110 | (Z)-5-((6-(methyl(phenyl)amino)-2-(6-(phenylsulfonyl)-2,6-diazaspiro[3.3]heptan-2-yl)pyrimidin-4-yl)methylene)imidazolidine-2,4-dione | C26H25N7O4S | 531.586 | 22 | 5 |
| 111 | (Z)-5-((6-(furan-2-ylmethoxy)-2-(4-phenylpiperazin-1-yl)pyrimidin-4-yl)methylene)imidazolidine-2,4-dione | C23H22N6O4 | 446.459 | 1 | 6 |
| 112 | (Z)-5-((6-(furan-2-ylmethoxy)-2-(4-(pyridin-3-yl)piperazin-1-yl)pyrimidin-4-yl)methylene)imidazolidine-2,4-dione | C22H21N7O4 | 447.447 | 2 | 6 |
| 113 | (Z)-5-((6-(furan-2-ylmethoxy)-2-(4-(pyrimidin-5-yl)piperazin-1-yl)pyrimidin-4-yl)methylene)imidazolidine-2,4-dione | C21H20N8O4 | 448.435 | 3 | 6 |
| 114 | (Z)-5-((6-(furan-2-ylmethoxy)-2-(4-(pyrimidin-2-yl)piperazin-1-yl)pyrimidin-4-yl)methylene)imidazolidine-2,4-dione | C21H20N8O4 | 448.435 | 4 | 6 |
| 115 | (Z)-4-(4-((2,4-dioxoimidazolidin-5-ylidene)methyl)-6-(furan-2-ylmethoxy)pyrimidin-2-yl)-N-phenylpiperazine-1-carboxamide | C24H23N7O5 | 489.483 | 5 | 6 |
| 116 | (Z)-5-((2-(4-(1-ethylpiperidin-4-yl)piperazin-1-yl)-6-(furan-2-ylmethoxy)pyrimidin-4-yl)methylene)imidazolidine-2,4-dione | C24H31N7O4 | 481.547 | 6 | 6 |
| 117 | (Z)-5-((6-(furan-2-ylmethoxy)-2-(4-(pyridin-4-yl)-1,4-diazepan-1-yl)pyrimidin-4-yl)methylene)imidazolidine-2,4-dione | C23H23N7O4 | 461.473 | 7 | 6 |
| 118 | (Z)-5-((2-(4-(benzo[d]oxazol-2-yl)-1,4-diazepan-1-yl)-6-(furan-2-ylmethoxy)pyrimidin-4-yl)methylene)imidazolidine-2,4-dione | C25H23N7O5 | 501.494 | 8 | 6 |
| 119 | (Z)-4-(4-((2,4-dioxoimidazolidin-5-ylidene)methyl)-6-(furan-2-ylmethoxy)pyrimidin-2-yl)-N-phenyl-1,4-diazepane-1-carboxamide | C25H25N7O5 | 503.51 | 9 | 6 |
| 120 | (Z)-5-((6-(furan-2-ylmethoxy)-2-(4-(6-methyl-2-(pyrrolidin-1-yl)pyrimidin-4-yl)-1,4-diazepan-1-yl)pyrimidin-4-yl)methylene)imidazolidine-2,4-dione | C27H31N9O4 | 545.593 | 10 | 6 |
| 121 | (Z)-5-((2-((2-(diethylamino)ethyl)(methyl)amino)-6-(furan-2-ylmethoxy)pyrimidin-4-yl)methylene)imidazolidine-2,4-dione | C20H26N6O4 | 414.458 | 11 | 6 |
| 122 | (Z)-N-(2-((4-((2,4-dioxoimidazolidin-5-ylidene)methyl)-6-(furan-2-ylmethoxy)pyrimidin-2-yl)amino)ethyl)isoquinoline-5-sulfonamide | C24H21N7O6S | 535.532 | 12 | 6 |

TABLE 3-continued

Additional prophetic embodiments of the invention.

| No | Chemical Name | Formula | Mol Weight | Reactant A | Reactant B |
|---|---|---|---|---|---|
| 123 | (Z)-N-(2-((4-((2,4-dioxoimidazolidin-5-ylidene)methyl)-6-(furan-2-ylmethoxy)pyrimidin-2-yl)amino)ethyl)benzamide | C22H20N6O5 | 448.431 | 13 | 6 |
| 124 | (Z)-5-((6-(furan-2-ylmethoxy)-2-((2-(4-oxo-3,4-dihydroquinazolin-2-yl)ethyl)amino)pyrimidin-4-yl)methylene)imidazolidine-2,4-dione | C23H19N7O5 | 473.441 | 14 | 6 |
| 125 | (Z)-5-((2-(4-benzoylpiperazin-1-yl)-6-(furan-2-ylmethoxy)pyrimidin-4-yl)methylene)imidazolidine-2,4-dione | C24H22N6O5 | 474.469 | 15 | 6 |
| 126 | (Z)-5-((6-(furan-2-ylmethoxy)-2-(4-(phenylsulfonyl)piperazin-1-yl)pyrimidin-4-yl)methylene)imidazolidine-2,4-dione | C23H22N6O6S | 510.522 | 16 | 6 |
| 127 | (Z)-5-((2-(5-benzoylhexahydropyrrolo[3,4-c]pyrrol-2(1H)-yl)-6-(furan-2-ylmethoxy)pyrimidin-4-yl)methylene)imidazolidine-2,4-dione | C26H24N6O5 | 500.506 | 17 | 6 |
| 128 | (Z)-5-((6-(furan-2-ylmethoxy)-2-(5-(phenylsulfonyl)hexahydropyrrolo[3,4-c]pyrrol-2(1H)-yl)pyrimidin-4-yl)methylene)imidazolidine-2,4-dione | C25H24N6O6S | 536.56 | 18 | 6 |
| 129 | (Z)-5-(4-((2,4-dioxoimidazolidin-5-ylidene)methyl)-6-(furan-2-ylmethoxy)pyrimidin-2-yl)-N-phenylhexahydropyrrolo[3,4-c]pyrrole-2(1H)-carboxamide | C26H25N7O5 | 515.521 | 19 | 6 |
| 130 | (Z)-6-(4-((2,4-dioxoimidazolidin-5-ylidene)methyl)-6-(furan-2-ylmethoxy)pyrimidin-2-yl)-N-phenyl-2,6-diazaspiro[3.3]heptane-2-carboxamide | C25H23N7O5 | 501.494 | 20 | 6 |
| 131 | (Z)-5-((2-(6-benzoyl-2,6-diazaspiro[3.3]heptan-2-yl)-6-(furan-2-ylmethoxy)pyrimidin-4-yl)methylene)imidazolidine-2,4-dione | C25H22N6O5 | 486.479 | 21 | 6 |
| 132 | (Z)-5-((6-(furan-2-ylmethoxy)-2-(6-(phenylsulfonyl)-2,6-diazaspiro[3.3]heptan-2-yl)pyrimidin-4-yl)methylene)imidazolidine-2,4-dione | C24H22N6O6S | 522.533 | 22 | 6 |
| 133 | (Z)-5-((6-phenoxy-2-(4-phenylpiperazin-1-yl)pyrimidin-4-yl)methylene)imidazolidine-2,4-dione | C24H22N6O3 | 442.47 | 1 | 7 |
| 134 | (Z)-5-((6-phenoxy-2-(4-(pyridin-3-yl)piperazin-1-yl)pyrimidin-4-yl)methylene)imidazolidine-2,4-dione | C23H21N7O3 | 443.458 | 2 | 7 |
| 135 | (Z)-5-((6-phenoxy-2-(4-(pyrimidin-5-yl)piperazin-1-yl)pyrimidin-4-yl)methylene)imidazolidine-2,4-dione | C22H20N8O3 | 444.446 | 3 | 7 |
| 136 | (Z)-5-((6-phenoxy-2-(4-(pyrimidin-2-yl)piperazin-1-yl)pyrimidin-4-yl)methylene)imidazolidine-2,4-dione | C22H20N8O3 | 444.446 | 4 | 7 |
| 137 | (Z)-4-(4-((2,4-dioxoimidazolidin-5-ylidene)methyl)-6-phenoxypyrimidin-2-yl)-N-phenylpiperazine-1-carboxamide | C25H23N7O4 | 485.495 | 5 | 7 |
| 138 | (Z)-5-((2-(4-(1-ethylpiperidin-4-yl)piperazin-1-yl)-6-phenoxypyrimidin-4-yl)methylene)imidazolidine-2,4-dione | C25H31N7O3 | 477.559 | 6 | 7 |
| 139 | (Z)-5-((6-phenoxy-2-(4-(pyridin-4-yl)-1,4-diazepan-1-yl)pyrimidin-4-yl)methylene)imidazolidine-2,4-dione | C24H23N7O3 | 457.485 | 7 | 7 |
| 140 | (Z)-5-((2-(4-(benzo[d]oxazol-2-yl)-1,4-diazepan-1-yl)-6-phenoxypyrimidin-4-yl)methylene)imidazolidine-2,4-dione | C26H23N7O4 | 497.505 | 8 | 7 |
| 141 | (Z)-4-(4-((2,4-dioxoimidazolidin-5-ylidene)methyl)-6-phenoxypyrimidin-2-yl)-N-phenyl-1,4-diazepane-1-carboxamide | C26H25N7O4 | 499.521 | 9 | 7 |
| 142 | (Z)-5-((2-(4-(6-methyl-2-(pyrrolidin-1-yl)pyrimidin-4-yl)-1,4-diazepan-1-yl)-6-phenoxypyrimidin-4-yl)methylene)imidazolidine-2,4-dione | C28H31N9O3 | 541.604 | 10 | 7 |
| 143 | (Z)-5-((2-((2-(diethylamino)ethyl)(methyl)amino)-6-phenoxypyrimidin-4-yl)methylene)imidazolidine-2,4-dione | C21H26N6O3 | 410.47 | 11 | 7 |

TABLE 3-continued

Additional prophetic embodiments of the invention.

| No | Chemical Name | Formula | Mol Weight | Reactant A | Reactant B |
|---|---|---|---|---|---|
| 144 | (Z)-N-(2-((4-((2,4-dioxoimidazolidin-5-ylidene)methyl)-6-phenoxypyrimidin-2-yl)amino)ethyl)isoquinoline-5-sulfonamide | C25H21N7O5S | 531.543 | 12 | 7 |
| 145 | (Z)-N-(2-((4-((2,4-dioxoimidazolidin-5-ylidene)methyl)-6-phenoxypyrimidin-2-yl)amino)ethyl)benzamide | C23H20N6O4 | 444.443 | 13 | 7 |
| 146 | (Z)-5-((2-((2-(4-oxo-3,4-dihydroquinazolin-2-yl)ethyl)amino)-6-phenoxypyrimidin-4-yl)methylene)imidazolidine-2,4-dione | C24H19N7O4 | 469.452 | 14 | 7 |
| 147 | (Z)-5-((2-(4-benzoylpiperazin-1-yl)-6-phenoxypyrimidin-4-yl)methylene)imidazolidine-2,4-dione | C25H22N6O4 | 470.48 | 15 | 7 |
| 148 | (Z)-5-((6-phenoxy-2-(4-(phenylsulfonyl)piperazin-1-yl)pyrimidin-4-yl)methylene)imidazolidine-2,4-dione | C24H22N6O5S | 506.534 | 16 | 7 |
| 149 | (Z)-5-((2-(5-benzoylhexahydropyrrolo[3,4-c]pyrrol-2(1H)-yl)-6-phenoxypyrimidin-4-yl)methylene)imidazolidine-2,4-dione | C27H24N6O4 | 496.517 | 17 | 7 |
| 150 | (Z)-5-((6-phenoxy-2-(5-(phenylsulfonyl)hexahydropyrrolo[3,4-c]pyrrol-2(1H)-yl)pyrimidin-4-yl)methylene)imidazolidine-2,4-dione | C26H24N6O5S | 532.571 | 18 | 7 |
| 151 | (Z)-5-(4-((2,4-dioxoimidazolidin-5-ylidene)methyl)-6-phenoxypyrimidin-2-yl)-N-phenylhexahydropyrrolo[3,4-c]pyrrole-2(1H)-carboxamide | C27H25N7O4 | 511.532 | 19 | 7 |
| 152 | (Z)-6-(4-((2,4-dioxoimidazolidin-5-ylidene)methyl)-6-phenoxypyrimidin-2-yl)-N-phenyl-2,6-diazaspiro[3.3]heptane-2-carboxamide | C26H23N7O4 | 497.505 | 20 | 7 |
| 153 | (Z)-5-((2-(6-benzoyl-2,6-diazaspiro[3.3]heptan-2-yl)-6-phenoxypyrimidin-4-yl)methylene)imidazolidine-2,4-dione | C26H22N6O4 | 482.491 | 21 | 7 |
| 154 | (Z)-5-((6-phenoxy-2-(6-(phenylsulfonyl)-2,6-diazaspiro[3.3]heptan-2-yl)pyrimidin-4-yl)methylene)imidazolidine-2,4-dione | C25H22N6O5S | 518.544 | 22 | 7 |
| 155 | (Z)-5-((6-(benzyloxy)-2-(4-phenylpiperazin-1-yl)pyrimidin-4-yl)methylene)imidazolidine-2,4-dione | C25H24N6O3 | 456.496 | 1 | 8 |
| 156 | (Z)-5-((6-(benzyloxy)-2-(4-(pyridin-3-yl)piperazin-1-yl)pyrimidin-4-yl)methylene)imidazolidine-2,4-dione | C24H23N7O3 | 457.485 | 2 | 8 |
| 157 | (Z)-5-((6-(benzyloxy)-2-(4-(pyrimidin-5-yl)piperazin-1-yl)pyrimidin-4-yl)methylene)imidazolidine-2,4-dione | C23H22N8O3 | 458.473 | 3 | 8 |
| 158 | (Z)-5-((6-(benzyloxy)-2-(4-(pyrimidin-2-yl)piperazin-1-yl)pyrimidin-4-yl)methylene)imidazolidine-2,4-dione | C23H22N8O3 | 458.473 | 4 | 8 |
| 159 | (Z)-4-(4-(benzyloxy)-6-((2,4-dioxoimidazolidin-5-ylidene)methyl)pyrimidin-2-yl)-N-phenylpiperazine-1-carboxamide | C26H25N7O4 | 499.521 | 5 | 8 |
| 160 | (Z)-5-((6-(benzyloxy)-2-(4-(1-ethylpiperidin-4-yl)piperazin-1-yl)pyrimidin-4-yl)methylene)imidazolidine-2,4-dione | C26H33N7O3 | 491.585 | 6 | 8 |
| 161 | (Z)-5-((6-(benzyloxy)-2-(4-(pyridin-4-yl)-1,4-diazepan-1-yl)pyrimidin-4-yl)methylene)imidazolidine-2,4-dione | C25H25N7O3 | 471.511 | 7 | 8 |
| 162 | (Z)-5-((2-(4-(benzo[d]oxazol-2-yl)-1,4-diazepan-1-yl)-6-(benzyloxy)pyrimidin-4-yl)methylene)imidazolidine-2,4-dione | C27H25N7O4 | 511.532 | 8 | 8 |
| 163 | (Z)-4-(4-(benzyloxy)-6-((2,4-dioxoimidazolidin-5-ylidene)methyl)pyrimidin-2-yl)-N-phenyl-1,4-diazepane-1-carboxamide | C27H27N7O4 | 513.548 | 9 | 8 |
| 164 | (Z)-5-((6-(benzyloxy)-2-(4-(6-methyl-2-(pyrrolidin-1-yl)pyrimidin-4-yl)-1,4-diazepan-1-yl)pyrimidin-4-yl)methylene)imidazolidine-2,4-dione | C29H33N9O3 | 555.631 | 10 | 8 |
| 165 | (Z)-5-((6-(benzyloxy)-2-((2-(diethylamino)ethyl)(methyl)amino)pyrimidin-4-yl)methylene)imidazolidine-2,4-dione | C22H28N6O3 | 424.496 | 11 | 8 |
| 166 | (Z)-N-(2-((4-(benzyloxy)-6-((2,4-dioxoimidazolidin-5-ylidene)methyl)pyrimidin-2-yl)amino)ethyl)isoquinoline-5-sulfonamide | C26H23N7O5S | 545.57 | 12 | 8 |

TABLE 3-continued

Additional prophetic embodiments of the invention.

| No | Chemical Name | Formula | Mol Weight | Reactant A | Reactant B |
|---|---|---|---|---|---|
| 167 | (Z)-N-(2-((4-(benzyloxy)-6-((2,4-dioxoimidazolidin-5-ylidene)methyl)pyrimidin-2-yl)amino)ethyl)benzamide | C24H22N6O4 | 458.469 | 13 | 8 |
| 168 | (Z)-5-((6-(benzyloxy)-2-((2-(4-oxo-3,4-dihydroquinazolin-2-yl)ethyl)amino)pyrimidin-4-yl)methylene)imidazolidine-2,4-dione | C25H21N7O4 | 483.479 | 14 | 8 |
| 169 | (Z)-5-((2-(4-benzoylpiperazin-1-yl)-6-(benzyloxy)pyrimidin-4-yl)methylene)imidazolidine-2,4-dione | C26H24N6O4 | 484.507 | 15 | 8 |
| 170 | (Z)-5-((6-(benzyloxy)-2-(4-(phenylsulfonyl)piperazin-1-yl)pyrimidin-4-yl)methylene)imidazolidine-2,4-dione | C25H24N6O5S | 520.56 | 16 | 8 |
| 171 | (Z)-5-((2-(5-benzoylhexahydropyrrolo[3,4-c]pyrrol-2(1H)-yl)-6-(benzyloxy)pyrimidin-4-yl)methylene)imidazolidine-2,4-dione | C28H26N6O4 | 510.544 | 17 | 8 |
| 172 | (Z)-5-((6-(benzyloxy)-2-(5-(phenylsulfonyl)hexahydropyrrolo[3,4-c]pyrrol-2(1H)-yl)pyrimidin-4-yl)methylene)imidazolidine-2,4-dione | C27H26N6O5S | 546.598 | 18 | 8 |
| 173 | (Z)-5-(4-(benzyloxy)-6-((2,4-dioxoimidazolidin-5-ylidene)methyl)pyrimidin-2-yl)-N-phenylhexahydropyrrolo[3,4-c]pyrrole-2(1H)-carboxamide | C28H27N7O4 | 525.558 | 19 | 8 |
| 174 | (Z)-6-(4-(benzyloxy)-6-((2,4-dioxoimidazolidin-5-ylidene)methyl)pyrimidin-2-yl)-N-phenyl-2,6-diazaspiro[3.3]heptane-2-carboxamide | C27H25N7O4 | 511.532 | 20 | 8 |
| 175 | (Z)-5-((2-(6-benzoyl-2,6-diazaspiro[3.3]heptan-2-yl)-6-(benzyloxy)pyrimidin-4-yl)methylene)imidazolidine-2,4-dione | C27H24N6O4 | 496.517 | 21 | 8 |
| 176 | (Z)-5-((6-(benzyloxy)-2-(6-(phenylsulfonyl)-2,6-diazaspiro[3.3]heptan-2-yl)pyrimidin-4-yl)methylene)imidazolidine-2,4-dione | C26H24N6O5S | 532.571 | 22 | 8 |
| 177 | (Z)-5-((6-(2-methoxyethoxy)-2-(4-phenylpiperazin-1-yl)pyrimidin-4-yl)methylene)imidazolidine-2,4-dione | C21H24N6O4 | 424.453 | 1 | 9 |
| 178 | (Z)-5-((6-(2-methoxyethoxy)-2-(4-(pyridin-3-yl)piperazin-1-yl)pyrimidin-4-yl)methylene)imidazolidine-2,4-dione | C20H23N7O4 | 425.441 | 2 | 9 |
| 179 | (Z)-5-((6-(2-methoxyethoxy)-2-(4-(pyrimidin-5-yl)piperazin-1-yl)pyrimidin-4-yl)methylene)imidazolidine-2,4-dione | C19H22N8O4 | 426.429 | 3 | 9 |
| 180 | (Z)-5-((6-(2-methoxyethoxy)-2-(4-(pyrimidin-2-yl)piperazin-1-yl)pyrimidin-4-yl)methylene)imidazolidine-2,4-dione | C19H22N8O4 | 426.429 | 4 | 9 |
| 181 | (Z)-4-(4-((2,4-dioxoimidazolidin-5-ylidene)methyl)-6-(2-methoxyethoxy)pyrimidin-2-yl)-N-phenylpiperazine-1-carboxamide | C22H25N7O5 | 467.478 | 5 | 9 |
| 182 | (Z)-5-((2-(4-(1-ethylpiperidin-4-yl)piperazin-1-yl)-6-(2-methoxyethoxy)pyrimidin-4-yl)methylene)imidazolidine-2,4-dione | C22H33N7O4 | 459.542 | 6 | 9 |
| 183 | (Z)-5-((6-(2-methoxyethoxy)-2-(4-(pyridin-4-yl)-1,4-diazepan-1-yl)pyrimidin-4-yl)methylene)imidazolidine-2,4-dione | C21H25N7O4 | 439.468 | 7 | 9 |
| 184 | (Z)-5-((2-(4-(benzo[d]oxazol-2-yl)-1,4-diazepan-1-yl)-6-(2-methoxyethoxy)pyrimidin-4-yl)methylene)imidazolidine-2,4-dione | C23H25N7O5 | 479.489 | 8 | 9 |
| 185 | (Z)-4-(4-((2,4-dioxoimidazolidin-5-ylidene)methyl)-6-(2-methoxyethoxy)pyrimidin-2-yl)-N-phenyl-1,4-diazepane-1-carboxamide | C23H27N7O5 | 481.504 | 9 | 9 |
| 186 | (Z)-5-((6-(2-methoxyethoxy)-2-(4-(6-methyl-2-(pyrrolidin-1-yl)pyrimidin-4-yl)-1,4-diazepan-1-yl)pyrimidin-4-yl)methylene)imidazolidine-2,4-dione | C25H33N9O4 | 523.587 | 10 | 9 |
| 187 | (Z)-5-((2-((2-(diethylamino)ethyl)(methyl)amino)-6-(2-methoxyethoxy)pyrimidin-4-yl)methylene)imidazolidine-2,4-dione | C18H28N6O4 | 392.453 | 11 | 9 |
| 188 | (Z)-N-(2-((4-((2,4-dioxoimidazolidin-5-ylidene)methyl)-6-(2-methoxyethoxy)pyrimidin-2-yl)amino)ethyl)isoquinoline-5-sulfonamide | C22H23N7O6S | 513.526 | 12 | 9 |
| 189 | (Z)-N-(2-((4-((2,4-dioxoimidazolidin-5-ylidene)methyl)-6-(2-methoxyethoxy)pyrimidin-2-yl)amino)ethyl)benzamide | C20H22N6O5 | 426.426 | 13 | 9 |

TABLE 3-continued

Additional prophetic embodiments of the invention.

| No | Chemical Name | Formula | Mol Weight | Reactant A | Reactant B |
|---|---|---|---|---|---|
| 190 | (Z)-5-((6-(2-methoxyethoxy)-2-((2-(4-oxo-3,4-dihydroquinazolin-2-yl)ethyl)amino)pyrimidin-4-yl)methylene)imidazolidine-2,4-dione | C21H21N7O5 | 451.435 | 14 | 9 |
| 191 | (Z)-5-((2-(4-benzoylpiperazin-1-yl)-6-(2-methoxyethoxy)pyrimidin-4-yl)methylene)imidazolidine-2,4-dione | C22H24N6O5 | 452.463 | 15 | 9 |
| 192 | (Z)-5-((6-(2-methoxyethoxy)-2-(4-(phenylsulfonyl)piperazin-1-yl)pyrimidin-4-yl)methylene)imidazolidine-2,4-dione | C21H24N6O6S | 488.517 | 16 | 9 |
| 193 | (Z)-5-((2-(5-benzoylhexahydropyrrolo[3,4-c]pyrrol-2(1H)-yl)-6-(2-methoxyethoxy)pyrimidin-4-yl)methylene)imidazolidine-2,4-dione | C24H26N6O5 | 478.5 | 17 | 9 |
| 194 | (Z)-5-((6-(2-methoxyethoxy)-2-(5-(phenylsulfonyl)hexahydropyrrolo[3,4-c]pyrrol-2(1H)-yl)pyrimidin-4-yl)methylene)imidazolidine-2,4-dione | C23H26N6O6S | 514.554 | 18 | 9 |
| 195 | (Z)-5-(4-((2,4-dioxoimidazolidin-5-ylidene)methyl)-6-(2-methoxyethoxy)pyrimidin-2-yl)-N-phenylhexahydropyrrolo[3,4-c]pyrrole-2(1H)-carboxamide | C24H27N7O5 | 493.515 | 19 | 9 |
| 196 | (Z)-6-(4-((2,4-dioxoimidazolidin-5-ylidene)methyl)-6-(2-methoxyethoxy)pyrimidin-2-yl)-N-phenyl-2,6-diazaspiro[3.3]heptane-2-carboxamide | C23H25N7O5 | 479.489 | 20 | 9 |
| 197 | (Z)-5-((2-(6-benzoyl-2,6-diazaspiro[3.3]heptan-2-yl)-6-(2-methoxyethoxy)pyrimidin-4-yl)methylene)imidazolidine-2,4-dione | C23H24N6O5 | 464.474 | 21 | 9 |
| 198 | (Z)-5-((6-(2-methoxyethoxy)-2-(6-(phenylsulfonyl)-2,6-diazaspiro[3.3]heptan-2-yl)pyrimidin-4-yl)methylene)imidazolidine-2,4-dione | C22H24N6O6S | 500.528 | 22 | 9 |
| 199 | (Z)-5-((6-(2-(dimethylamino)ethoxy)-2-(4-phenylpiperazin-1-yl)pyrimidin-4-yl)methylene)imidazolidine-2,4-dione | C22H27N7O3 | 437.495 | 1 | 10 |
| 200 | (Z)-5-((6-(2-(dimethylamino)ethoxy)-2-(4-(pyridin-3-yl)piperazin-1-yl)pyrimidin-4-yl)methylene)imidazolidine-2,4-dione | C21H26N8O3 | 438.483 | 2 | 10 |
| 201 | (Z)-5-((6-(2-(dimethylamino)ethoxy)-2-(4-(pyrimidin-5-yl)piperazin-1-yl)pyrimidin-4-yl)methylene)imidazolidine-2,4-dione | C20H25N9O3 | 439.471 | 3 | 10 |
| 202 | (Z)-5-((6-(2-(dimethylamino)ethoxy)-2-(4-(pyrimidin-2-yl)piperazin-1-yl)pyrimidin-4-yl)methylene)imidazolidine-2,4-dione | C20H25N9O3 | 439.471 | 4 | 10 |
| 203 | (Z)-4-(4-(2-(dimethylamino)ethoxy)-6-((2,4-dioxoimidazolidin-5-ylidene)methyl)pyrimidin-2-yl)-N-phenylpiperazine-1-carboxamide | C23H28N8O4 | 480.52 | 5 | 10 |
| 204 | (Z)-5-((6-(2-(dimethylamino)ethoxy)-2-(4-(1-ethylpiperidin-4-yl)piperazin-1-yl)pyrimidin-4-yl)methylene)imidazolidine-2,4-dione | C23H36N8O3 | 472.584 | 6 | 10 |
| 205 | (Z)-5-((6-(2-(dimethylamino)ethoxy)-2-(4-(pyridin-4-yl)-1,4-diazepan-1-yl)pyrimidin-4-yl)methylene)imidazolidine-2,4-dione | C22H28N8O3 | 452.51 | 7 | 10 |
| 206 | (Z)-5-((2-(4-(benzo[d]oxazol-2-yl)-1,4-diazepan-1-yl)-6-(2-(dimethylamino)ethoxy)pyrimidin-4-yl)methylene)imidazolidine-2,4-dione | C24H28N8O4 | 492.53 | 8 | 10 |
| 207 | (Z)-4-(4-(2-(dimethylamino)ethoxy)-6-((2,4-dioxoimidazolidin-5-ylidene)methyl)pyrimidin-2-yl)-N-phenyl-1,4-diazepane-1-carboxamide | C24H30N8O4 | 494.546 | 9 | 10 |
| 208 | (Z)-5-((6-(2-(dimethylamino)ethoxy)-2-(4-(6-methyl-2-(pyrrolidin-1-yl)pyrimidin-4-yl)-1,4-diazepan-1-yl)pyrimidin-4-yl)methylene)imidazolidine-2,4-dione | C26H36N10O3 | 536.629 | 10 | 10 |
| 209 | (Z)-5-((2-((2-(diethylamino)ethyl)(methyl)amino)-6-(2-(dimethylamino)ethoxy)pyrimidin-4-yl)methylene)imidazolidine-2,4-dione | C19H31N7O3 | 405.495 | 11 | 10 |
| 210 | (Z)-N-(2-((4-(2-(dimethylamino)ethoxy)-6-((2,4-dioxoimidazolidin-5-ylidene)methyl)pyrimidin-2-yl)amino)ethyl)isoquinoline-5-sulfonamide | C23H26N8O5S | 526.568 | 12 | 10 |
| 211 | (Z)-N-(2-((4-(2-(dimethylamino)ethoxy)-6-((2,4-dioxoimidazolidin-5-ylidene)methyl)pyrimidin-2-yl)amino)ethyl)benzamide | C21H25N7O4 | 439.468 | 13 | 10 |

TABLE 3-continued

Additional prophetic embodiments of the invention.

| No | Chemical Name | Formula | Mol Weight | Reactant A | Reactant B |
|---|---|---|---|---|---|
| 212 | (Z)-5-((6-(2-(dimethylamino)ethoxy)-2-((2-(4-oxo-3,4-dihydroquinazolin-2-yl)ethyl)amino)pyrimidin-4-yl)methylene)imidazolidine-2,4-dione | C22H24N8O4 | 464.477 | 14 | 10 |
| 213 | (Z)-5-((2-(4-benzoylpiperazin-1-yl)-6-(2-(dimethylamino)ethoxy)pyrimidin-4-yl)methylene)imidazolidine-2,4-dione | C23H27N7O4 | 465.505 | 15 | 10 |
| 214 | (Z)-5-((6-(2-(dimethylamino)ethoxy)-2-(4-(phenylsulfonyl)piperazin-1-yl)pyrimidin-4-yl)methylene)imidazolidine-2,4-dione | C22H27N7O5S | 501.559 | 16 | 10 |
| 215 | (Z)-5-((2-(5-benzoylhexahydropyrrolo[3,4-c]pyrrol-2(1H)-yl)-6-(2-(dimethylamino)ethoxy)pyrimidin-4-yl)methylene)imidazolidine-2,4-dione | C25H29N7O4 | 491.542 | 17 | 10 |
| 216 | (Z)-5-((6-(2-(dimethylamino)ethoxy)-2-(5-(phenylsulfonyl)hexahydropyrrolo[3,4-c]pyrrol-2(1H)-yl)pyrimidin-4-yl)methylene)imidazolidine-2,4-dione | C24H29N7O5S | 527.596 | 18 | 10 |
| 217 | (Z)-5-(4-(2-(dimethylamino)ethoxy)-6-((2,4-dioxoimidazolidin-5-ylidene)methyl)pyrimidin-2-yl)-N-phenylhexahydropyrrolo[3,4-c]pyrrole-2(1H)-carboxamide | C25H30N8O4 | 506.557 | 19 | 10 |
| 218 | (Z)-6-(4-(2-(dimethylamino)ethoxy)-6-((2,4-dioxoimidazolidin-5-ylidene)methyl)pyrimidin-2-yl)-N-phenyl-2,6-diazaspiro[3.3]heptane-2-carboxamide | C24H28N8O4 | 492.53 | 20 | 10 |
| 219 | (Z)-5-((2-(6-benzoyl-2,6-diazaspiro[3.3]heptan-2-yl)-6-(2-(dimethylamino)ethoxy)pyrimidin-4-yl)methylene)imidazolidine-2,4-dione | C24H27N7O4 | 477.516 | 21 | 10 |
| 220 | (Z)-5-((6-(2-(dimethylamino)ethoxy)-2-(6-(phenylsulfonyl)-2,6-diazaspiro[3.3]heptan-2-yl)pyrimidin-4-yl)methylene)imidazolidine-2,4-dione | C23H27N7O5S | 513.569 | 22 | 10 |
| 221 | (Z)-5-((4-(4-phenylpiperazin-1-yl)pyrimidin-2-yl)methylene)imidazolidine-2,4-dione | C18H18N6O2 | 350.375 | 1 | 11 |
| 222 | (Z)-5-((4-(4-(pyridin-3-yl)piperazin-1-yl)pyrimidin-2-yl)methylene)imidazolidine-2,4-dione | C17H17N7O2 | 351.363 | 2 | 11 |
| 223 | (Z)-5-((4-(4-(pyrimidin-5-yl)piperazin-1-yl)pyrimidin-2-yl)methylene)imidazolidine-2,4-dione | C16H16N8O2 | 352.351 | 3 | 11 |
| 224 | (Z)-5-((4-(4-(pyrimidin-2-yl)piperazin-1-yl)pyrimidin-2-yl)methylene)imidazolidine-2,4-dione | C16H16N8O2 | 352.351 | 4 | 11 |
| 225 | (Z)-4-(2-((2,4-dioxoimidazolidin-5-ylidene)methyl)pyrimidin-4-yl)-N-phenylpiperazine-1-carboxamide | C19H19N7O3 | 393.399 | 5 | 11 |
| 226 | (Z)-5-((4-(4-(1-ethylpiperidin-4-yl)piperazin-1-yl)pyrimidin-2-yl)methylene)imidazolidine-2,4-dione | C19H27N7O2 | 385.463 | 6 | 11 |
| 227 | (Z)-5-((4-(4-(pyridin-4-yl)-1,4-diazepan-1-yl)pyrimidin-2-yl)methylene)imidazolidine-2,4-dione | C18H19N7O2 | 365.389 | 7 | 11 |
| 228 | (Z)-5-((4-(4-(benzo[d]oxazol-2-yl)-1,4-diazepan-1-yl)pyrimidin-2-yl)methylene)imidazolidine-2,4-dione | C20H19N7O3 | 405.41 | 8 | 11 |
| 229 | (Z)-4-(2-((2,4-dioxoimidazolidin-5-ylidene)methyl)pyrimidin-4-yl)-N-phenyl-1,4-diazepane-1-carboxamide | C20H21N7O3 | 407.426 | 9 | 11 |
| 230 | (Z)-5-((4-(4-(6-methyl-2-(pyrrolidin-1-yl)pyrimidin-4-yl)-1,4-diazepan-1-yl)pyrimidin-2-yl)methylene)imidazolidine-2,4-dione | C22H27N9O2 | 449.509 | 10 | 11 |
| 231 | (Z)-5-((4-((2-(diethylamino)ethyl)(methyl)amino)pyrimidin-2-yl)methylene)imidazolidine-2,4-dione | C15H22N6O2 | 318.374 | 11 | 11 |
| 232 | (Z)-N-(2-((2-((2,4-dioxoimidazolidin-5-ylidene)methyl)pyrimidin-4-yl)amino)ethyl)isoquinoline-5-sulfonamide | C19H17N7O4S | 439.448 | 12 | 11 |
| 233 | (Z)-N-(2-((2-((2,4-dioxoimidazolidin-5-ylidene)methyl)pyrimidin-4-yl)amino)ethyl)benzamide | C17H16N6O3 | 352.347 | 13 | 11 |
| 234 | (Z)-5-((4-((2-(4-oxo-3,4-dihydroquinazolin-2-yl)ethyl)amino)pyrimidin-2-yl)methylene)imidazolidine-2,4-dione | C18H15N7O3 | 377.357 | 14 | 11 |

TABLE 3-continued

Additional prophetic embodiments of the invention.

| No | Chemical Name | Formula | Mol Weight | Reactant A | Reactant B |
|---|---|---|---|---|---|
| 235 | (Z)-5-((4-(4-benzoylpiperazin-1-yl)pyrimidin-2-yl)methylene)imidazolidine-2,4-dione | C19H18N6O3 | 378.385 | 15 | 11 |
| 236 | (Z)-5-((4-(4-(phenylsulfonyl)piperazin-1-yl)pyrimidin-2-yl)methylene)imidazolidine-2,4-dione | C18H18N6O4S | 414.438 | 16 | 11 |
| 237 | (Z)-5-((4-(5-benzoylhexahydropyrrolo[3,4-c]pyrrol-2(1H)-yl)pyrimidin-2-yl)methylene)imidazolidine-2,4-dione | C21H20N6O3 | 404.422 | 17 | 11 |
| 238 | (Z)-5-((4-(5-(phenylsulfonyl)hexahydropyrrolo[3,4-c]pyrrol-2(1H)-yl)pyrimidin-2-yl)methylene)imidazolidine-2,4-dione | C20H20N6O4S | 440.476 | 18 | 11 |
| 239 | (Z)-5-(2-((2,4-dioxoimidazolidin-5-ylidene)methyl)pyrimidin-4-yl)-N-phenylhexahydropyrrolo[3,4-c]pyrrole-2(1H)-carboxamide | C21H21N7O3 | 419.437 | 19 | 11 |
| 240 | (Z)-6-(2-((2,4-dioxoimidazolidin-5-ylidene)methyl)pyrimidin-4-yl)-N-phenyl-2,6-diazaspiro[3.3]heptane-2-carboxamide | C20H19N7O3 | 405.41 | 20 | 11 |
| 241 | (Z)-5-((4-(6-benzoyl-2,6-diazaspiro[3.3]heptan-2-yl)pyrimidin-2-yl)methylene)imidazolidine-2,4-dione | C20H18N6O3 | 390.395 | 21 | 11 |
| 242 | (Z)-5-((4-(6-(phenylsulfonyl)-2,6-diazaspiro[3.3]heptan-2-yl)pyrimidin-2-yl)methylene)imidazolidine-2,4-dione | C19H18N6O4S | 426.449 | 22 | 11 |
| 243 | (Z)-5-((4-(4-phenylpiperazin-1-yl)-1,3,5-triazin-2-yl)methylene)imidazolidine-2,4-dione | C17H17N7O2 | 351.363 | 1 | 12 |
| 244 | (Z)-5-((4-(4-(pyridin-3-yl)piperazin-1-yl)-1,3,5-triazin-2-yl)methylene)imidazolidine-2,4-dione | C16H16N8O2 | 352.351 | 2 | 12 |
| 245 | (Z)-5-((4-(4-(pyrimidin-5-yl)piperazin-1-yl)-1,3,5-triazin-2-yl)methylene)imidazolidine-2,4-dione | C15H15N9O2 | 353.339 | 3 | 12 |
| 246 | (Z)-5-((4-(4-(pyrimidin-2-yl)piperazin-1-yl)-1,3,5-triazin-2-yl)methylene)imidazolidine-2,4-dione | C15H15N9O2 | 353.339 | 4 | 12 |
| 247 | (Z)-4-(4-((2,4-dioxoimidazolidin-5-ylidene)methyl)-1,3,5-triazin-2-yl)-N-phenylpiperazine-1-carboxamide | C18H18N8O3 | 394.387 | 5 | 12 |
| 248 | (Z)-5-((4-(4-(1-ethylpiperidin-4-yl)piperazin-1-yl)-1,3,5-triazin-2-yl)methylene)imidazolidine-2,4-dione | C18H26N8O2 | 386.451 | 6 | 12 |
| 249 | (Z)-5-((4-(4-(pyridin-4-yl)-1,4-diazepan-1-yl)-1,3,5-triazin-2-yl)methylene)imidazolidine-2,4-dione | C17H18N8O2 | 366.377 | 7 | 12 |
| 250 | (Z)-5-((4-(4-(benzo[d]oxazol-2-yl)-1,4-diazepan-1-yl)-1,3,5-triazin-2-yl)methylene)imidazolidine-2,4-dione | C19H18N8O3 | 406.398 | 8 | 12 |
| 251 | (Z)-4-(4-((2,4-dioxoimidazolidin-5-ylidene)methyl)-1,3,5-triazin-2-yl)-N-phenyl-1,4-diazepane-1-carboxamide | C19H20N8O3 | 408.414 | 9 | 12 |
| 252 | (Z)-5-((4-(4-(6-methyl-2-(pyrrolidin-1-yl)pyrimidin-4-yl)-1,4-diazepan-1-yl)-1,3,5-triazin-2-yl)methylene)imidazolidine-2,4-dione | C21H26N10O2 | 450.497 | 10 | 12 |
| 253 | (Z)-5-((4-((2-(diethylamino)ethyl)(methyl)amino)-1,3,5-triazin-2-yl)methylene)imidazolidine-2,4-dione | C14H21N7O2 | 319.362 | 11 | 12 |
| 254 | (Z)-N-(2-((4-((2,4-dioxoimidazolidin-5-ylidene)methyl)-1,3,5-triazin-2-yl)amino)ethyl)isoquinoline-5-sulfonamide | C18H16N8O4S | 440.436 | 12 | 12 |
| 255 | (Z)-N-(2-((4-((2,4-dioxoimidazolidin-5-ylidene)methyl)-1,3,5-triazin-2-yl)amino)ethyl)benzamide | C16H15N7O3 | 353.335 | 13 | 12 |
| 256 | (Z)-5-((4-((2-(4-oxo-3,4-dihydroquinazolin-2-yl)ethyl)amino)-1,3,5-triazin-2-yl)methylene)imidazolidine-2,4-dione | C17H14N8O3 | 378.345 | 14 | 12 |
| 257 | (Z)-5-((4-(4-benzoylpiperazin-1-yl)-1,3,5-triazin-2-yl)methylene)imidazolidine-2,4-dione | C18H17N7O3 | 379.373 | 15 | 12 |
| 258 | (Z)-5-((4-(4-(phenylsulfonyl)piperazin-1-yl)-1,3,5-triazin-2-yl)methylene)imidazolidine-2,4-dione | C17H17N7O4S | 415.426 | 16 | 12 |
| 259 | (Z)-5-((4-(5-benzoylhexahydropyrrolo[3,4-c]pyrrol-2(1H)-yl)-1,3,5-triazin-2-yl)methylene)imidazolidine-2,4-dione | C20H19N7O3 | 405.41 | 17 | 12 |

TABLE 3-continued

Additional prophetic embodiments of the invention.

| No | Chemical Name | Formula | Mol Weight | Reactant A | Reactant B |
|---|---|---|---|---|---|
| 260 | (Z)-5-((4-(5-(phenylsulfonyl)hexahydropyrrolo[3,4-c]pyrrol-2(1H)-yl)-1,3,5-triazin-2-yl)methylene)imidazolidine-2,4-dione | C19H19N7O4S | 441.464 | 18 | 12 |
| 261 | (Z)-5-(4-((2,4-dioxoimidazolidin-5-ylidene)methyl)-1,3,5-triazin-2-yl)-N-phenylhexahydropyrrolo[3,4-c]pyrrole-2(1H)-carboxamide | C20H20N8O3 | 420.425 | 19 | 12 |
| 262 | (Z)-6-(4-((2,4-dioxoimidazolidin-5-ylidene)methyl)-1,3,5-triazin-2-yl)-N-phenyl-2,6-diazaspiro[3.3]heptane-2-carboxamide | C19H18N8O3 | 406.398 | 20 | 12 |
| 263 | (Z)-5-((4-(6-benzoyl-2,6-diazaspiro[3.3]heptan-2-yl)-1,3,5-triazin-2-yl)methylene)imidazolidine-2,4-dione | C19H17N7O3 | 391.383 | 21 | 12 |
| 264 | (Z)-5-((4-(6-(phenylsulfonyl)-2,6-diazaspiro[3.3]heptan-2-yl)-1,3,5-triazin-2-yl)methylene)imidazolidine-2,4-dione | C18H17N7O4S | 427.437 | 22 | 12 |

In addition, it may be convenient or desirable to prepare, purify, and/or handle the active compound in a chemically protected form. The term "chemically protected form," as used herein, pertains to a compound in which one or more reactive functional groups are protected from undesirable chemical reactions (i.e., they have been modified with a protecting group).

By protecting a reactive functional group, reactions involving other unprotected reactive functional groups can be performed without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(═O)R), for example, as: a t-butyl ether; a benzyl, benzhydryl (diphenylmethyl), or trityl(triphenylmethyl)ether; a trimethylsilyl or t-butyldimethylsilyl ether; or an acetyl ester (—OC(═O)CH$_3$, —OAc).

For example, an aldehyde or ketone group may be protected as an acetal or ketal, respectively, in which the carbonyl group (C(═O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(═O)R) or a urethane (—NRC(═O)OR), for example, as: a methyl amide (—NHC(═O)CH$_3$); a benzyloxy amide (—NHC(═O)OCH$_2$C$_6$H$_5$NHCbz); as a t-butoxy amide (—NHC(═O)OC(CH$_3$)$_3$, —NHBoc); a 2-biphenyl-2-propoxy amide (—NHC(═O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—SCH$_2$NHC(═O)CH$_3$).

Pharmaceutical Compositions

One or more compounds of this invention can be administered to a mammal by themselves or in pharmaceutical compositions where they are mixed with suitable carriers or excipient(s) at doses to treat or ameliorate a disease or condition as described herein. Mixtures of these compounds can also be administered to the patient as a simple mixture or in suitable formulated pharmaceutical compositions. For example, one aspect of the invention relates to pharmaceutical composition comprising a therapeutically effective dose of a compound of formula I, or a pharmaceutically acceptable salt, solvate, enantiomer or stereoisomer thereof; and a pharmaceutically acceptable diluent or carrier.

Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer a compound in a local rather than a systemic manner, for example, via injection of the compound directly into an edematous site, often in a depot or sustained release formulation.

Furthermore, one may administer a compound in a targeted drug delivery system, for example, in a liposome coated with endothelial-cell-specific antibody.

The pharmaceutical compositions of the present invention may be manufactured, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants are used in the formulation appropriate to the barrier to be permeated. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for reconstitution before use with a suitable vehicle, e.g., sterile pyrogen-free water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example, subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives (for example, as a sparingly soluble salt).

Alternatively, other delivery systems for hydrophobic pharmaceutical compounds may be employed. Liposomes and emulsions are examples of delivery vehicles or carriers for hydrophobic drugs. Certain organic solvents such as dimethylsulfoxide also may be employed. Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions may also comprise suitable solid or gel phase carriers or excipients. Examples of such carriers or excipients include but are not limited to calcium carbonate, calcium phosphate, various sugars, starches, cellulose derivatives, gelatin, and polymers, such as polyethylene glycols.

Methods of Treatment

Provided herein are methods of modulating the activity of CK1 and subtypes thereof, the Wnt pathway, and/or the TGFβ pathway. Also provided herein are methods of treating or preventing conditions and diseases the course of which can be influenced by modulating the activity of CK1 (e.g., CK1γ), the Wnt pathway, and/or the TGFβ pathway. Such methods typically comprise administering to a subject in need thereof a therapeutically effective amount of a compound or composition of the invention.

Various diseases, such as cancers, inflammation, and inflammatory diseases (e.g., osteoarthritis and rheumatoid arthritis), and neurological conditions (e.g., Alzheimer's disease) and neurodegeneration can be treated by administration of modulators of CK1 (e.g., CK1γ), the Wnt pathway and/or the TGFβ pathway. Bone-related diseases and conditions, including osteoporosis and bone formation, also can be treated by administration of modulators of CK1 (e.g., CK1γ), the Wnt pathway and/or the TGF pathway. Bone restoration can be facilitated by administration of modulators of CK1 (e.g., CK1γ), the Wnt pathway and/or the TGFβ pathway. Additional conditions that can be treated by administration of modulators of CK1 (e.g., CK1γ), the Wnt pathway and/or the TGFβ pathway include hypoglycemia, metabolic syndrome and diabetes. Modulators of CK1 (e.g., CK1γ), the Wnt pathway and/or the TGFβ pathway are also useful for influencing apoptosis (e.g., increasing the rate of apoptosis in cancerous cells). Modulators of CK1 (e.g., CK1γ), the Wnt pathway and/or the TGFβ pathway are also useful in treatment or prevention of aberrant embryonic development.

Based at least on the fact that increased CK1γ has been found to be associated with certain cancers, a method for treating cancer in a subject comprises administering to the subject in need thereof a therapeutically effective amount of a compound that inhibits CK1γ.

CK1γ inhibiting compounds can be used for modulating cell proliferation, generally. Accordingly, diseases that may be treated include hyperproliferative diseases, such as benign cell growth and malignant cell growth.

Exemplary cancers that may be treated include leukemias, e.g., acute lymphoid leukemia and myeloid leukemia, and carcinomas, such as colorectal carcinoma and hepatocarcinoma. Other cancers include Acute Lymphoblastic Leukemia; Acute Lymphoblastic Leukemia; Acute Myeloid Leukemia; Acute Myeloid Leukemia; Adrenocortical Carcinoma Adrenocortical Carcinoma; AIDS-Related Cancers; AIDS-Related Lymphoma; Anal Cancer; Astrocytoma, Childhood Cerebellar; Astrocytoma, Childhood Cerebral; Basal Cell Carcinoma, see Skin Cancer (non-Melanoma); Bile Duct Cancer, Extrahepatic; Bladder Cancer; Bladder Cancer; Bone Cancer, osteosarcoma/Malignant Fibrous Histiocytoma; Brain Stem Glioma; Brain Tumor; Brain Tumor, Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Brain Tumor; Breast Cancer; Breast Cancer and Pregnancy; Breast Cancer; Breast Cancer, Male; Bronchial Adenomas/Carcinoids; Burkitt's Lymphoma; Carcinoid Tumor; Carcinoid Tumor, Gastrointestinal; Carcinoma of Unknown Primary; Central Nervous System Lymphoma, Primary; Cerebellar Astrocytoma; Cerebral Astrocytoma/Malignant Glioma; Cervical Cancer; Childhood Cancers; Chronic Lymphocytic Leukemia; Chronic Myelogenous Leukemia; Chronic Myeloproliferative Disorders; Colon Cancer; Colorectal Cancer; Cutaneous T-Cell Lymphoma, see Mycosis Fungoides and Sezary Syndrome; Endometrial Cancer; Ependymoma; Esophageal Cancer; Esophageal Cancer; Ewing's Family of Tumors; Extracranial Germ Cell Tumor; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer; Gastrointestinal Carcinoid Tumor; Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hematologic (Blood) Cancer; Hepatocellular (Liver) Cancer, Adult (Primary); Hepatocellular (Liver) Cancer, Childhood (Primary); Hodgkin's Lymphoma; Hodgkin's Lymphoma; Hodgkin's Lymphoma During Pregnancy; Hypopharyngeal Cancer; Hypothalamic and Visual Pathway Glioma; Intraocular Melanoma; Islet Cell Carcinoma (Endocrine Pancreas); Kaposi's Sarcoma; Kidney (Renal Cell) Cancer; Kidney Cancer; Laryngeal Cancer; Laryngeal Cancer; Leukemia, Acute Lymphoblastic; Leukemia, Acute Lymphoblastic; Leukemia, Acute Myeloid; Leukemia, Acute Myeloid; Leukemia, Chronic Lymphocytic; Leukemia; Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt's; Lymphoma, Cutaneous T-Cell, see Mycosis Fungoides and Sezary Syndrome; Lymphoma, Hodgkin's; Lymphoma, Hodgkin's; Lymphoma, Hodgkin's During Pregnancy; Lymphoma, Non-Hodgkin's; Lymphoma, Non-Hodgkin's; Lymphoma, Non-Hodgkin's During Pregnancy; Lymphoma, Primary Central Nervous System; Macroglobulinemia, Waldenstrom's; Malignant Fibrous Histiocytoma of Bone/Osteosarcoma; Medulloblastoma; Melanoma; Melanoma, Intraocular (Eye); Merkel Cell Carcinoma; Mesothelioma, Adult Malignant; Mesothelioma; Metastatic Squamous Neck Cancer with Occult Primary; Multiple Endocrine Neoplasia Syndrome; Multiple Myeloma/Plasma Cell Neoplasm Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer; Neuroblastoma; Non-Hodgkin's Lymphoma; Non-Hodgkin's Lymphoma; Non-Hodgkin's Lymphoma During Pregnancy; Non-Small Cell Lung Cancer; Oral Cancer; Oral Cavity Cancer, Lip and; Oropharyngeal Cancer; Osteosarcoma/Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer; Pancreatic Cancer, Islet Cell; Paranasal Sinus and Nasal Cavity Cancer; Parathyroid Cancer; Penile Cancer; Pheochromocytoma; Pineoblastoma and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Prostate Cancer; Rectal Cancer; Renal Cell (Kidney) Cancer; Renal Cell (Kidney) Cancer; Renal Pelvis and Ureter, Transitional Cell Cancer; Retinoblastoma; Rhabdomyosarcoma; Salivary Gland Cancer; Salivary Gland Cancer; Sarcoma, Ewing's Family of Tumors; Sarcoma, Kaposi's; Sarcoma, Soft Tissue; Sarcoma, Soft Tissue; Sarcoma, Uterine; Sezary Syndrome; Skin Cancer (non-Melanoma); Skin Cancer; Skin Cancer (Melanoma); Skin Carcinoma, Merkel Cell; Small Cell Lung Cancer; Small Intestine Cancer; Soft Tissue Sarcoma; Soft Tissue Sarcoma; Squamous Cell Carcinoma, see Skin Cancer (non-Melanoma); Squamous Neck Cancer with Occult Primary, Metastatic; Stomach (Gastric) Cancer; Stomach (Gastric) Cancer; Supratentorial Primitive Neuroectodermal Tumors; T-Cell Lymphoma, Cutaneous, see Mycosis Fungoides and Sezary Syndrome; Testicular Cancer; Thymoma; Thymoma and Thymic Carcinoma; Thyroid Cancer; Thyroid Cancer; Transitional Cell Cancer of the Renal Pelvis and Ureter; Trophoblastic Tumor, Gestational; Unknown Primary Site, Carcinoma of; Unknown Primary Site, Cancer of; Unusual Cancers of Childhood; Ureter and Renal Pelvis, Transitional Cell Cancer; Urethral Cancer; Uterine Cancer, Endometrial; Uterine Sarcoma; Vaginal Cancer; Visual Pathway and Hypothalamic Glioma; Vulvar Cancer; Waldenstrom's Macroglobulinemia; Wilms' Tumor; and Women's Cancers.

Neurologic diseases that may be treated include epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA12).

Any other disease in which the Wnt pathway, TGFβ pathway, or CK1γ plays a role may be treatable or preventable using compounds and methods described herein.

Dosage

As used herein, a "therapeutically effective amount" or "therapeutically effective dose" is an amount of a compound of the invention or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount may be determined by methods known to those of skill in the art.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. In the treatment of crises, the administration of an acute bolus or an infusion approaching the MTD may be required to obtain a rapid response.

Dosage amount and interval may be adjusted individually to provide plasma levels of the active moiety which are sufficient to maintain the CK1γ modulating effects, or minimal effective concentration (MEC). The MEC will vary for each compound but can be estimated from in vitro data. Dosages necessary to achieve the MEC will depend on individual characteristics and route of administration. HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Kits

The compounds and compositions of the invention (e.g., compounds and compositions of formula I) may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Instructions for use may also be provided.

EXEMPLIFICATION

The invention now being generally described, it will be more readily understood by reference to the following examples, which are included merely for purposes of illustration of certain aspects and embodiments of the present invention, and are not intended to limit the invention. The geometric isomers depicted below are believed to be correct, but final structural assignment will be made via 2-D NMR experiments. Although the exemplary compounds described below are believed to be the Z-geometric isomers, the E-geometric isomers and mixtures of the E- and Z-isomers are also contemplated by the present disclosure.

Example 1

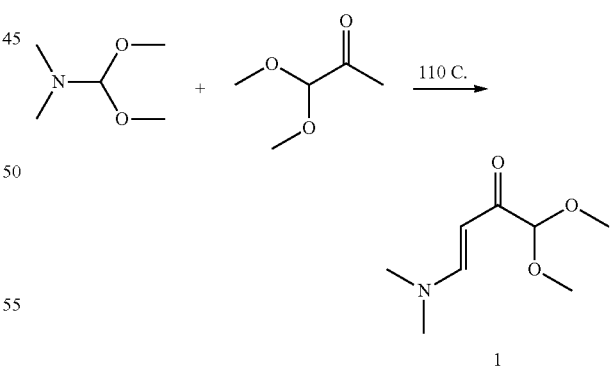

(E)-4-(dimethylamino)-1,1-dimethoxybut-3-en-2-one (1): 1,1-dimethoxy-N,N-dimethylmethanamine (100 g, 839 mmol, 1.02 equiv.) and 1,1-dimethoxypropan-2-one (97 g, 821 mmol) were added and stirred at 110° C. for 3 hours. The produced methanol was removed by a Dean-Stark apparatus. After the solution was cooled to room temperature, the remaining volatile materials were removed in vacuo to provide 130 g of the crude product, (E)-4-(dimethylamino)-1,1- dimethoxybut-3-en-2-one (1) (130 g, 143 g theoretical, 91%). LC-MS m/z 283 (M+1). Reference: WO20060097341A1, pg 67.

2-(methylthio)pyrimidine (3) as a brown oil (53.7 g, 150 g theoretical, 35.7%). LC-MS m/z 201 (M+1). Reference: WO20060097341A1, pg 67.

Example 2

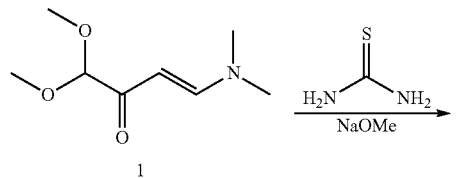

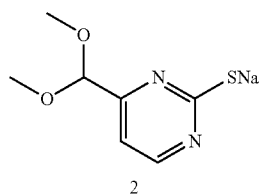

sodium 4-(dimethoxymethyl)pyrimidine-2-thiolate (2): A solution of thiourea (64.7 g, 850 mmol, 1.13 equiv.), sodium methanolate (95%, 40.5 g, 751 mmol, 1.0 equiv.) in methanol (500 mL, 1.5 M) was stirred at room temperature for 30 minutes. A solution of (E)-4-(dimethylamino)-1,1-dimethoxybut-3-en-2-one (1) (130 g, 751 mmol) in methanol (200 mL) was added and the reaction stirred at room temperature for 2 h. The crude sodium 4-(dimethoxymethyl)pyrimidine-2-thiolate (2) was used directly in the next step without further purification. LC-MS m/z 209 (M+1). Reference: WO20060097341A1, pg 67.

Example 3

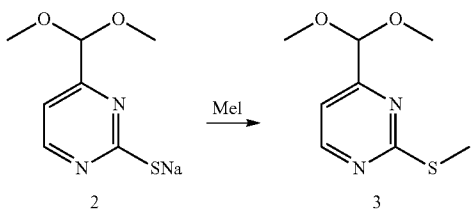

4-(dimethoxymethyl)-2-(methylthio)pyrimidine (β): Iodomethane (128 g, 902 mmol, 1.20 equiv.) was added carefully to the crude solution of sodium 4-(dimethoxymethyl) pyrimidine-2-thiolate (2) (156 g, 751 mmol) in methanol (700 mL, 1.1 M) while maintaining the reaction temperature below 28° C. using an ice-water bath for cooling. The resulting mixture was stirred at room temperature for 16 h. After removal of the solvent under reduced pressure, the residue was diluted with water (300 mL) and extracted with ethyl acetate (2×150 mL). The combined organic layer was concentrated under reduced pressure and the crude residue purified by passing through a short silica gel pad and washing with diethyl ether (200 mL) to afford 4-(dimethoxymethyl)-

Example 4

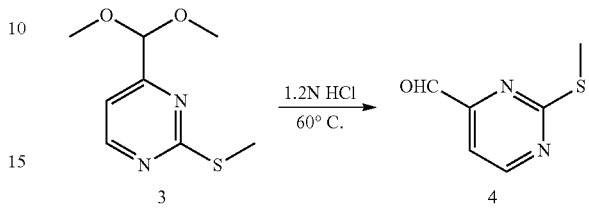

2-(methylthio)pyrimidine-4-carbaldehyde (4): 4-(dimethoxymethyl)-2-(methylthio)pyrimidine (3) (53.7 g, 268 mmol) was added carefully to 1.2 N aqueous HCl (300 mL, 268 mmol, 1.0 equiv.) and stirred at 60° C. for 3 hours. The reaction mixture was then cooled to room temperature and neutralized by the slow addition of solid sodium bicarbonate. The crude mixture was extracted with diethyl ether (3×150 mL) and the combined organic layer was concentrated under reduced pressure to afford 2-(methylthio)pyrimidine-4-carbaldehyde (4) as a yellow solid (14.2 g, 41.5 g theoretical, 34%). LC-MS m/z 155 (M+1). Reference: W2006009734A1, pg 67.

Example 5

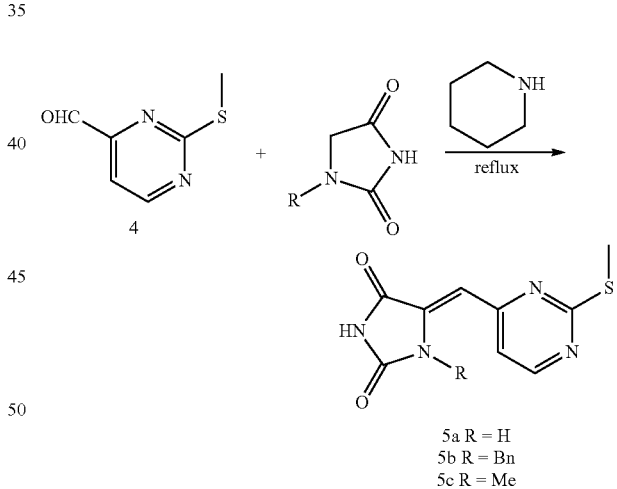

5a R = H
5b R = Bn
5c R = Me (Z)-5-((2-(methylthio)pyrimidin-4-yl)methylene)imidazolidine-2,4-dione (5a): A 40 mL round bottomed vial was charged with 2-(methylthio)pyrimidine-4-carbaldehyde (4) (771 mg, 5 mmol), imidazolidine-2,4-dione (500 mg, 5 mmol, 1.0 equiv.), and piperidine (400 μL, 4 mmol, 0.8 equiv.) in ethanol (20 mL, 0.25 M). The reaction mixture was heated to 80° C. and shaken for 20 h. The resulting yellow precipitate was isolated by filtration and washed with ethanol (1×20 mL) and dried in vacuo to afford (Z)-5-((2-(methylthio)pyrimidin-4-yl)methylene)imidazolidine-2,4-dione (5a) as a yellow solid (565 mg, 1.18 mg theoretical, 48%). LC-MS m/z 237 (M+1). The same procedure can be used to prepare 5b or 5c by replacing imidazolidine-2,4-dione with 1-benzylimidazolidine-2,4-dione or 1-methylimidazolidine-2,4-dione respectively.

Example 6

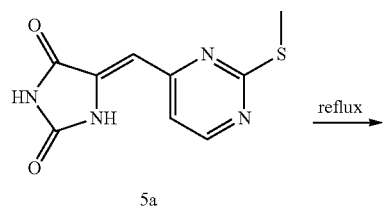

(Z)-5-((2-(methylsulfonyl)pyrimidin-4-yl)methylene)imidazolidine-2,4-dione (6a): A mixture of (Z)-5-((2-(methylthio)pyrimidin-4-yl)methylene)imidazolidine-2,4-dione (5) (3.5 g, 14.83 mmol) in THF (100 mL, 0.15 M) was treated with a solution of oxone (27.35 g, 44.5 mmol, 3.0 equiv.) in water (175 mL). The resulting mixture was stirred at room temperature for 48 h. The resulting precipitate was filtered and washed with water (20 mL) and diethyl ether (20 mL) to afford (Z)-5-((2-(methylsulfonyl)pyrimidin-4-yl)methylene)imidazolidine-2,4-dione (6) as a solid (2.48 g, 3.97 g theoretical, 62%). LC-MS m/z 269 (M+1). The same procedure can be used with the N-benzyl (6b) and N-methyl (6c) analogs in comparable yields.

Example 7

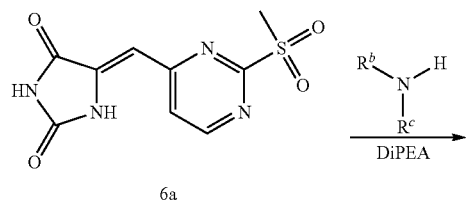

General displacement procedure 1: 2 dram round bottomed vials were charged with (Z)-5-((2-(methylsulfonyl)pyrimidin-4-yl)methylene)imidazolidine-2,4-dione (6a) (30 mg, 0.1118 mmol), DMSO (0.5 mL, 0.2 M), diisopropylethylamine (50 µL, 0.306 mmol, 2.7 equiv.), and the appropriate amine (0.1118 mmol, 1.0 equiv.). The reaction mixture was heated to 120° C. and shaken for 16 h. The solvent was removed under reduced pressure (Genevac HT-4) and the crude residues were purified using reverse phase HPLC (MS-triggered fraction collection) with an acetonitrile/water gradient and trifluoroacetic acid as the modifier. The pure fractions were then concentrated under reduced pressure (Genevac (HT-4) to provide the desired products (7a).

Example 8

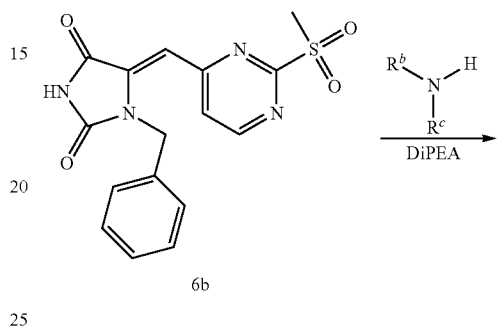

General displacement procedure 2: 2 dram round bottomed vials were charged with (Z)-1-benzyl-5-((2-(methylsulfonyl)pyrimidin-4-yl)methylene)imidazolidine-2,4-dione (6b) (30 mg, 0.084 mmol), DMSO (0.5 mL, 0.16 M), diisopropylethylamine (50 µL, 0.306 mmol, 3.6 equiv.), and the appropriate amine (0.084 mmol, 3.6 equiv.). The reaction mixture was heated to 120° C. and shaken for 16 h. The solvent was removed under reduced pressure (Genevac HT-4) and the crude residues were purified using reverse phase HPLC (MS-triggered fraction collection) with an acetonitrile/water gradient and trifluoroacetic acid as the modifier. The pure fractions were then concentrated under reduced pressure (Genevac (HT-4) to provide the desired products (7b).

Example 9

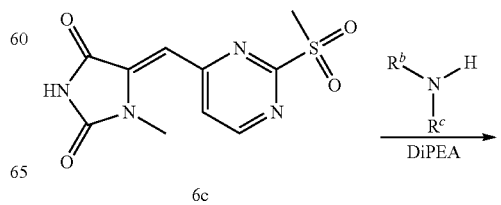

-continued

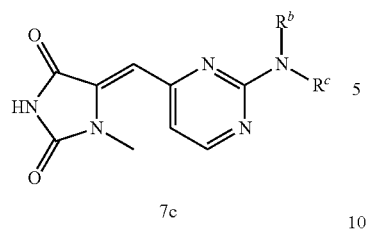

7c

General displacement procedure 3: 2 dram round bottomed vials were charged with (Z)-1-methyl-5-((2-(methylsulfonyl)pyrimidin-4-yl)methylene)imidazolidine-2,4-dione (6c) (25 mg, 0.089 mmol), DMSO (0.5 mL, 0.16 M), diisopropylethylamine (50 µL, 0.177 mmol, 3.4 equiv.), and the appropriate amine (0.089 mmol, 1.0 equiv.). The reaction mixture was heated to 120° C. and shaken for 16 h. The solvent was removed under reduced pressure (Genevac HT-4) and the crude residues were purified using reverse phase HPLC (MS-triggered fraction collection) with an acetonitrile/water gradient and trifluoroacetic acid as the modifier. The pure fractions were then concentrated under reduced pressure (Genevac (HT-4) to provide the desired products (7c).

Example 10

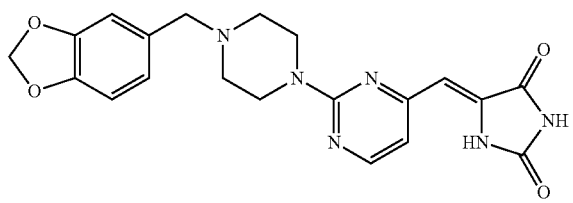 [SMILES: O=C1NC(=O)/C(=C/c2ccnc(N3CCN(Cc4ccc5c(c4)OCO5)CC3)n2)N1]

(Z)-5-((2-(4-(benzo[d][1,3]dioxol-5-ylmethyl)piperazin-1'-yl)pyrimidin-4-yl)methylene)imidazolidine-2,4-dione was prepared using general displacement procedure 1 (25.1 mg, 36.4 mg theoretical, 69%). LC-MS m/z 409.4 (M+1).

Example 11

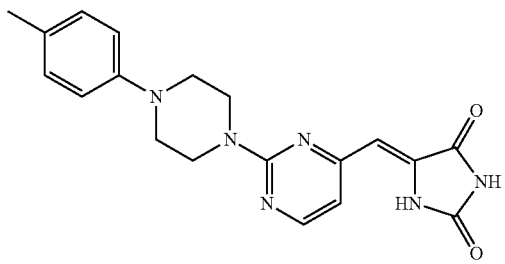 [SMILES: Cc1ccc(N2CCN(c3nccc(/C=C4\NC(=O)NC4=O)n3)CC2)cc1]

(Z)-5-((2-(4-(p-tolyl)piperazin-1-yl)pyrimidin-4-yl)methylene)imidazolidine-2,4-dione was prepared using general displacement procedure 1 (14.3 mg, 32.5 mg theoretical, 44%). LC-MS m/z 365.4 (M+1).

Example 12

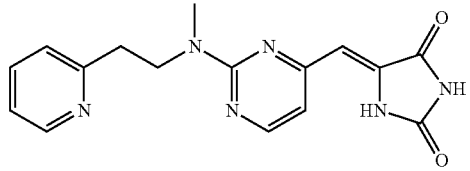 [SMILES: CN(CCc1ccccn1)c1nccc(/C=C2\NC(=O)NC2=O)n1]

(Z)-5-((2-(methyl(2-(pyridin-2-yl)ethyl)amino)pyrimidin-4-yl)methylene)imidazolidine-2,4-dione was prepared using general displacement procedure 1 (24.4 mg, 29 mg theoretical, 84.1%). LC-MS m/z 325.3 (M+1).

Example 13

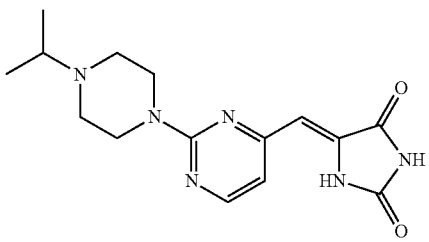 [SMILES: CC(C)N1CCN(c2nccc(/C=C3\NC(=O)NC3=O)n2)CC1]

(Z)-5-((2-(4-isopropylpiperazin-1-yl)pyrimidin-4-yl)methylene)imidazolidine-2,4-dione was prepared using general displacement procedure 1 (21.9 mg, 28.2 mg theoretical, 77.7%). LC-MS m/z 317.4 (M+1).

Example 14

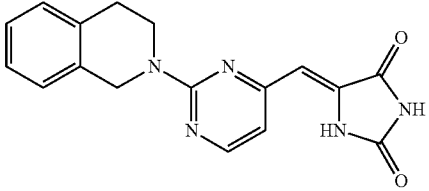 [SMILES: O=C1NC(=O)/C(=C/c2ccnc(N3CCc4ccccc4C3)n2)N1]

(Z)-5-((2-(3,4-dihydroisoquinolin-2(1H)-yl)pyrimidin-4-yl)methylene)imidazolidine-2,4-dione was prepared using general displacement procedure 1 (11.6 mg, 28.7 mg theoretical, 40.4%). LC-MS m/z 322.3 (M+1).

Example 15

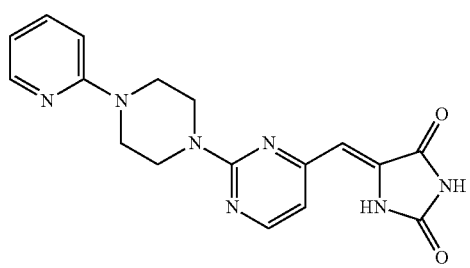 [SMILES: O=C1NC(=O)/C(=C/c2ccnc(N3CCN(c4ccccn4)CC3)n2)N1]

(Z)-5-((2-(4-(pyridin-2-yl)piperazin-1-yl)pyrimidin-4-yl)methylene)imidazolidine-2,4-dione was prepared using general displacement procedure 1 (6.1 mg, 31.4 mg theoretical, 19.4%). LC-MS m/z 352.4 (M+1).

Example 16

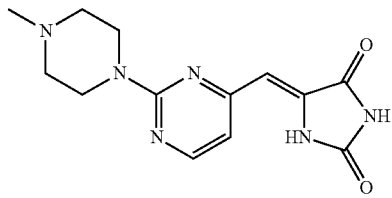 [SMILES: CN1CCN(c2nccc(/C=C3\NC(=O)NC3=O)n2)CC1]

(Z)-5-((2-(4-methylpiperazin-1-yl)pyrimidin-4-yl)methylene)imidazolidine-2,4-dione was prepared using general displacement procedure 1 (25.7 mg, 25.7 mg theoretical, 100%). LC-MS m/z 289.3 (M+1).

Example 17

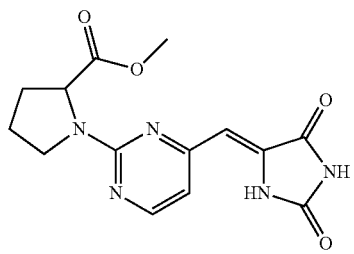 [SMILES: COC(=O)C1CCCN1c1nccc(/C=C2\NC(=O)NC2=O)n1]

(Z)-methyl 1-(4-((2,5-dioxoimidazolidin-4-ylidene)methyl)pyrimidin-2-yl)pyrrolidine-2-carboxylate was prepared using general displacement procedure 1 (14.4 mg, 28.3 mg theoretical, 50.9%). LC-MS m/z 318.3 (M+1).

Example 18

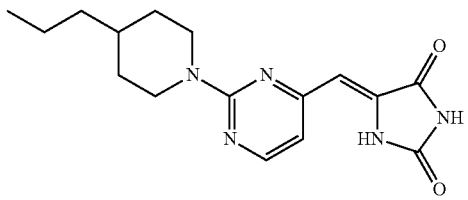 [SMILES: CCCC1CCN(c2nccc(/C=C3\NC(=O)NC3=O)n2)CC1]

(Z)-5-((2-(4-propylpiperidin-1-yl)pyrimidin-4-yl)methylene)imidazolidine-2,4-dione was prepared using general displacement procedure 1 (7.9 mg, 28.2 mg theoretical, 28%). LC-MS m/z 316.4 (M+1).

Example 19

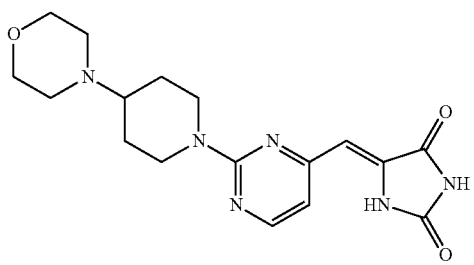 [SMILES: O=C1NC(=O)/C(=C/c2ccnc(N3CCC(N4CCOCC4)CC3)n2)N1]

(Z)-5-((2-(4-morpholinopiperidin-1-yl)pyrimidin-4-yl)methylene)imidazolidine-2,4-dione was prepared using general displacement procedure 1 (30.8 mg, 32 mg theoretical, 96.3%). LC-MS m/z 359.4 (M+1).

Example 20

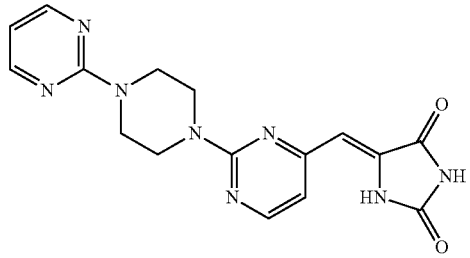 [SMILES: O=C1NC(=O)/C(=C/c2ccnc(N3CCN(c4ncccn4)CC3)n2)N1]

(Z)-5-((2-(4-(pyrimidin-2-yl)piperazin-1-yl)pyrimidin-4-yl)methylene)imidazolidine-2,4-dione was prepared using general displacement procedure 1 (4.3 mg, 31.5 mg theoretical, 13.7%). LC-MS m/z 353.4 (M+1).

Example 21

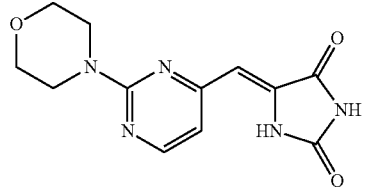 [SMILES: O=C1NC(=O)/C(=C/c2ccnc(N3CCOCC3)n2)N1]

(Z)-5-((2-morpholinopyrimidin-4-yl)methylene)imidazolidine-2,4-dione was prepared using general displacement procedure 1 (14 mg, 24.6 mg theoretical, 56.9%). LC-MS m/z 276.3 (M+1).

Example 22

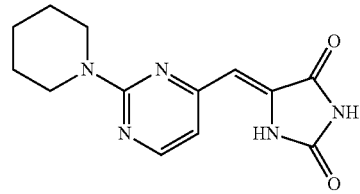 [SMILES: O=C1NC(=O)/C(=C/c2ccnc(N3CCCCC3)n2)N1]

(Z)-5-((2-(piperidin-1-yl)pyrimidin-4-yl)methylene)imidazolidine-2,4-dione was prepared using general displacement procedure 1 (16.8 mg, 24.4 mg theoretical, 68.9%). LC-MS m/z 274.3 (M+1).

Example 23

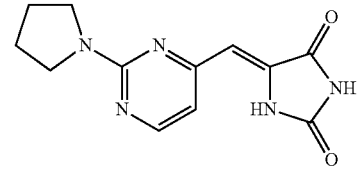 [SMILES: O=C1NC(=O)/C(=C/c2ccnc(N3CCCC3)n2)N1]

(Z)-5-((2-(pyrrolidin-1-yl)pyrimidin-4-yl)methylene)imidazolidine-2,4-dione was prepared using general displacement procedure 1 (2.9 mg, 23.2 mg theoretical, 12.5%). LC-MS m/z 260.3 (M+1).

Example 24

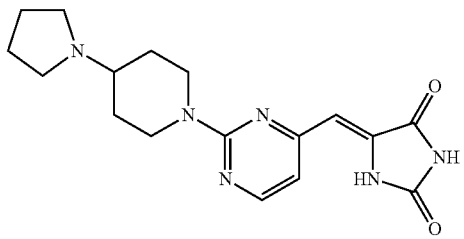 [SMILES: O=C1NC(=O)/C(=C/c2ccnc(N3CCC(N4CCCC4)CC3)n2)N1]

(Z)-5-((2-(4-(pyrrolidin-1-yl)piperidin-1-yl)pyrimidin-4-yl)methylene)imidazolidine-2,4-dione was prepared using general displacement procedure 1 (26.7 mg, 30.6 mg theoretical, 87.3%). LC-MS m/z 343.4 (M+1).

Example 25

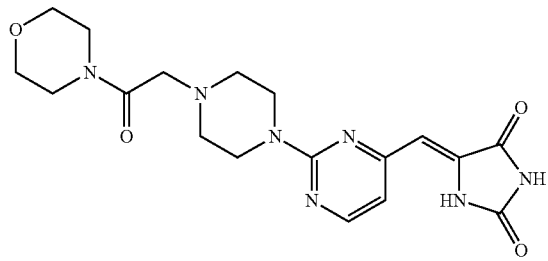 [SMILES: O=C1NC(=O)/C(=C/c2ccnc(N3CCN(CC(=O)N4CCOCC4)CC3)n2)N1]

(Z)-5-((2-(4-(2-morpholino-2-oxoethyl)piperazin-1-yl)pyrimidin-4-yl)methylene)imidazolidine-2,4-dione was prepared using general displacement procedure 1 (35.8 mg, 35.8 mg theoretical, 100%). LC-MS m/z 402.4 (M+1).

Example 26

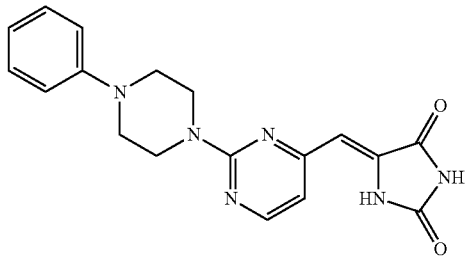 [SMILES: O=C1NC(=O)/C(=C/c2ccnc(N3CCN(c4ccccc4)CC3)n2)N1]

(Z)-5-((2-(4-phenylpiperazin-1-yl)pyrimidin-4-yl)methylene)imidazolidine-2,4-dione was prepared using general displacement procedure 1 (10.6 mg, 31.3 mg theoretical, 33.9%). LC-MS m/z 351.4 (M+1).

Example 27

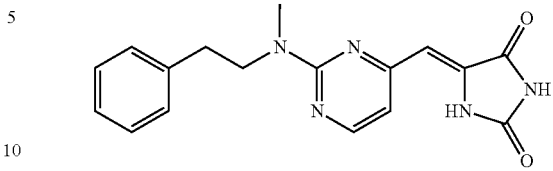

(Z)-5-((2-(methyl(phenethyl)amino)pyrimidin-4-yl)methylene)imidazolidine-2,4-dione was prepared using general displacement procedure 1 (15.8 mg, 28.9 mg theoretical, 54.7%). LC-MS m/z 324.3 (M+1).

Example 28

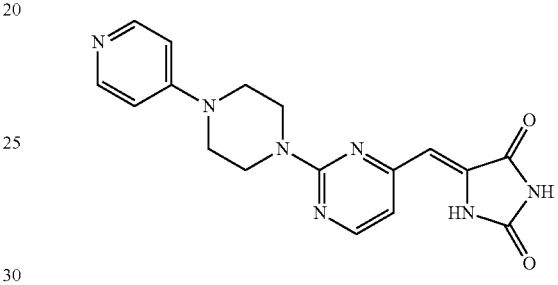

(Z)-5-((2-(4-(pyridin-4-yl)piperazin-1-yl)pyrimidin-4-yl)methylene)imidazolidine-2,4-dione was prepared using general displacement procedure 1 (15.6 mg, 31.4 mg theoretical, 49.7%). LC-MS m/z 352.4 (M+1).

Example 29

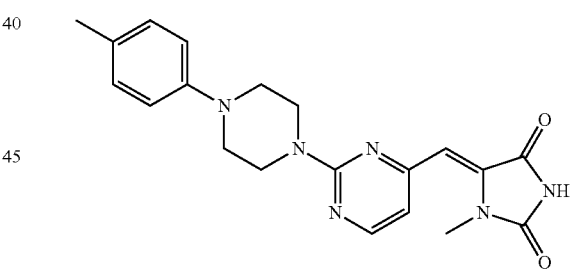

(Z)-1-methyl-5-((2-(4-(p-tolyl)piperazin-1-yl)pyrimidin-4-yl)methylene)imidazolidine-2,4-dione was prepared using general displacement procedure 3 (9.9 mg, 33.8 mg theoretical, 29.3%). LC-MS m/z 379.4 (M+1).

Example 30

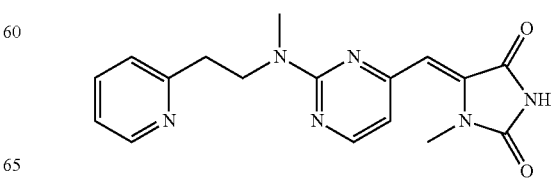

(Z)-1-methyl-5-((2-(methyl(2-(pyridin-2-yl)ethyl)amino) pyrimidin-4-yl)methylene)imidazolidine-2,4-dione was prepared using general displacement procedure 3 (10.3 mg, 30.2 mg theoretical, 34.1%). LC-MS m/z 339.4 (M+1).

Example 31

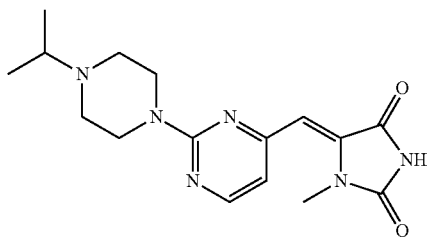 [SMILES: CC(C)N1CCN(c2nccc(/C=C3/C(=O)NC(=O)N3C)n2)CC1]

(Z)-5-((2-(4-isopropylpiperazin-1-yl)pyrimidin-4-yl)methylene)-1-methylimidazolidine-2,4-dione was prepared using general displacement procedure 3 (10.4 mg, 29.5 mg theoretical, 35.3%). LC-MS m/z 331.4 (M+1).

Example 32

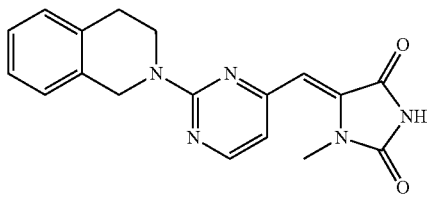 [SMILES: CN1C(=O)NC(=O)/C1=C/c1ccnc(N2CCc3ccccc3C2)n1]

(Z)-5-((2-(3,4-dihydroisoquinolin-2(1H)-yl)pyrimidin-4-yl)methylene)-1-methylimidazolidine-2,4-dione was prepared using general displacement procedure 3 (10.9 mg, 29.9 mg theoretical, 36.5%). LC-MS m/z 336.4 (M+1).

Example 33

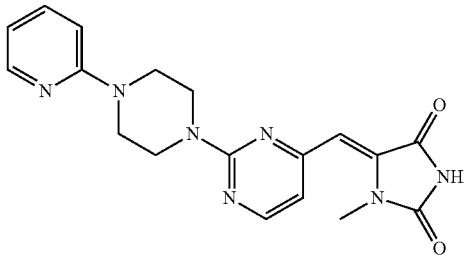 [SMILES: CN1C(=O)NC(=O)/C1=C/c1ccnc(N2CCN(c3ccccn3)CC2)n1]

(Z)-1-methyl-5-((2-(4-(pyridin-2-yl)piperazin-1-yl)pyrimidin-4-yl)methylene)imidazolidine-2,4-dione was prepared using general displacement procedure 3 (15.7 mg, 32.6 mg theoretical, 48.2%). LC-MS m/z 366.4 (M+1).

Example 34

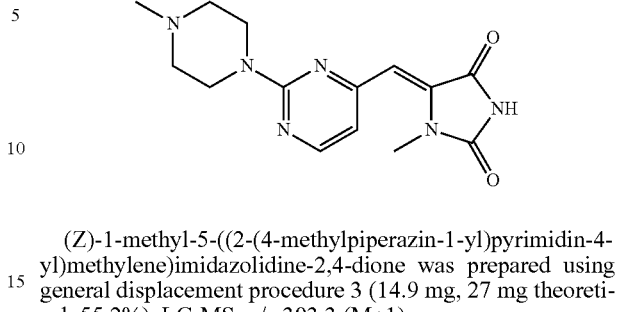

(Z)-1-methyl-5-((2-(4-methylpiperazin-1-yl)pyrimidin-4-yl)methylene)imidazolidine-2,4-dione was prepared using general displacement procedure 3 (14.9 mg, 27 mg theoretical, 55.2%). LC-MS m/z 303.3 (M+1).

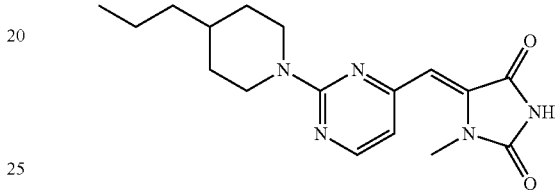

Example 35

(Z)-1-methyl-5-((2-(4-propylpiperidin-1-yl)pyrimidin-4-yl)methylene)imidazolidine-2,4-dione was prepared using general displacement procedure 3 (5.8 mg, 29.4 mg theoretical, 19.7%). LC-MS m/z 330.4 (M+1).

Example 36

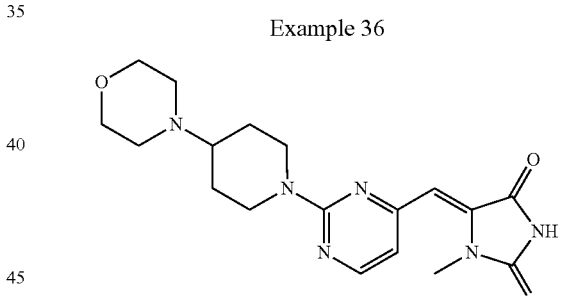

(Z)-1-methyl-5-((2-(4-morpholinopiperidin-1-yl)pyrimidin-4-yl)methylene)imidazolidine-2,4-dione was prepared using general displacement procedure 3 (16 mg, 33.2 mg theoretical, 48.2%). LC-MS m/z 373.4 (M+1).

Example 37

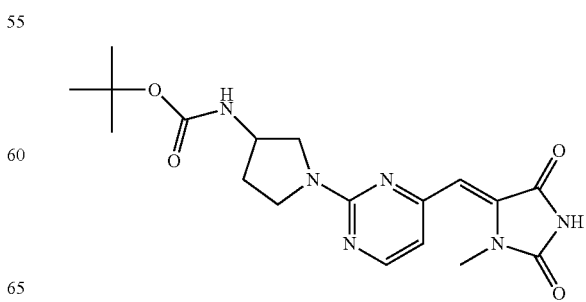

(Z)-tert-butyl(1-(4-((3-methyl-2,5-dioxoimidazolidin-4-ylidene)methyl)pyrimidin-2-yl)pyrrolidin-3-yl)carbamate was prepared using general displacement procedure 3 (19 mg, 34.7 mg theoretical, 54.8%). LC-MS m/z 389.4 (M+1).

Example 38

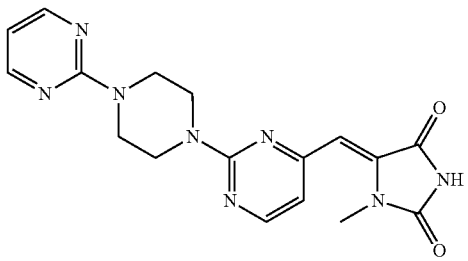 [SMILES: CN1C(=O)NC(=O)/C1=C/c1ccnc(N2CCN(c3ncccn3)CC2)n1]

(Z)-1-methyl-5-((2-(4-(pyrimidin-2-yl)piperazin-1-yl)pyrimidin-4-yl)methylene)imidazolidine-2,4-dione was prepared using general displacement procedure 3 (17.1 mg, 32.7 mg theoretical, 52.3%). LC-MS m/z 367.4 (M+1).

Example 39

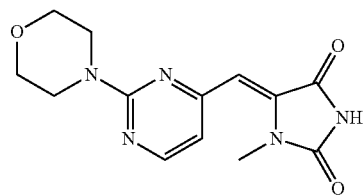 [SMILES: CN1C(=O)NC(=O)/C1=C/c1ccnc(N2CCOCC2)n1]

(Z)-1-methyl-5-((2-morpholinopyrimidin-4-yl)methylene)imidazolidine-2,4-dione was prepared using general displacement procedure 3 (17.8 mg, 25.8 mg theoretical, 69%). LC-MS m/z 290.3 (M+1).

Example 40

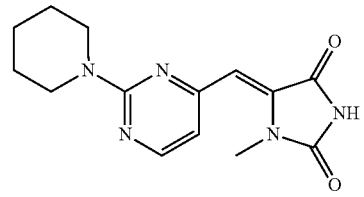 [SMILES: CN1C(=O)NC(=O)/C1=C/c1ccnc(N2CCCCC2)n1]

(Z)-1-methyl-5-((2-(piperidin-1-yl)pyrimidin-4-yl)methylene)imidazolidine-2,4-dione was prepared using general displacement procedure 3 (11.5 mg, 25.7 mg theoretical, 44.7%). LC-MS m/z 288.3 (M+1).

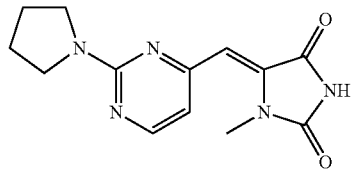 [SMILES: CN1C(=O)NC(=O)/C1=C/c1ccnc(N2CCCC2)n1]

(Z)-1-methyl-5-((2-(pyrrolidin-1-yl)pyrimidin-4-yl)methylene)imidazolidine-2,4-dione was prepared using general displacement procedure 3 (13.5 mg, 24.4 mg theoretical, 55.3%). LC-MS m/z 274.3 (M+1).

Example 42

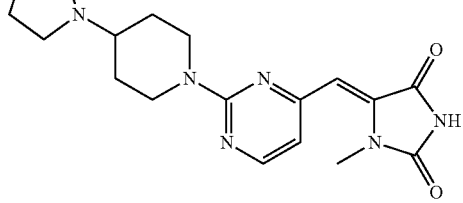

(Z)-1-methyl-5-((2-(4-(pyrrolidin-1-yl)piperidin-1-yl)pyrimidin-4-yl)methylene)imidazolidine-2,4-dione was prepared using general displacement procedure 3 (11.9 mg, 31.8 mg theoretical, 37.4%). LC-MS m/z 357.4 (M+1).

Example 43

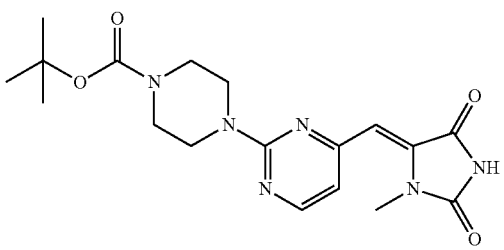 [SMILES: CN1C(=O)NC(=O)/C1=C/c1ccnc(N2CCN(C(=O)OC(C)(C)C)CC2)n1]

(Z)-tert-butyl 4-(4-((3-methyl-2,5-dioxoimidazolidin-4-ylidene)methyl)pyrimidin-2-yl)piperazine-1-carboxylate was prepared using general displacement procedure 3 (5.4 mg, 34.7 mg theoretical, 15.6%). LC-MS m/z 389.4 (M+1).

Example 44

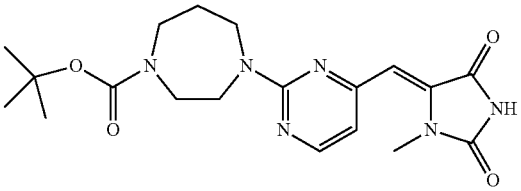 [SMILES: CN1C(=O)NC(=O)/C1=C/c1ccnc(N2CCCN(C(=O)OC(C)(C)C)CC2)n1]

(Z)-tert-butyl 4-(4-((3-methyl-2,5-dioxoimidazolidin-4-ylidene)methyl)pyrimidin-2-yl)-1,4-diazepane-1-carboxylate was prepared using general displacement procedure 3 (15.3 mg, 35.9 mg theoretical, 42.6%). LC-MS m/z 403.4 (M+1).

Example 45

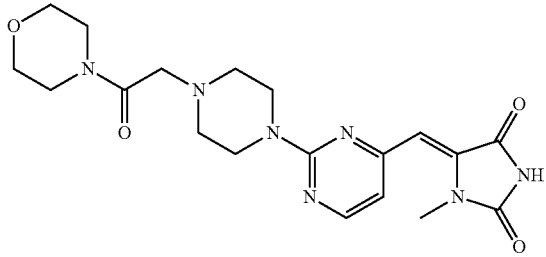 [SMILES: CN1C(=O)NC(=O)/C1=C/c1ccnc(N2CCN(CC(=O)N3CCOCC3)CC2)n1]

(Z)-1-methyl-5-((2-(4-(2-morpholino-2-oxoethyl)piperazin-1-yl)pyrimidin-4-yl)methylene)imidazolidine-2,4-dione was prepared using general displacement procedure 3 (18.6 mg, 37.1 mg theoretical, 50.1%). LC-MS m/z 416.4 (M+1).

Example 46

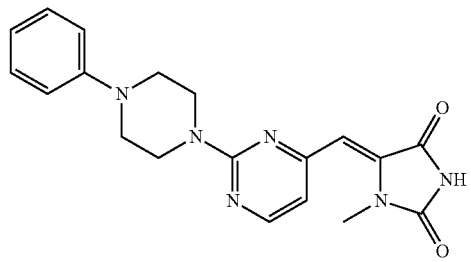 [SMILES: CN1C(=O)NC(=O)/C1=C/c1ccnc(N2CCN(c3ccccc3)CC2)n1]

(Z)-1-methyl-5-((2-(4-phenylpiperazin-1-yl)pyrimidin-4-yl)methylene)imidazolidine-2,4-dione was prepared using general displacement procedure 3 (15.8 mg, 32.5 mg theoretical, 48.6%). LC-MS m/z 365.4 (M+1).

Example 47

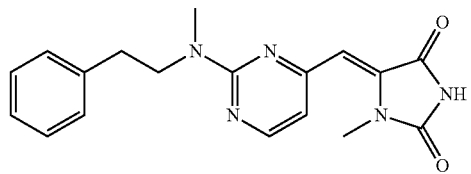 [SMILES: CN1C(=O)NC(=O)/C1=C/c1ccnc(N(C)CCc2ccccc2)n1]

(Z)-1-methyl-5-((2-(methyl(phenethyl)amino)pyrimidin-4-yl)methylene)imidazolidine-2,4-dione was prepared using general displacement procedure 3 (10.6 mg, 30.1 mg theoretical, 35.2%). LC-MS m/z 338.4 (M+1).

Example 48

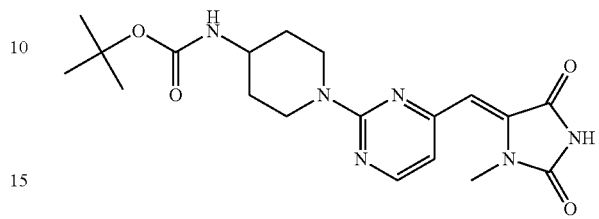

(Z)-tert-butyl(1-(4-((3-methyl-2,5-dioxoimidazolidin-4-ylidene)methyl)pyrimidin-2-yl)piperidin-4-yl)carbamate was prepared using general displacement procedure 3 (17.6 mg, 35.9 mg theoretical, 49%). LC-MS m/z 403.4 (M+1).

Example 49

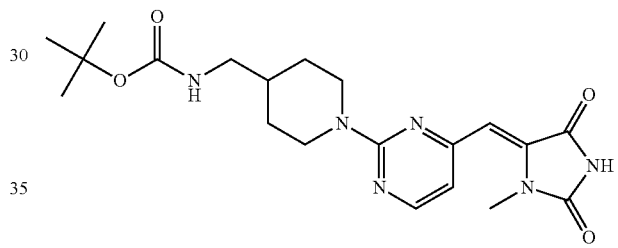

(Z)-tert-butyl((1-(4-((3-methyl-2,5-dioxoimidazolidin-4-ylidene)methyl)pyrimidin-2-yl)piperidin-3-yl)methyl)carbamate was prepared using general displacement procedure 3 (17.3 mg, 37.2 mg theoretical, 46.5%). LC-MS m/z 417.5 (M+1).

Example 50

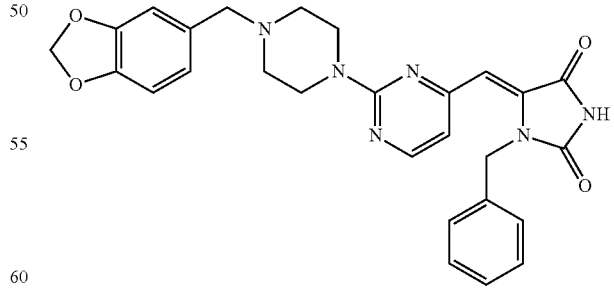

(Z)-5-((2-(4-(benzo[d][1,3]-dioxol-5-ylmethyl)piperazin-1-yl)pyrimidin-4-yl)methylene)-1-benzylimidazolidine-2,4-dione was prepared using general displacement procedure 2 (21 mg, 44.5 mg theoretical, 47.2%). LC-MS m/z 499.5 (M+1).

Example 51

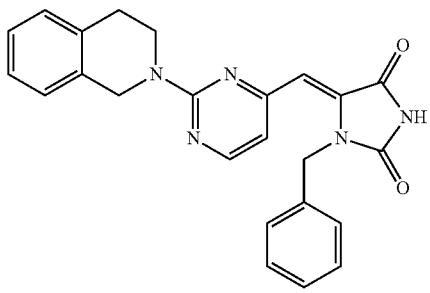 [SMILES: O=C1NC(=O)N(Cc2ccccc2)/C1=C\c1ccnc(N2CCc3ccccc3C2)n1]

(Z)-1-benzyl-5-((2-(3,4-dihydroisoquinolin-2(1H)-yl)pyrimidin-4-yl)methylene)imidazolidine-2,4-dione was prepared using general displacement procedure 2 (8.2 mg, 36.7 mg theoretical, 22.3%). LC-MS m/z 412.5 (M+1).

Example 52

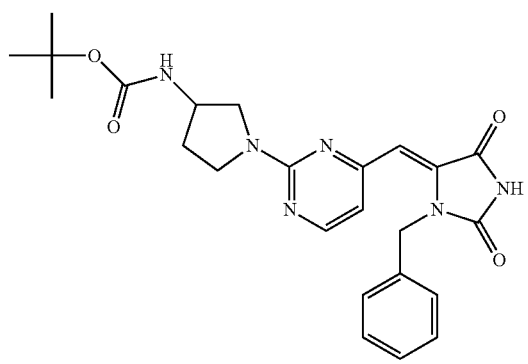 [SMILES: CC(C)(C)OC(=O)NC1CCN(c2nccc(/C=C3/C(=O)NC(=O)N3Cc3ccccc3)n2)C1]

(Z)-tert-butyl(1-(4-((3-benzyl-2,5-dioxoimidazolidin-4-ylidene)methyl)pyrimidin-2-yl)pyrrolidin-3-yl)carbamate was prepared using general displacement procedure 2 (41.4 mg, 41.4 mg theoretical, 100%). LC-MS m/z 465.5 (M+1).

Example 53

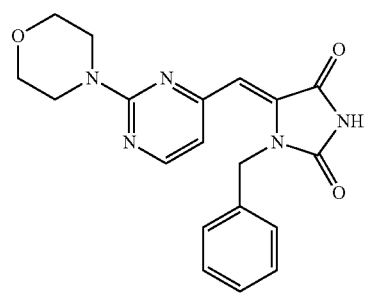 [SMILES: O=C1NC(=O)N(Cc2ccccc2)/C1=C\c1ccnc(N2CCOCC2)n1]

(Z)-1-benzyl-5-((2-morpholinopyrimidin-4-yl)methylene)imidazolidine-2,4-dione was prepared using general displacement procedure 2 (11.1 mg, 32.6 mg theoretical, 34%). LC-MS m/z 366.4 (M+1).

Example 54

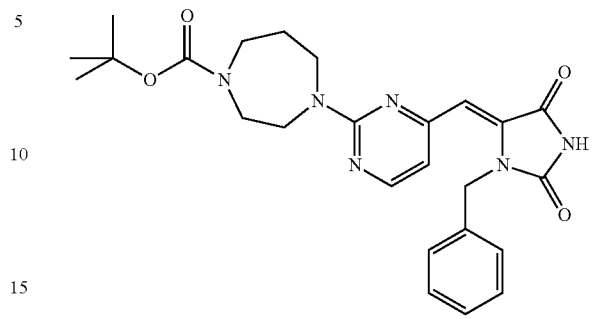

(Z)-tert-butyl 4-(4-((3-benzyl-2,5-dioxoimidazolidin-4-ylidene)methyl)pyrimidin-2-yl)-1,4-diazepane-1-carboxylate was prepared using general displacement procedure 2 (12.1 mg, 42.7 mg theoretical, 28.3%). LC-MS m/z 479.5 (M+1).

Example 55

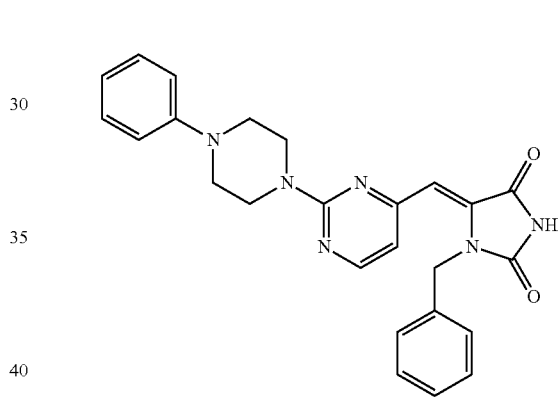

(Z)-1-benzyl-5-((2-(4-phenylpiperazin-1-yl)pyrimidin-4-yl)methylene)imidazolidine-2,4-dione was prepared using general displacement procedure 2 (7.4 mg, 39.3 mg theoretical, 18.8%). LC-MS m/z 441.5 (M+1).

Example 56

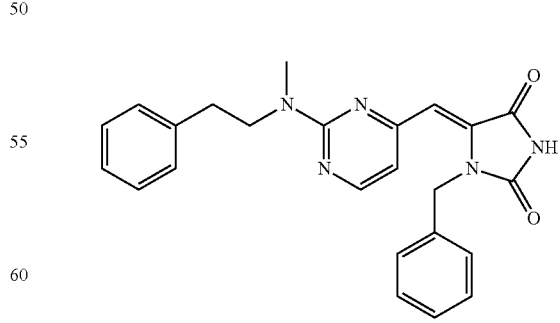

(Z)-1-benzyl-5-((2-(methyl)phenethyl)amino)pyrimidin-4-yl)methylene)imidazolidine-2,4-dione was prepared using general displacement procedure 2 (15.9 mg, 36.9 mg theoretical, 43.1%). LC-MS m/z 414.5 (M+1).

Example 57

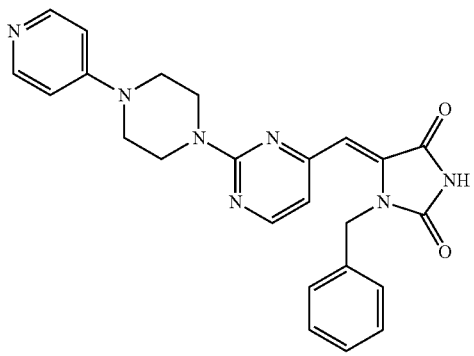 [SMILES: O=C1NC(=O)N(Cc2ccccc2)/C1=C\c1ccnc(N2CCN(c3ccncc3)CC2)n1]

(Z)-1-benzyl-5-((2-(4-(pyridin-4-yl)piperazin-1-yl)pyrimidin-4-yl)methylene)imidazolidine-2,4-dione was prepared using general displacement procedure 2 (9.9 mg, 39.4 mg theoretical, 25.1%). LC-MS m/z 442.5 (M+1).

Example 58

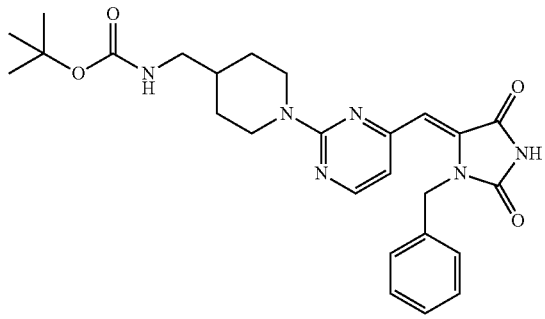 [SMILES: CC(C)(C)OC(=O)NCC1CCN(c2nccc(/C=C3/C(=O)NC(=O)N3Cc3ccccc3)n2)CC1]

(Z)-tert-butyl((1-(4-(((3-benzyl-2,5-dioxoimidazolidin-4-ylidene)methyl)pyrimidin-2-yl)piperidin-3-yl)methyl)carbamate was prepared using general displacement procedure 2 (19.4 mg, 43.9 mg theoretical, 44.2%). LC-MS m/z 493.6 (M+1).

Example 59

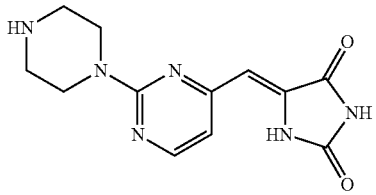 [SMILES: O=C1NC(=O)/C(=C/c2ccnc(N3CCNCC3)n2)N1]

(Z)-5-((2-(piperazin-1-yl)pyrimidin-4-yl)methylene)imidazolidine-2,4-dione: The boc-protected compound was prepared using general displacement procedure 1. The purified boc-protected compound was treated with dichloromethane (1.0 mL), hydrochloric acid in methanol (500 μL, 1.25 M) and shaken at 50° C. for 16 h. The reaction mixture was then concentrated under reduced pressure (Genevac HT-4) to provide the desired compound (5 mg, 24.5 mg theoretical, 20.4%). LC-MS m/z 275.3 (M+1).

Example 60

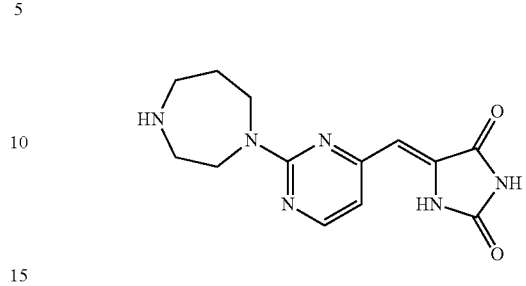

(Z)-5-((2-(1,4-diazepan-1-yl)pyrimidin-4-yl)methylene)imidazolidine-2,4-dione: The boc-protected compound was prepared using general displacement procedure 1. The purified boc-protected compound was treated with dichloromethane (1.0 mL), hydrochloric acid in methanol (500 μL, 1.25 M) and shaken at 50° C. for 16 h. The reaction mixture was then concentrated under reduced pressure (Genevac HT-4) to provide the desired compound (2 mg, 25.7 mg theoretical, 7.8%). LC-MS m/z 289.3 (M+1).

Example 61

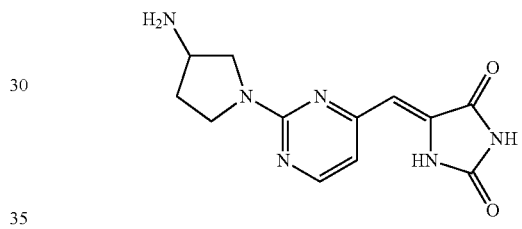

(Z)-5-((2-(3-aminopyrrolidin-1-yl)pyrimidin-4-yl)methylene)imidazolidine-2,4-dione: The boc-protected compound was prepared using general displacement procedure 1. The purified boc-protected compound was treated with dichloromethane (1.0 mL), hydrochloric acid in methanol (500 μL, 1.25 M) and shaken at 50° C. for 16 h. The reaction mixture was then concentrated under reduced pressure (Genevac HT-4) to provide the desired compound (3.6 mg, 24.5 mg theoretical, 14.7%). LC-MS m/z 275.3 (M+1).

Example 62

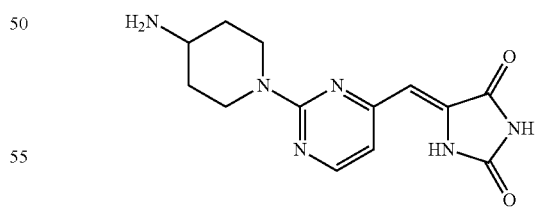

(Z)-5-((2-(4-aminopiperidin-1-yl)pyrimidin-4-yl)methylene)imidazolidine-2,4-dione: The boc-protected compound was prepared using general displacement procedure 1. The purified boc-protected compound was treated with dichloromethane (1.0 mL), hydrochloric acid in methanol (500 μL, 1.25M) and shaken at 50° C. for 16 h. The reaction mixture was then concentrated under reduced pressure (Genevac HT-4) to provide the desired compound (6.1 mg, 25.7 mg theoretical, 23.7%). LC-MS m/z 289.3 (M+1).

Example 63

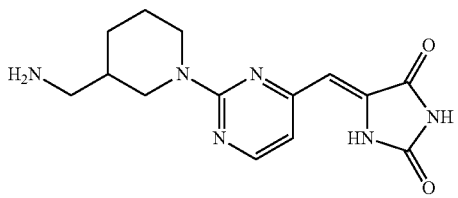 [SMILES: NCC1CCCN(c2nccc(/C=C3\NC(=O)NC3=O)n2)C1]

(Z)-5-((2-(3-(aminomethyl)piperidin-1-yl)pyrimidin-4-yl)methylene)imidazolidine-2,4-dione: The boc-protected compound was prepared using general displacement procedure 1. The purified boc-protected compound was treated with dichloromethane (1.0 mL), hydrochloric acid in methanol (500 μL, 1.25 M) and shaken at 50° C. for 16 h. The reaction mixture was then concentrated under reduced pressure (Genevac HT-4) to provide the desired compound (4.7 mg, 27 mg theoretical, 17.4%). LC-MS m/z 303.3 (M+1).

Example 64

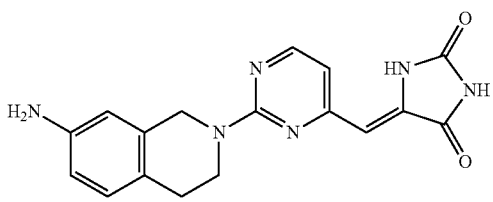 [SMILES: Nc1ccc2c(c1)CN(c1nccc(/C=C3\NC(=O)NC3=O)n1)CC2]

(Z)-5-((2-(7-amino-3,4-dihydroisoquinolin-2(1H)-yl)pyrimidin-4-yl)methylene)imidazolidine-2,4-dione: The boc-protected compound was prepared using general displacement procedure 1 and 1,2,3,4-tetrahydroisoquinolin-7-amine. The boc-protected compound was treated with dichloroethane (1.0 mL), trifluoroacetic acid (1.0 mL) and shaken at RT for 16 h. The reaction mixture was then concentrated under reduced pressure (Genevac HT-4) and the crude residues were purified using reverse phase HPLC (MS-triggered fraction collection) with a methanol/water gradient and trifluoroacetic acid as the modifier. The pure fractions were then concentrated under reduced pressure (Genevac (HT-4) to provide the desired product (11 mg, 37.6 mg theoretical, 29.2%). LC-MS m/z 337 (M+1).

Example 65

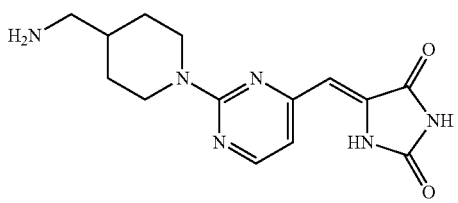 [SMILES: NCC1CCN(c2nccc(/C=C3\NC(=O)NC3=O)n2)CC1]

(Z)-5-((2-(4-(aminomethyl)piperidin-1-yl)pyrimidin-4-yl)methylene)imidazolidine-2,4-dione: The boc-protected compound was prepared using general displacement procedure 1 and tert-butyl (piperidin-4-ylmethyl)carbamate. The boc-protected compound was treated with dichloroethane (1.0 mL), trifluoroacetic acid (1.0 mL) and shaken at RT for 16 h. The reaction mixture was then concentrated under reduced pressure (Genevac HT-4) and the crude residues were purified using reverse phase HPLC (MS-triggered fraction collection) with a methanol/water gradient and trifluoroacetic acid as the modifier. The pure fractions were then concentrated under reduced pressure (Genevac (HT-4) to provide the desired product (37.5 mg, 63.9 mg theoretical, 58.7%). LC-MS m/z 303 (M+1).

Example 66

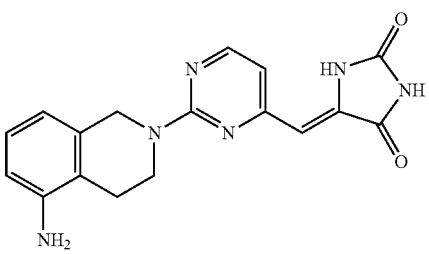 [SMILES: Nc1cccc2c1CCN(c1nccc(/C=C3\NC(=O)NC3=O)n1)C2]

(Z)-5-((2-(5-amino-3,4-dihydroisoquinolin-2(1H)-yl)pyrimidin-4-yl)methylene)imidazolidine-2,4-dione: The boc-protected compound was prepared using general displacement procedure 1 and 1,2,3,4-tetrahydroisoquinolin-5-amine. The boc-protected compound was then treated with dichloroethane (1.0 mL), trifluoroacetic acid (1.0 mL) and shaken at RT for 16 h. The reaction mixture was then concentrated under reduced pressure (Genevac HT-4) and the crude residues were purified using reverse phase HPLC (MS-triggered fraction collection) with a methanol/water gradient and trifluoroacetic acid as the modifier. The pure fractions were then concentrated under reduced pressure (Genevac (HT-4) to provide the desired product (35.1 mg, 37.6 mg theoretical, 93%). LC-MS m/z 337 (M+1).

Example 67

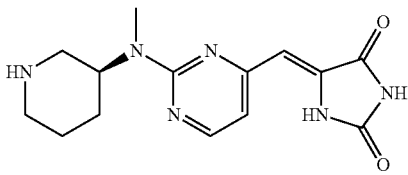 [SMILES: CN(c1nccc(/C=C2\NC(=O)NC2=O)n1)[C@H]1CCCNC1]

(S,Z)-5-((2-(methyl(piperidin-3-yl)amino)pyrimidin-4-yl)methylene)imidazolidine-2,4-dione: The boc-protected compound was prepared using general displacement procedure 1 and (R)-tert-butyl 3-(methylamino)piperidine-1-carboxylate. The boc-protected compound was then treaded with dichloroethane (1.0 mL), trifluoroacetic acid (1.0 mL) and shaken at RT for 16 h. The reaction mixture was then concentrated under reduced pressure (Genevac HT-4) and the crude residues were purified using reverse phase HPLC (MS-triggered fraction collection) with a methanol/water gradient and trifluoroacetic acid as the modifier. The pure fractions were then concentrated under reduced pressure (Genevac (HT-4) to provide the desired product (16.1 mg, 18.7 mg theoretical, 86%). LC-MS m/z 303 (M+1).

Example 68

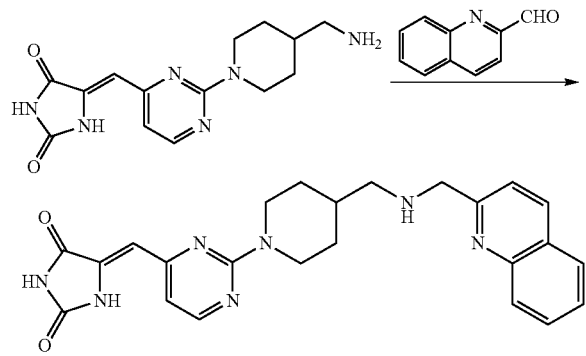

(Z)-5-((2-(4-(((quinolin-2-ylmethyl)amino)methyl)piperidin-1-yl)pyrimidin-4-yl)methylene)imidazolidine-2,4-dione: A 2 dram round bottomed vial was charged with (Z)-5-((2-(4-(aminomethyl)piperidin-1-yl)pyrimidin-4-yl)methylene)imidazolidine-2,4-dione (17 mg, 0.056 mmol), quinoline-2-carbaldehyde (8.84 mg, 0.056 mmol, 1 equiv.), diisopropylethylamine (0.1 mL, 0.573 mmol, 10 equiv.), and DMSO (1 mL). The reaction mixture was shaken for 1 h at room temperature then treated with sodium triacetoxyhydroborate (23.83 mg, 0.112 mmol, 2 equiv.) and DCM (0.5 mL). The reaction mixture was shaken overnight. The sample was then filtered through a 0.45 micron syringe filter. The DMSO solution was purified using reverse phase HPLC (MS-triggered fraction collection) with an acetonitrile/water gradient and trifluoroacetic acid as the modifier. The pure fractions were then concentrated under reduced pressure (Genevac HT-4) to provide the desired product (3.2 mg, 24.9 mg theoretical, 12.8%). LC-MS m/z 444 (M+1).

Example 69

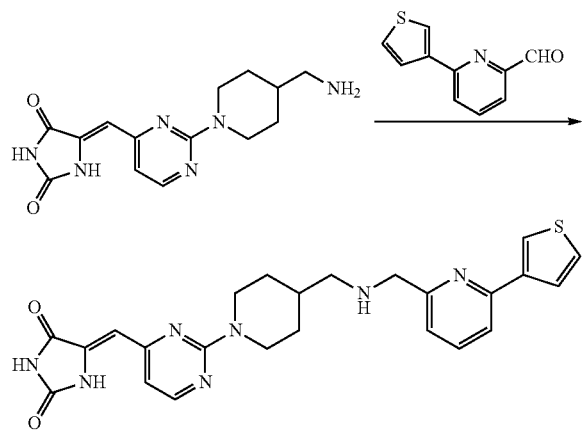

(Z)-5-((2-(4-(((6-(thiophen-3-yl)pyridin-2-yl)methyl)amino)methyl)piperidin-1-yl)pyrimidin-4-yl)methylene)imidazolidine-2,4-dione: A 2 dram round bottomed vial was charged with (Z)-5-((2-(4-(aminomethyl)piperidin-1-yl)pyrimidin-4-yl)methylene)imidazolidine-2,4-dione (17 mg, 0.056 mmol), 6-(thiophen-3-yl)picolinaldehyde (10.64 mg, 0.056 mmol, 1 equiv.), diisopropylethylamine (0.1 mL, 0.573 mmol, 10 equiv.), and DMSO (1 mL). The reaction mixture was shaken for 1 h at room temperature then treated with sodium triacetoxyhydroborate (23.83 mg, 0.112 mmol, 2 equiv.) and DCM (0.5 mL). The reaction mixture was shaken overnight. The sample was then filtered through a 0.45 micron syringe filter. The DMSO solution was purified using reverse phase HPLC (MS-triggered fraction collection) with an acetonitrile/water gradient and trifluoroacetic acid as the modifier. The pure fractions were then concentrated under reduced pressure (Genevac HT-4) to provide the desired product (9.8 mg, 26.7 mg theoretical, 36%). LC-MS m/z 476 (M+1).

Example 70

Protocols for Kinase Activity Screening for CK1γ1(h), CK1γ2 (h), CK1γ3 (h), CK1δ (h) and CK1(y): Kinase dilution buffer composition: 20 mM MOPS, 1 mM EDTA, 0.01% Brij-35, 5% Glycerol, 0.1% b-mercaptoethanol, 1 mg/mL BSA.

TABLE 4

Kinase assay ATP concentration within 15 µM of $K_M$

| Kinase | $K_M$ (µM) |
| --- | --- |
| CK1γ1 (h) | 15 |
| CK1γ2 (h) | 10 |
| CK1γ3 (h) | 10 |
| CK1δ (h) | 70 |
| CK1 (y) | 45 |

In a final reaction volume of 25 µL, the compound of interest (at the desired concentration) and the appropriate kinase (5-10 mU) were incubated with 8 mM MOPS pH 7.0, 0.2 mM EDTA, 200 µM KRRRALS(p)VASLPGL, 10 mM magnesium acetate and [γ-33P-ATP] (specific activity approx. 500 cpm/pmol, concentration as required). The reaction was initiated by the addition of the MgATP mix. After incubation for 40 minutes at room temperature, the reaction was stopped by the addition of 5 µL of a 3% phosphoric acid solution. 10 µL of the reaction mixture was then spotted onto a P30 filtermat; and washed three times for 5 minutes in 75 mM phosphoric acid, and once in methanol prior to drying and scintillation counting. Tables 5, 6 and 7 show the relative activity of CK1γ1(h), CK1γ2(h), and CK1γ3(h), at varying concentrations of compound 5114.

TABLE 5

Relative activity of CK1γ1(h) at varying concentration of compound 5114.
ATP Concentration: 15 µM

| Sample | Counts | Mean (Counts − Blanks) | Activity (% Control) | Mean | SD* |
| --- | --- | --- | --- | --- | --- |
| 5114 @ 0.001 µM | 10040 | 9047 | 105 | / | / |
| 5114 @ 0.003 µM | 10254 | 9261 | 108 | / | / |
| 5114 @ 0.01 µM | 9722 | 8729 | 102 | / | / |
| 5114 @ 0.03 µM | 8374 | 7381 | 86 | / | / |
| 5114 @ 0.1 µM | 6373 | 5380 | 63 | / | / |
| 5114 @ 0.3 µM | 4497 | 3504 | 41 | / | / |
| 5114 @ 1 µM | 3259 | 2266 | 26 | / | / |
| 5114 @ 3 µM | 3658 | 2665 | 31 | / | / |

TABLE 5-continued

Relative activity of CK1γ1(h) at varying concentration of compound 5114.
ATP Concentration: 15 μM

| Sample | Counts | Mean (Counts – Blanks) | Activity (% Control) | Mean | SD* |
|---|---|---|---|---|---|
| 5114 @ 10 μM | 4178 | 3185 | 37 | / | / |
| CONTROL | 9207 | 8582 | 96 | 100 | 6 |
|  | 9195 |  | 96 |  |  |
|  | 9668 |  | 101 |  |  |
|  | 10233 |  | 108 |  |  |
| BLANK | 908 | / | / | / | / |
|  | 1079 |  | / |  |  |

*NB. Where n = 2, the value reported here is actually range/√2

TABLE 6

Relative activity of CK1γ2(h) at varying concentration of compound 5114.
ATP Concentration: 10 μM

| Sample | Counts | Mean (Counts – Blanks) | Activity (% Control) | Mean | SD* |
|---|---|---|---|---|---|
| 5114 @ 0.001 μM | 7649 | 7041 | 98 | / | / |
| 5114 @ 0.003 μM | 7313 | 6705 | 94 | / | / |
| 5114 @ 0.01 μM | 5658 | 5050 | 71 | / | / |
| 5114 @ 0.03 μM | 4532 | 3924 | 55 | / | / |
| 5114 @ 0.1 μM | 2530 | 1922 | 27 | / | / |
| 5114 @ 0.3 μM | 1328 | 720 | 10 | / | / |
| 5114 @ 1 μM | 746 | 138 | 2 | / | / |
| 5114 @ 3 μM | 839 | 231 | 3 | / | / |
| 5114 @ 10 μM | 998 | 390 | 5 | / | / |
| CONTROL | 8112 | 7156 | 105 | 100 | 10 |
|  | 7521 |  | 97 |  |  |
|  | 8510 |  | 110 |  |  |
|  | 6912 |  | 88 |  |  |
| BLANK | 582 | / | / | / | / |
|  | 634 |  | / |  |  |

*NB. Where n = 2, the value reported here is actually range/√2

TABLE 7

Relative activity of CK1γ3(h) at varying concentration of compound 5114.
ATP Concentration: 10 μM

| Sample | Counts | Mean (Counts- Blanks) | Activity (% Control) | Mean | SD* |
|---|---|---|---|---|---|
| 5114 @ 0.001 μM | 9610 | 9389 | 88 | / | / |
| 5114 @ 0.003 μM | 8980 | 8759 | 82 | / | / |
| 5114 @ 0.01 μM | 8181 | 7960 | 75 | / | / |
| 5114 @ 0.03 μM | 8141 | 7920 | 75 | / | / |
| 5114 @ 0.1 μM | 7310 | 7089 | 67 | / | / |
| 5114 @ 0.3 μM | 6004 | 5783 | 54 | / | / |
| 5114 @ 1 μM | 3320 | 3099 | 29 | / | / |
| 5114 @ 3 μM | 2477 | 2256 | 21 | / | / |
| 5114 @ 10 μM | 3459 | 3238 | 30 | / | / |
| CONTROL | 11003 | 10623 | 101 | 100 | 2 |
|  | 10644 |  | 98 |  |  |
|  | 11024 |  | 102 |  |  |
|  | 10708 |  | 99 |  |  |
| BLANK | 190 | / | / | / | / |
|  | 253 |  | / |  |  |

*NB. Where n = 2, the value reported here is actually range/√2

Tables 8-10 show the relative activity of CK1γ2(h) at varying concentration of compounds 5132, 5124, and 5336.

TABLE 8

Relative activity of CK1γ2(h) at varying concentration of compound 5132.
ATP Concentration: 10 μM

| Sample | Counts | Mean (Counts - Blanks) | Activity (% Control) | Mean | SD* |
|---|---|---|---|---|---|
| 5132 @ 0.001 μM | 9557 | 8769 | 97 | / | / |
| 5132 @ 0.003 μM | 9228 | 8440 | 93 | / | / |
| 5132 @ 0.01 μM | 8663 | 7875 | 87 | / | / |
| 5132 @ 0.03 μM | 7659 | 6871 | 76 | / | / |
| 5132 @ 0.1 μM | 5435 | 4647 | 51 | / | / |
| 5132 @ 0.3 μM | 2963 | 2175 | 24 | / | / |
| 5132 @ 1 μM | 1453 | 665 | 7 | / | / |
| 5132 @ 3 μM | 929 | 141 | 2 | / | / |
| 5132 @ 10 μM | 747 | −41 | 0 | / | / |
| CONTROL | 9907 | 9040 | 101 | 100 | 1 |
|  | 9751 |  | 99 |  |  |
|  | 9916 |  | 101 |  |  |
|  | 9736 |  | 99 |  |  |
| BLANK | 741 | / | / | / | / |
|  | 835 |  | / |  |  |

*NB. Where n = 2, the value reported here is actually range/√2

TABLE 9

Relative activity of CK1γ2(h) at varying concentration of compound 5124.
ATP Concentration: 10 μM

| Sample | Counts | Mean (Counts - Blanks) | Activity (% Control) | Mean | SD* |
|---|---|---|---|---|---|
| 5124 @ 0.001 μM | 9126 | 8301 | 97 | / | / |
| 5124 @ 0.003 μM | 9311 | 8486 | 100 | / | / |
| 5124 @ 0.01 μM | 9458 | 8633 | 101 | / | / |
| 5124 @ 0.03 μM | 8389 | 7564 | 89 | / | / |
| 5124 @ 0.1 μM | 7007 | 6182 | 73 | / | / |
| 5124 @ 0.3 μM | 5630 | 4805 | 56 | / | / |
| 5124 @ 1 μM | 2827 | 2002 | 23 | / | / |
| 5124 @ 3 μM | 1644 | 819 | 10 | / | / |
| 5124 @ 10 μM | 1122 | 297 | 3 | / | / |
| CONTROL | 9210 | 8521 | 98 | 100 | 2 |
|  | 9429 |  | 101 |  |  |
|  | 9560 |  | 103 |  |  |
|  | 9186 |  | 98 |  |  |
| BLANK | 806 | / | / | / | / |
|  | 844 |  | / |  |  |

*NB. Where n = 2, the value reported here is actually range/√2

TABLE 10

Relative activity of CK1γ2(h) at varying concentration of compound 5336.
ATP Concentration: 10 μM

| Sample | Counts | Mean (Counts - Blanks) | Activity (% Control) | Mean | SD* |
|---|---|---|---|---|---|
| 5336 @ 0.001 μM | 9228 | 8450 | 95 | / | / |
| 5336 @ 0.003 μM | 9511 | 8733 | 98 | / | / |
| 5336 @ 0.01 μM | 9197 | 8419 | 94 | / | / |
| 5336 @ 0.03 μM | 9091 | 8313 | 93 | / | / |
| 5336 @ 0.1 μM | 8538 | 7760 | 87 | / | / |
| 5336 @ 0.3 μM | 8060 | 7282 | 81 | / | / |
| 5336 @ 1 μM | 5306 | 4528 | 51 | / | / |
| 5336 @ 3 μM | 4439 | 3661 | 41 | / | / |

TABLE 10-continued

Relative activity of CK1γ2(h) at varying
concentration of compound 5336.
ATP Concentration: 10 μM

| Sample | Counts | Mean (Counts - Blanks) | Activity (% Control) | Mean | SD* |
|---|---|---|---|---|---|
| 5336 @ 10 μM | 2029 | 1251 | 14 | / | / |
| CONTROL | 9855 | 8938 | 102 | 100 | 2 |
|  | 9697 |  | 100 |  |  |
|  | 9853 |  | 102 |  |  |
|  | 9459 |  | 97 |  |  |
| BLANK | 750 | / | / | / | / |
|  | 806 |  | / |  |  |

*NB. Where n = 2, the value reported here is actually range/√2

Tables 11-14 show the relative activity of CK1(y) at varying concentrations of compounds 5347, 5343, 5363 and 5378

TABLE 11

Relative activity of CK1(y) at varying
concentration of compound 5347.
ATP Concentration: 45 μM

| Sample | Counts | Mean (Counts - Blanks) | Activity (% Control) | Mean | SD* |
|---|---|---|---|---|---|
| 5347 @ 0.001 μM | 7648 | 6881 | 109 | / | / |
| 5347 @ 0.003 μM | 7504 | 6737 | 107 | / | / |
| 5347 @ 0.01 μM | 5664 | 4897 | 78 | / | / |
| 5347 @ 0.03 μM | 5743 | 4976 | 79 | / | / |
| 5347 @ 0.1 μM | 5564 | 4797 | 76 | / | / |
| 5347 @ 0.3 μM | 5163 | 4396 | 70 | / | / |
| 5347 @ 1 μM | 5328 | 4561 | 72 | / | / |
| 5347 @ 3 μM | 5835 | 5068 | 80 | / | / |
| 5347 @ 10 μM | 5163 | 4396 | 70 | / | / |
| CONTROL | 7344 | 6308 | 104 | 100 | 9 |
|  | 6256 |  | 87 |  |  |
|  | 7622 |  | 109 |  |  |
|  | 7079 |  | 100 |  |  |
| BLANK | 699 | / | / | / | / |
|  | 835 |  | / |  |  |

*NB. Where n = 2, the value reported here is actually range/√2

TABLE 12

Relative activity of CK1(y) at varying
concentration of compound 5343.
ATP Concentration: 45 μM

| Sample | Counts | Mean (Counts - Blanks) | Activity (% Control) | Mean | SD* |
|---|---|---|---|---|---|
| 5343 @ 0.001 μM | 7851 | 7158 | 98 | / | / |
| 5343 @ 0.003 μM | 7723 | 7030 | 96 | / | / |
| 5343 @ 0.01 μM | 7857 | 7164 | 98 | / | / |
| 5343 @ 0.03 μM | 7773 | 7080 | 97 | / | / |
| 5343 @ 0.1 μM | 7344 | 6651 | 91 | / | / |
| 5343 @ 0.3 μM | 7239 | 6546 | 89 | / | / |
| 5343 @ 1 μM | 6649 | 5956 | 81 | / | / |
| 5343 @ 3 μM | 5523 | 4830 | 66 | / | / |
| 5343 @ 10 μM | 5370 | 4677 | 64 | / | / |
| CONTROL | 8329 | 7328 | 104 | 100 | 3 |
|  | 7923 |  | 99 |  |  |
|  | 8055 |  | 100 |  |  |
|  | 7778 |  | 97 |  |  |
| BLANK | 651 | / | / | / | / |
|  | 736 |  | / |  |  |

*NB. Where n = 2, the value reported here is actually range/√2

TABLE 13

Relative activity of CK1(y) at varying
concentration of compound 5363.
ATP Concentration: 45 μM

| Sample | Counts | Mean (Counts - Blanks) | Activity (% Control) | Mean | SD* |
|---|---|---|---|---|---|
| 5363 @ 0.001 μM | 5899 | 5159 | 108 | / | / |
| 5363 @ 0.003 μM | 6009 | 5269 | 111 | / | / |
| 5363 @ 0.01 μM | 6326 | 5586 | 117 | / | / |
| 5363 @ 0.03 μM | 6257 | 5517 | 116 | / | / |
| 5363 @ 0.1 μM | 5857 | 5117 | 107 | / | / |
| 5363 @ 0.3 μM | 6019 | 5279 | 111 | / | / |
| 5363 @ 1 μM | 5675 | 4935 | 104 | / | / |
| 5363 @ 3 μM | 6071 | 5331 | 112 | / | / |
| 5363 @ 10 μM | 5837 | 5097 | 107 | / | / |
| CONTROL | 5646 | 4764 | 103 | 100 | 6 |
|  | 5081 |  | 91 |  |  |
|  | 5723 |  | 105 |  |  |
|  | 5566 |  | 101 |  |  |
| BLANK | 696 | / | / | / | / |
|  | 785 |  | / |  |  |

*NB. Where n = 2, the value reported here is actually range/√2

TABLE 14

Relative activity of CK1(y) at varying
concentration of compound 5378.
ATP Concentration: 45 μM

| Sample | Counts | Mean (Counts - Blanks) | Activity (% Control) | Mean | SD* |
|---|---|---|---|---|---|
| 5378 @ 0.001 μM | 5556 | 4772 | 101 | / | / |
| 5378 @ 0.003 μM | 6095 | 5311 | 113 | / | / |
| 5378 @ 0.01 μM | 6043 | 5259 | 112 | / | / |
| 5378 @ 0.03 μM | 6327 | 5543 | 118 | / | / |
| 5378 @ 0.1 μM | 6481 | 5697 | 121 | / | / |
| 5378 @ 0.3 μM | 6601 | 5817 | 124 | / | / |
| 5378 @ 1 μM | 5981 | 5197 | 111 | / | / |
| 5378 @ 3 μM | 5886 | 5102 | 108 | / | / |
| 5378 @ 10 μM | 5553 | 4769 | 101 | / | / |
| CONTROL | 5836 | 4702 | 107 | 100 | 6 |
|  | 5392 |  | 98 |  |  |
|  | 5532 |  | 101 |  |  |
|  | 5187 |  | 94 |  |  |
| BLANK | 711 | / | / | / | / |
|  | 858 |  | / |  |  |

*NB. Where n = 2, the value reported here is actually range/√2

Table 15 summarizes the activity of several casein kinases at 10 μmol concentration of several compounds.

TABLE 15

|  | CK1γ1(h) | CK1γ2(h) | CK1γ3(h) | CK1δ1(h) | CK1y |
|---|---|---|---|---|---|
| 5113 | 58 | 25 | 46 | 84 | 64 |
| 5117 | 64 | 50 | 70 | 101 | 55 |
| 5121 | 37 | 19 | 25 | 85 | 81 |
| 5126 | 46 | 43 | 40 | 85 | 99 |
| 5132 | 19 | 7 | 31 | 82 | 111 |
| 5114 | 24 | 15 | 47 | 88 | 115 |
| 5118 | 41 | 17 | 28 | 83 | 99 |
| 5122 | 86 | 60 | 104 | 103 | 105 |
| 5127 | 56 | 52 | 83 | 89 | 115 |
| 5133 | 54 | 47 | 48 | 92 | 106 |
| 5115 | 81 | 93 | 81 | 98 | 107 |
| 5119 | 78 | 71 | 61 | 100 | 104 |
| 5124 | 12 | 4 | 26 | 75 | 114 |
| 5128 | 61 | 29 | 53 | 100 | 95 |
| 5116 | 92 | 98 | 67 | 98 | 32 |
| 5120 | 92 | 104 | 72 | 89 | 94 |
| 5125 | 64 | 28 | 68 | 103 | 108 |

TABLE 15-continued

| | CK1γ1(h) | CK1γ2(h) | CK1γ3(h) | CK1δ1(h) | CK1γ |
|---|---|---|---|---|---|
| 5131 | 70 | 85 | 52 | 94 | 54 |
| 5336 | 31 | 8 | 47 | 101 | 90 |
| 5337 | 92 | 109 | 73 | 107 | 49 |
| 5338 | 93 | 96 | 105 | 106 | 92 |
| 5339 | 76 | 51 | 58 | 103 | 36 |
| 5340 | 40 | 24 | 51 | 94 | 80 |
| 5345 | 73 | 62 | 99 | 107 | 88 |
| 5349 | 86 | 83 | 82 | 107 | 113 |
| 5353 | 83 | 122 | 71 | 110 | 76 |
| 5358 | 80 | 74 | 75 | 105 | 98 |
| 5341 | 83 | 100 | 87 | 107 | 107 |
| 5346 | 41 | 16 | 61 | 97 | 114 |
| 5350 | 66 | 76 | 40 | 94 | 93 |
| 5354 | 28 | 11 | 56 | 97 | 101 |
| 5343 | 67 | 54 | 61 | 104 | 4 |
| 5347 | 80 | 85 | 91 | 103 | 1 |
| 5351 | 50 | 10 | 53 | 102 | 2 |
| 5355 | 81 | 74 | 69 | 102 | 88 |
| 5344 | 84 | 98 | 86 | 104 | 92 |
| 5348 | 85 | 80 | 102 | 96 | 31 |
| 5352 | 105 | 96 | 86 | 108 | 1 |
| 5357 | 81 | 70 | 78 | 105 | 18 |
| 5359 | 76 | 81 | 54 | 102 | 85 |
| 5376 | 99 | 91 | 76 | 99 | 91 |
| 5382 | 87 | 78 | 58 | 100 | 93 |
| 5363 | 60 | 67 | 29 | 83 | 0 |
| 5378 | 66 | 68 | 37 | 91 | 1 |
| 5369 | 94 | 78 | 74 | 87 | 1 |
| 5379 | 89 | 71 | 44 | 96 | 92 |
| 5371 | 106 | 92 | 88 | 98 | 81 |
| 5380 | 105 | 96 | 86 | 96 | 107 |

The estimated $IC_{50}$ values for several compounds are provided in Table 16.

TABLE 16

Estimated IC50 values.

| Compound | Kinase | IC50 (nM) |
|---|---|---|
| 5114 | CK1γ1(h) | 165 |
| 5114 | CK1γ2(h) | 31 |
| 5114 | CK1γ3(h) | 307 |
| 5132 | CK1γ2(h) | 114 |
| 5124 | CK1γ2(h) | 349 |
| 5336 | CK1γ2(h) | 1,600 |
| 5347 | CK1 | >10,000 |
| 5343 | CK1 | >10,000 |
| 5363 | CK1 | >10,000 |
| 5378 | CK1 | >10,000 |

Figure 2:
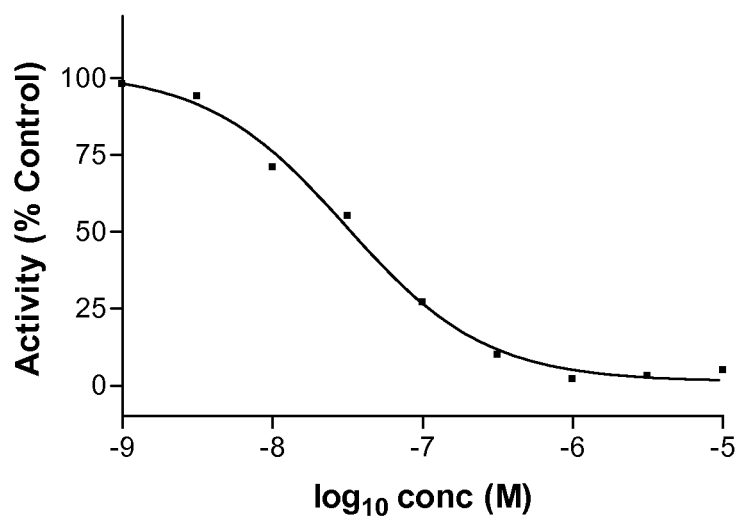
FIG. 2 depicts the relative activity of CK1γ2(h) as a function of the concentration of compound 5114.
Figure 3:
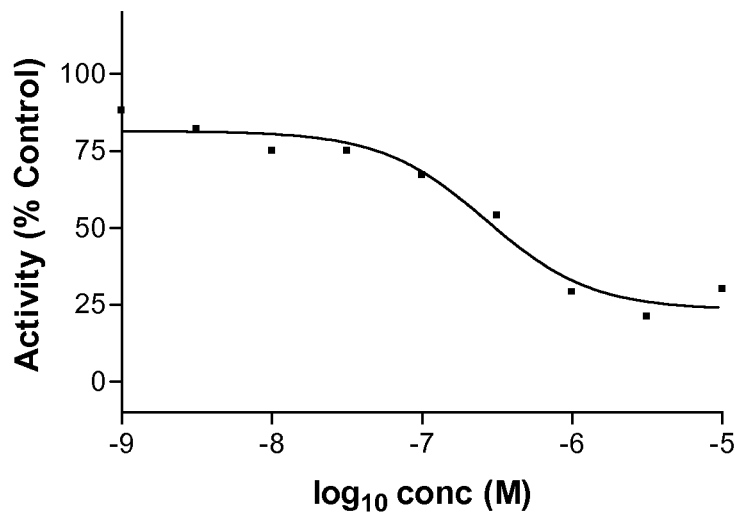
FIG. 3 depicts the relative activity of CK1γ3(h) as a function of the concentration of compound 5114.
Figure 4:
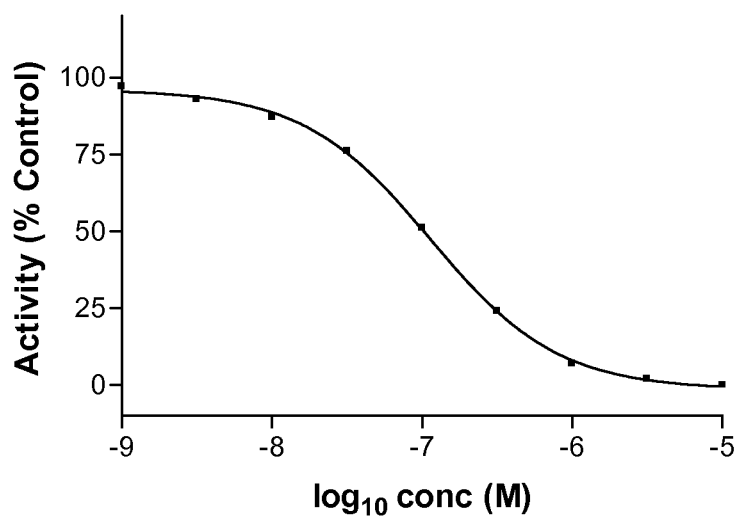
FIG. 4 depicts the relative activity of CK1γ2(h) as a function of the concentration of compound 5132.
Figure 5:
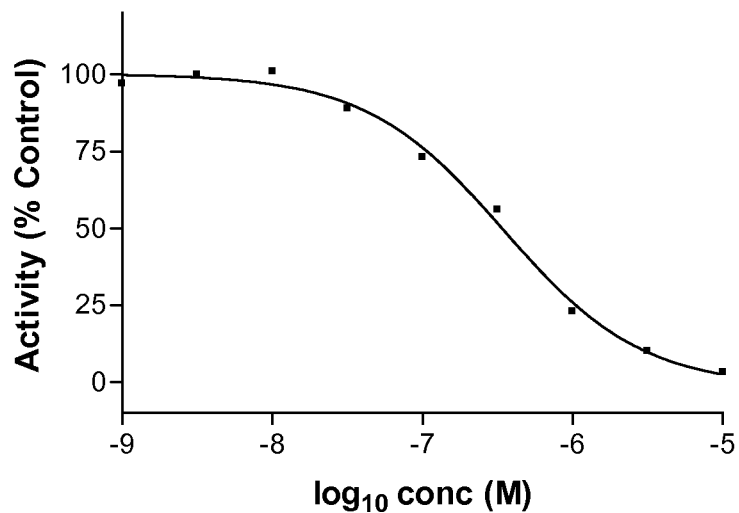
FIG. 5 depicts the relative activity of CK1γ2(h) as a function of the concentration of compound 5124.
Figure 6:
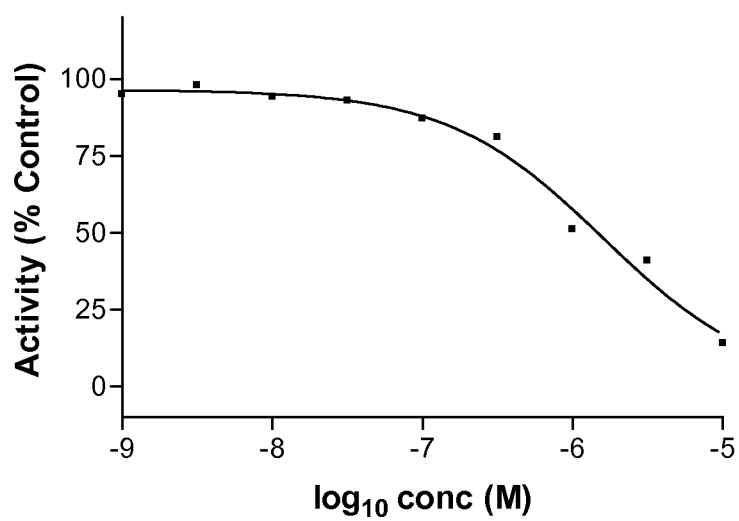
FIG. 6 depicts the relative activity of CK1γ2(h) as a function of the concentration of compound 5336.
Figure 7:
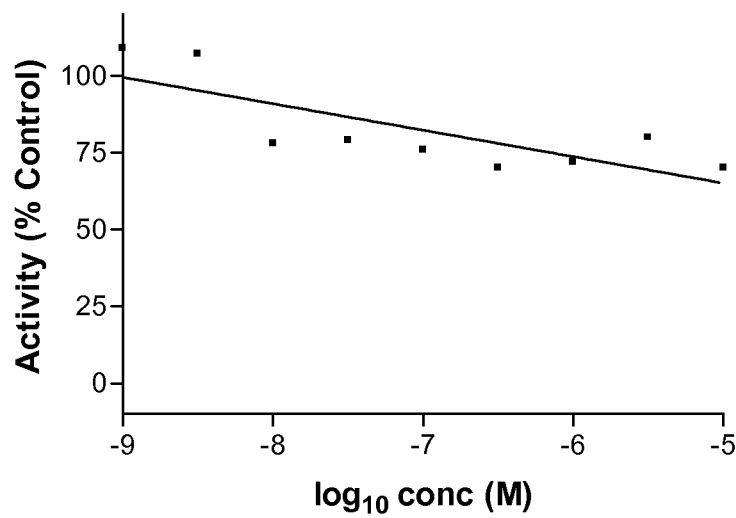
FIG. 7 depicts the relative activity of CK1γ as a function of the concentration of compound 5347.
Figure 8:
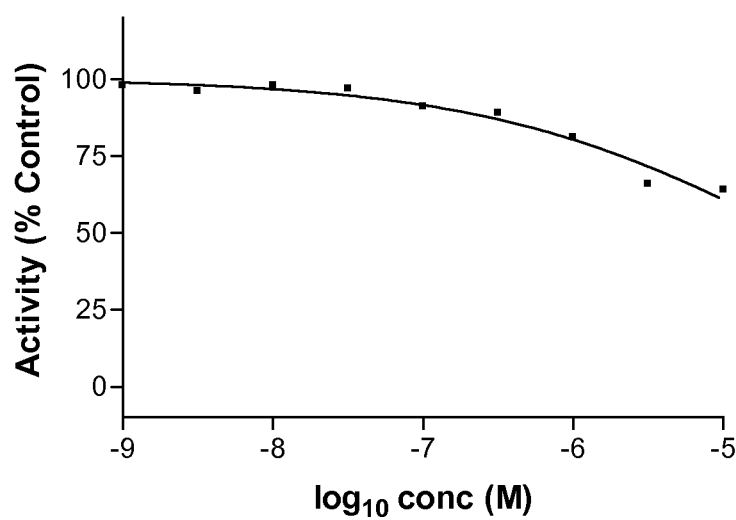
FIG. 8 depicts the relative activity of CK1γ as a function of the concentration of compound 5343.
Figure 9:
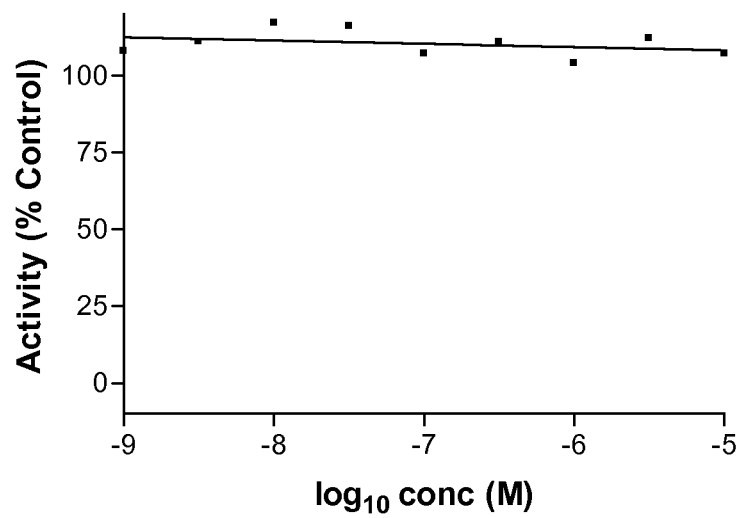
FIG. 9 depicts the relative activity of CK1γ as a function of the concentration of compound 5363.
Figure 10:
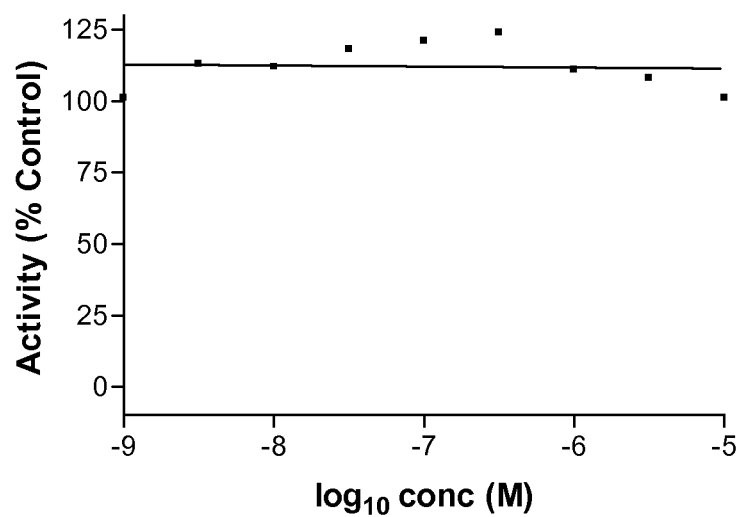
FIG. 10 depicts the relative activity of CK1γ as a function of the concentration of compound 5378.

The relative activity of the kinase as a function of the concentration of several compounds is depicted in FIGS. 1-10.

Example 71

Cell Proliferation Studies

Cell proliferation studies are summarized in Tables 17 and 18:

TABLE 17

| No. | CK1γ2† | PAMPA (Pe) | HCT-116‡ | HCT-116* | A549‡ | DU145‡ | DU145* | MDA-MB-468‡ | MDA-MB-468* |
|---|---|---|---|---|---|---|---|---|---|
| 5114 | 31 | 14 | 0.8 | 20.64 | 5.4 | 38.8 | 31.75 | | x |
| 5124 | 349 | x | 4.6 | x | −0.7 | 6.1 | x | | x |
| 5132 | 114 | x | 4.5 | x | −1.2 | 23.2 | 59.6 | | X |
| 5336 | 1,600 | x | 3.5 | x | −0.7 | 11.3 | x | | x |
| 5343 | 10,000 | x | 3.3 | x | −0.9 | −1.2 | x | | x |
| 5347 | 10,000 | x | 5.7 | x | −2.6 | 12.7 | x | | X |
| 5363 | 10,000 | x | 5.7 | x | −4.3 | −18.4 | x | | x |
| A | x | x | x | 1.29 | x | x | 1.28 | x | 3.34 |
| B | x | x | x | x | x | x | x | X | xx |

A: Gemicitabine control
B: Sorafenib control
†IC50 (μM)
‡% at 10 μM
*50% inhibition concentration

TABLE 18

| No. | HCC 1954‡ | Caco-2* | PC-3‡ | PC-3* | OVCAR-3‡ | OVCAR-3* | LNCaP‡ | LNCaP* | Jurkat‡ |
|---|---|---|---|---|---|---|---|---|---|
| 5114 | −8.1 | x | 3.6 | x | 4.3 | 64.3 | −0.2 | 51.52 | 43.4 |
| 5124 | −17.3 | x | −7.1 | x | 12.5 | x | 9.6 | x | 21.3 |
| 5132 | 6.7 | x | −18.9 | x | −5.8 | x | −0.4 | 73.53 | −23.8 |
| 5336 | −4.9 | x | −15.1 | x | −15.1 | x | 0.1 | x | 28.1 |
| 5343 | −7.2 | x | −9.7 | x | −24.2 | x | −8.5 | x | 18.9 |
| 5347 | 0.2 | x | −5.5 | x | −6.9 | x | −12.5 | x | 27.3 |
| 5363 | −8.9 | x | −2.6 | x | −57.4 | x | −12.2 | x | 41.2 |
| A | x | x | x | 41.32 | x | 11.2 | x | 1.97 | 3.2 |
| B | x | 8.78 | x | x | x | x | x | x | x |

A: Gemicitabine control
B: Sorafenib control
‡% at 10 μM
*50% inhibition concentration Inhibition of Caco-2 Cells
Cells: Caco-2 cells, ATCC Passage 33, *Mycoplasma* free.
Medium: DMEM Medium (GIBCO Cat #11995073) supplemented with 10% fetal bovine serum (Hyclone Cat #SH30396.03).
Seeding: 3,000 cells/well (100 μL) into 96-wells plate, incubated overnight at 37° C. in a humidified, 5% CO2 atmosphere.
Treatment: Test compounds and Sorafenib were prepared in a serial dilution (1:2) by culture medium. Fifty microliters (50 μL) of diluted compounds were added into each well. The final concentrations of the positive control and test compounds were shown in the graphs. The cells were incubated for 72 hours after addition of the test compounds.
MTS: 15 uL of MTS solution (Promega Cat #G5430) was added into each well and incubated with cells for 4 hours at 37° C. in a humidified, 5% CO2 atmosphere.
Measurement: Absorbance at 490 nm was measured using MD Spectramax Plus384 spectrophotometer. The regression curves were calculated by the GraphPad Prism 5 using "log (inhibitor) vs response—variable slope".
Calculation: % of inhibition=(ODzero ctrl−OD compound)/ODzero ctrl*100. Results are shown in table 19.

TABLE 19

| Compound ID | IC50 NO. | Concentration (μM) | OD value 1 | OD value 2 | % of inhibition 1 | % of inhibition 2 |
|---|---|---|---|---|---|---|
| 5114 | 5 | 0.000 | 0.557 | 0.584 | 0.00 | 0.00 |
|  |  | 0.400 | 0.557 | 0.527 | −0.04 | 9.74 |
|  |  | 0.800 | 0.536 | 0.567 | 3.77 | 2.96 |
|  |  | 1.600 | 0.557 | 0.619 | 0.02 | −5.97 |
|  |  | 3.200 | 0.627 | 0.596 | −12.57 | −2.05 |
|  |  | 6.250 | 0.521 | 0.633 | 6.43 | −8.41 |
|  |  | 12.500 | 0.467 | 0.606 | 16.16 | −3.66 |
|  |  | 25.000 | 0.452 | 0.544 | 18.94 | 6.95 |
|  |  | 50.000 | 0.414 | 0.463 | 25.73 | 20.73 |
|  |  | 100.000 | 0.420 | 0.461 | 24.58 | 21.01 |
| 5124 | 6 | 0.000 | 0.608 | 0.640 | 0.00 | 0.00 |
|  |  | 0.400 | 0.558 | 0.626 | 1.63 | 2.19 |
|  |  | 0.800 | 0.489 | 0.553 | 3.14 | 13.46 |
|  |  | 1.600 | 0.619 | 0.586 | −1.88 | 8.30 |
|  |  | 3.200 | 0.606 | 0.657 | 0.33 | −2.77 |
|  |  | 6.250 | 0.543 | 0.555 | 2.47 | 13.29 |
|  |  | 12.500 | 0.597 | 0.522 | 1.73 | 18.37 |
|  |  | 25.000 | 0.570 | 0.557 | 6.17 | 12.93 |
|  |  | 50.000 | 0.532 | 0.507 | 12.52 | 20.03 |
|  |  | 100.000 | 0.428 | 0.446 | 29.67 | 30.30 |
| 5132 | 7 | 0.000 | 0.600 | 0.619 | 0.00 | 0.00 |
|  |  | 0.400 | 0.578 | 0.573 | 3.63 | 7.44 |
|  |  | 0.800 | 0.535 | 0.618 | 7.53 | 0.18 |
|  |  | 1.600 | 0.549 | 0.646 | 8.60 | −4.33 |
|  |  | 3.200 | 0.607 | 0.616 | −1.22 | 0.48 |
|  |  | 6.250 | 0.591 | 0.622 | 1.52 | −0.39 |
|  |  | 12.500 | 0.572 | 0.622 | 4.77 | −0.39 |
|  |  | 25.000 | 0.593 | 0.663 | 1.13 | −7.09 |
|  |  | 50.000 | 0.581 | 0.604 | 3.13 | 2.42 |
|  |  | 100.000 | 0.592 | 0.595 | 1.37 | 3.89 |
| Sorafenib | 8 | 0.000 | 0.619 | 0.697 | 0.000 | 0.000 |
|  |  | 0.400 | 0.618 | 0.695 | 0.049 | 0.315 |
|  |  | 0.800 | 0.557 | 0.654 | 9.975 | 6.237 |
|  |  | 1.600 | 0.530 | 0.618 | 14.292 | 11.442 |
|  |  | 3.200 | 0.513 | 0.632 | 17.008 | 9.392 |
|  |  | 6.250 | 0.496 | 0.534 | 19.886 | 23.457 |
|  |  | 12.500 | 0.144 | 0.166 | 76.762 | 76.265 |
|  |  | 25.000 | (0.003) | 0.010 | 100.463 | 98.503 |
|  |  | 50.000 | (0.015) | 0.007 | 102.371 | 99.020 |
|  |  | 100.000 | 0.099 | 0.023 | 84.053 | 96.668 |

Inhibition of DU145 Cells
Cells: DU145 cells, ATCC Passage unknown, *Mycoplasma* free.
Medium: DMEM Medium (GIBCO Cat #11995073) supplemented with 10% fetal bovine serum (Hyclone Cat #SH30396.03).
Seeding: 750 cells/well (100 μL) into 96-wells plate, incubated overnight at 37° C. in a humidified, 5% CO2 atmosphere.
Treatment: Test compounds and Gemcitabine were prepared in a serial dilution (1:2) by culture medium. Fifty microliters (50 uL) of serially diluted solutions were added into each well. The final concentrations of the positive control and test compounds were shown in the graphs. The cells were incubated for 72 hours after addition of the test compounds.
MTS: 15 uL of MTS solution (Promega Cat #G5430) was added into each well and incubated with cells for 4 hours at 37° C. in a humidified, 5% CO2 atmosphere.
Measurement: Absorbance at 490 nm was measured using MD Spectramax Plus384 spectrophotometer. The regression curves were calculated by the GraphPad Prism 5 using "log (inhibitor) vs response—variable slope".
Calculation: % of inhibition=(ODzero ctrl−OD compound)/ODzero ctrl*100 Results are shown in Table 20.

TABLE 20

| Compound ID | IC50 NO. | Concentration (uM) | OD value 1 | OD value 2 | % of inhibition 1 | % of inhibition 2 |
|---|---|---|---|---|---|---|
| 5114 | 5 | 0.000 | 1.066 | 1.001 | 0.00 | 0.00 |
|  |  | 0.400 | 1.060 | 0.981 | 0.53 | 1.99 |
|  |  | 0.800 | 1.122 | 0.873 | −5.24 | 12.76 |
|  |  | 1.600 | 0.887 | 0.966 | 16.79 | 3.54 |
|  |  | 3.200 | 0.967 | 0.937 | 9.32 | 6.41 |
|  |  | 6.250 | 0.819 | 0.851 | 23.21 | 15.02 |
|  |  | 12.500 | 0.670 | 0.793 | 37.17 | 20.75 |
|  |  | 25.000 | 0.461 | 0.481 | 56.73 | 51.92 |
|  |  | 50.000 | 0.420 | 0.442 | 60.60 | 55.86 |
|  |  | 100.000 | 0.327 | 0.336 | 69.34 | 66.47 |
| 5124 | 6 | 0.000 | 1.006 | 1.011 | 0.00 | 0.00 |
|  |  | 0.400 | 1.018 | 1.023 | −1.21 | −1.28 |
|  |  | 0.800 | 0.957 | 0.943 | 4.86 | 6.68 |
|  |  | 1.600 | 0.985 | 0.910 | 2.10 | 9.96 |
|  |  | 3.200 | 0.967 | 0.861 | 3.86 | 14.79 |
|  |  | 6.250 | 0.892 | 0.880 | 11.37 | 12.96 |
|  |  | 12.500 | 0.927 | 0.976 | 7.89 | 3.41 |
|  |  | 25.000 | 0.932 | 0.956 | 7.32 | 5.35 |
|  |  | 50.000 | 0.948 | 0.845 | 5.73 | 16.39 |
|  |  | 100.000 | 0.791 | 0.768 | 21.41 | 24.06 |
| 5132 | 7 | 0.000 | 1.217 | 1.070 | 0.00 | 0.00 |
|  |  | 0.400 | 0.993 | 0.981 | 18.37 | 8.34 |
|  |  | 0.800 | 1.080 | 1.020 | 11.22 | 4.67 |
|  |  | 1.600 | 1.000 | 0.902 | 17.86 | 15.71 |
|  |  | 3.200 | 1.043 | 0.943 | 14.27 | 11.95 |
|  |  | 6.250 | 1.016 | 0.948 | 16.49 | 11.42 |
|  |  | 12.500 | 0.904 | 0.904 | 25.67 | 15.54 |
|  |  | 25.000 | 0.695 | 0.723 | 42.88 | 32.45 |
|  |  | 50.000 | 0.591 | 0.631 | 51.42 | 41.09 |
|  |  | 100.000 | 0.555 | 0.494 | 54.41 | 53.82 |
| Gemcitabine | 8 | 0.000 | 1.1367875 | 1.042 | 0.000 | 0.000 |
|  |  | 0.400 | 0.9392875 | 0.880 | 17.374 | 15.551 |
|  |  | 0.800 | 0.7368875 | 0.699 | 35.178 | 32.934 |
|  |  | 1.600 | 0.4662875 | 0.477 | 58.982 | 54.261 |
|  |  | 3.200 | 0.0513875 | 0.039 | 95.480 | 96.223 |
|  |  | 6.250 | 0.0359875 | 0.039 | 96.834 | 96.223 |
|  |  | 12.500 | 0.0385875 | 0.028 | 96.606 | 97.297 |
|  |  | 25.000 | 0.0345875 | 0.040 | 96.957 | 96.203 |
|  |  | 50.000 | 0.0299875 | 0.012 | 97.362 | 98.870 |
|  |  | 100.000 | 0.0235875 | 0.029 | 97.925 | 97.172 |

Inhibition of HCT116 Cells
Cells: HCT116 cells, ATCC Passage unknown, *Mycoplasma* free.
Medium: DMEM Medium (GIBCO Cat #11995073) supplemented with 10% fetal bovine serum (Hyclone Cat #SH30396.03).
Seeding: 750 cells/well (100 μL) into 96-wells plate, incubated overnight at 37° C. in a humidified, 5% CO2 atmosphere.

Treatment: Test compounds and Gemcitabine were prepared in a serial dilution (1:2) by culture medium. Fifty microliters (50 uL) of serially diluted solutions were added into each well. The final concentrations of the positive control and test compounds were shown in the graphs. The cells were incubated for 72 hours after addition of the test compounds.

MTS: 15 uL of MTS solution (Promega Cat #G5430) was added into each well and incubated with cells for 4 hours at 37° C. in a humidified, 5% CO2 atmosphere.

Measurement: Absorbance at 490 nm was measured using MD Spectramax Plus384 spectrophotometer. The regression curves were calculated by the GraphPad Prism 5 using "log (inhibitor) vs response—variable slope".

Calculation: % of inhibition=(ODzero ctrl−OD compound)/ODzero ctrl*100. Results are shown in Table 21.

TABLE 21

| Compound ID | IC50 NO. | Concentration (uM) | OD value 1 | OD value 2 | % of inhibition 1 | % of inhibition 2 |
|---|---|---|---|---|---|---|
| 5114 | 5 | 0.000 | 0.766 | 0.964 | 0.00 | 0.00 |
|  |  | 0.400 | 0.707 | 0.936 | 7.74 | 2.98 |
|  |  | 0.800 | 0.671 | 0.972 | 12.43 | −0.80 |
|  |  | 1.600 | 0.709 | 0.862 | 7.49 | 10.57 |
|  |  | 3.200 | 0.654 | 0.816 | 14.72 | 15.37 |
|  |  | 6.250 | 0.747 | 0.888 | 2.53 | 7.91 |
|  |  | 12.500 | 0.664 | 0.803 | 13.36 | 16.69 |
|  |  | 25.000 | 0.217 | 0.270 | 71.62 | 72.02 |
|  |  | 50.000 | 0.145 | 0.163 | 81.12 | 83.12 |
|  |  | 100.000 | 0.141 | 0.139 | 81.56 | 85.60 |
| 5124 | 6 | 0.000 | 0.812 | 0.904 | 0.00 | 0.00 |
|  |  | 0.400 | 0.760 | 0.882 | 6.37 | 2.40 |
|  |  | 0.800 | 0.758 | 1.016 | 6.59 | −12.40 |
|  |  | 1.600 | 0.761 | 0.865 | 6.19 | 4.34 |
|  |  | 3.200 | 0.731 | 0.844 | 9.98 | 6.58 |
|  |  | 6.250 | 0.768 | 0.894 | 5.41 | 1.08 |
|  |  | 12.500 | 0.763 | 0.879 | 6.05 | 2.73 |
|  |  | 25.000 | 0.722 | 0.796 | 11.05 | 11.89 |
|  |  | 50.000 | 0.644 | 0.834 | 20.69 | 7.77 |
|  |  | 100.000 | 0.635 | 0.766 | 21.74 | 15.28 |
| 5132 | 7 | 0.000 | 0.798 | 0.860 | 0.00 | 0.00 |
|  |  | 0.400 | 0.750 | 0.920 | 5.97 | −6.93 |
|  |  | 0.800 | 0.859 | 0.878 | −7.71 | −2.01 |
|  |  | 1.600 | 0.799 | 0.872 | −0.15 | −1.36 |
|  |  | 3.200 | 0.834 | 0.791 | −4.53 | 8.02 |
|  |  | 6.250 | 0.822 | 0.740 | −3.03 | 13.95 |
|  |  | 12.500 | 0.801 | 0.747 | −0.40 | 13.15 |
|  |  | 25.000 | 0.732 | 0.663 | 8.27 | 22.98 |
|  |  | 50.000 | 0.648 | 0.628 | 18.74 | 27.03 |
|  |  | 100.000 | 0.580 | 0.630 | 27.24 | 26.79 |
| Gemcitabine | 8 | 0.000 | 0.985 | 0.968 | 0.00 | 0.00 |
|  |  | 0.400 | 0.799 | 0.766 | 18.84 | 20.88 |
|  |  | 0.800 | 0.619 | 0.723 | 37.19 | 25.28 |
|  |  | 1.600 | 0.452 | 0.535 | 54.10 | 44.71 |
|  |  | 3.200 | 0.083 | 0.083 | 91.60 | 91.43 |
|  |  | 6.250 | 0.076 | 0.065 | 92.29 | 93.27 |
|  |  | 12.500 | 0.065 | 0.063 | 93.39 | 93.46 |
|  |  | 25.000 | 0.075 | 0.061 | 92.39 | 93.66 |
|  |  | 50.000 | 0.036 | 0.046 | 96.36 | 95.22 |
|  |  | 100.000 | 0.037 | 0.037 | 96.28 | 96.22 |

Inhibition of PC-3 Cells:
Cells: PC-3 cells, ATCC Passage unknown, *Mycoplasma* free.
Medium: DMEM Medium (GIBCO Cat #11995073) supplemented with 10% fetal bovine serum (Hyclone Cat #SH30396.03).
Seeding: 3,000 cells/well (100 ul) into 96-wells plate, incubated overnight at 37° C. in a humidified, 5% CO2 atmosphere.
Treatment: Test compounds and Gemcitabine were prepared in a serial dilution (1:2) by culture medium. Fifty microliters (50 uL) of serially diluted solutions were added into each well. The final concentrations of the positive control and test compounds were shown in the graphs. The cells were incubated for 72 hours after addition of the test compounds.
MTS: 15 uL of MTS solution (Promega Cat #G5430) was added into each well and incubated with cells for 4 hours at 37° C. in a humidified, 5% CO2 atmosphere.
Measurement: Absorbance at 490 nm was measured using MD Spectramax Plus384 spectrophotometer. The regression curves were calculated by the GraphPad Prism 5 using "log (inhibitor) vs response—variable slope".
Calculation: % of inhibition=(ODzero ctrl−OD compound)/ODzero ctrl*100. Results are shown in table 22.

TABLE 22

| Compound ID | IC50 NO. | Concentration (uM) | OD value 1 | OD value 2 | % of inhibition 1 | % of inhibition 2 |
|---|---|---|---|---|---|---|
| 5114 | 5 | 0.000 | 0.776 | 0.848 | 0.00 | 0.00 |
|  |  | 0.400 | 0.817 | 0.814 | −5.35 | 3.99 |
|  |  | 0.800 | 0.782 | 0.786 | −0.89 | 7.32 |
|  |  | 1.600 | 0.721 | 0.736 | 7.03 | 13.20 |
|  |  | 3.200 | 0.735 | 0.726 | 5.17 | 14.31 |
|  |  | 6.250 | 0.685 | 0.735 | 11.63 | 13.27 |
|  |  | 12.500 | 0.761 | 0.738 | 1.84 | 12.92 |
|  |  | 25.000 | 0.683 | 0.650 | 11.91 | 23.26 |
|  |  | 50.000 | 0.562 | 0.562 | 27.57 | 33.69 |
|  |  | 100.000 | 0.391 | 0.492 | 49.54 | 41.90 |
| 5124 | 6 | 0.000 | 0.811 | 0.675 | 0.00 | 0.00 |
|  |  | 0.400 | 0.829 | 0.630 | −2.24 | 6.67 |
|  |  | 0.800 | 0.836 | 0.728 | −3.14 | −7.90 |
|  |  | 1.600 | 0.725 | 0.682 | 10.56 | −1.11 |
|  |  | 3.200 | 0.813 | 0.718 | −0.25 | −6.45 |
|  |  | 6.250 | 0.698 | 0.743 | 13.97 | −10.18 |
|  |  | 12.500 | 0.819 | 0.695 | −0.94 | −3.05 |
|  |  | 25.000 | 0.756 | 0.703 | 6.75 | −4.18 |
|  |  | 50.000 | 0.692 | 0.655 | 14.71 | 2.96 |
|  |  | 100.000 | 0.839 | 0.721 | −3.43 | −6.83 |
| 5132 | 7 | 0.000 | 0.854 | 0.743 | 0.00 | 0.00 |
|  |  | 0.400 | 0.817 | 0.680 | 4.29 | 8.53 |
|  |  | 0.800 | 0.850 | 0.759 | 0.42 | −2.17 |
|  |  | 1.600 | 0.827 | 0.745 | 3.11 | −0.23 |
|  |  | 3.200 | 0.842 | 0.728 | 1.36 | 2.07 |
|  |  | 6.250 | 0.794 | 0.783 | 7.03 | −5.42 |
|  |  | 12.500 | 0.815 | 0.787 | 4.58 | −5.89 |
|  |  | 25.000 | 0.771 | 0.768 | 9.66 | −3.36 |
|  |  | 50.000 | 0.793 | 0.694 | 7.11 | 6.64 |
|  |  | 100.000 | 0.893 | 0.771 | −4.53 | −3.77 |
| Gemcitabine | 8 | 0.000 | 0.903 | 0.883 | 0.00 | 0.00 |
|  |  | 0.400 | 0.884 | 0.866 | 2.10 | 1.92 |
|  |  | 0.800 | 0.860 | 0.803 | 4.80 | 9.05 |
|  |  | 1.600 | 0.794 | 0.778 | 12.00 | 11.91 |
|  |  | 3.200 | 0.726 | 0.756 | 19.70 | 14.35 |
|  |  | 6.250 | 0.686 | 0.692 | 24.10 | 21.66 |
|  |  | 12.500 | 0.617 | 0.628 | 31.70 | 28.93 |
|  |  | 25.000 | 0.572 | 0.583 | 36.70 | 33.96 |
|  |  | 50.000 | 0.458 | 0.488 | 49.30 | 44.46 |
|  |  | 100.000 | 0.246 | 0.214 | 72.80 | 75.81 |

Inhibition of LNCaP Cells
Cells: LNCaP, ATCC Passage unknown, *Mycoplasma* free.
Medium: RPMI-1640 Medium (GIBCO Cat #22400121) supplemented with 10% fetal bovine serum (Hyclone Cat #SH30396.03).
Seeding: 3,000 cells/well (100 uL) into 96-wells plate, incubated overnight at 37° C. in a humidified, 5% CO2 atmosphere.
Treatment: Test compounds and Gemcitabine were prepared in a serial dilution (1:2) by culture medium. Fifty microliters (50 uL) of serially diluted solutions were added into each well. The final concentrations of the positive control and test compounds were shown in the graphs. The cells were incubated for 72 hours after addition of the test compounds.
MTS: 15 uL of MTS solution (Promega Cat #G5430) was added into each well and incubated with cells for 4 hours at 37° C. in a humidified, 5% CO2 atmosphere.

Measurement: Absorbance at 490 nm was measured using MD Spectramax Plus384 spectrophotometer. The regression curves were calculated by the GraphPad Prism 5 using "log (inhibitor) vs response—variable slope".
Calculation: % of inhibition+(AVE zero ctrl−AVE compound)/AVE zero ctrl*100. Results are shown in Table 23:

TABLE 23

| Compound ID | IC50 NO. | Concentration (uM) | OD value 1 | OD value 2 | % of inhibition 1 | % of inhibition 2 |
|---|---|---|---|---|---|---|
| 5114 | 5 | 0.000 | 0.630 | 0.687 | 0.00 | 0.00 |
| | | 0.400 | 0.609 | 0.688 | 3.33 | −0.15 |
| | | 0.800 | 0.541 | 0.593 | 14.12 | 13.69 |
| | | 1.600 | 0.568 | 0.594 | 9.84 | 13.54 |
| | | 3.200 | 0.558 | 0.638 | 11.43 | 7.13 |
| | | 6.250 | 0.560 | 0.593 | 11.11 | 13.69 |
| | | 12.500 | 0.537 | 0.602 | 14.76 | 12.37 |
| | | 25.000 | 0.471 | 0.496 | 25.23 | 27.81 |
| | | 50.000 | 0.306 | 0.386 | 51.42 | 43.82 |
| | | 100.000 | 0.164 | 0.195 | 73.95 | 71.63 |
| 5124 | 6 | 0.000 | 0.615 | 0.710 | 0.00 | 0.00 |
| | | 0.400 | 0.604 | 0.687 | 1.79 | 3.24 |
| | | 0.800 | 0.523 | 0.602 | 14.96 | 15.21 |
| | | 1.600 | 0.593 | 0.643 | 3.58 | 9.44 |
| | | 3.200 | 0.538 | 0.636 | 12.52 | 10.42 |
| | | 6.250 | 0.556 | 0.614 | 9.59 | 13.52 |
| | | 12.500 | 0.556 | 0.636 | 9.59 | 10.42 |
| | | 25.000 | 0.577 | 0.588 | 6.18 | 17.19 |
| | | 50.000 | 0.592 | 0.641 | 3.74 | 9.72 |
| | | 100.000 | 0.615 | 0.651 | 0.00 | 8.31 |
| 5132 | 7 | 0.000 | 0.693 | 0.752 | 0.00 | 0.00 |
| | | 0.400 | 0.668 | 0.753 | 3.61 | −0.13 |
| | | 0.800 | 0.645 | 0.679 | 6.93 | 9.71 |
| | | 1.600 | 0.675 | 0.724 | 2.60 | 3.72 |
| | | 3.200 | 0.653 | 0.706 | 5.77 | 6.12 |
| | | 6.250 | 0.639 | 0.705 | 7.79 | 6.25 |
| | | 12.500 | 0.658 | 0.712 | 5.05 | 5.32 |
| | | 25.000 | 0.678 | 0.681 | 2.16 | 9.44 |
| | | 50.000 | 0.600 | 0.625 | 13.42 | 16.89 |
| | | 100.000 | 0.322 | 0.333 | 53.53 | 55.73 |
| Gemcitabine | 8 | 0.000 | 0.663 | 0.766 | 0.00 | 0.00 |
| | | 0.400 | 0.578 | 0.662 | 12.82 | 13.58 |
| | | 0.800 | 0.459 | 0.434 | 30.76 | 43.35 |
| | | 1.600 | 0.448 | 0.472 | 32.42 | 38.39 |
| | | 3.200 | 0.322 | 0.337 | 51.42 | 56.01 |
| | | 6.250 | 0.182 | 0.190 | 72.54 | 75.21 |
| | | 12.500 | 0.166 | 0.173 | 74.95 | 77.43 |
| | | 25.000 | 0.101 | 0.177 | 84.75 | 76.91 |
| | | 50.000 | 0.124 | 0.202 | 81.28 | 73.64 |
| | | 100.000 | 0.112 | 0.197 | 83.09 | 74.29 |

Inhibition of MDA-MB-468 Cells
Cells: MDA-MB-468 cells, ATCC Passage unknown, *Mycoplasma* free.
Medium: RPMI-1640 Medium (GIBCO Cat #22400121) supplemented with 10% fetal bovine serum (Hyclone Cat #SH30396.03).
Seeding: 2,000 cells/well (100 ul) into 96-wells plate, incubated overnight at 37° C. in a humidified, 5% CO2 atmosphere.
Treatment: Test compounds and Gemcitabine were prepared in a serial dilution (1:2) by culture medium. Fifty microliters (50 uL) of serially diluted solutions were added into each well. The final concentrations of the positive control and test compounds were shown in the graphs. The cells were incubated for 72 hours after addition of the test compounds.
MTS: 15 uL of MTS solution (Promega Cat #G5430) was added into each well and incubated with cells for 4 hours at 37° C. in a humidified, 5% CO2 atmosphere.
Measurement: Absorbance at 490 nm was measured using MD Spectramax Plus384 spectrophotometer. The regression curves were calculated by the GraphPad Prism 5 using "log (inhibitor) vs response—variable slope".

Calculation: % of inhibition=(ODzero ctrl−OD compound)/ODzero ctrl*100 Results are shown in Table 24:

TABLE 24

| Compound ID | IC50 NO. | Concentration (μM) | OD value 1 | OD value 2 | % of inhibition 1 | % of inhibition 2 |
|---|---|---|---|---|---|---|
| 5114 | 5 | 0.000 | 0.381 | 0.391 | 0.00 | 0.00 |
| | | 0.400 | 0.352 | 0.332 | 7.61 | 15.08 |
| | | 0.800 | 0.351 | 0.317 | 7.88 | 18.91 |
| | | 1.600 | 0.342 | 0.373 | 10.24 | 4.60 |
| | | 3.200 | 0.303 | 0.335 | 20.48 | 14.31 |
| | | 6.250 | 0.282 | 0.290 | 25.99 | 25.81 |
| | | 12.500 | 0.292 | 0.295 | 23.37 | 24.53 |
| | | 25.000 | 0.257 | 0.249 | 32.56 | 36.28 |
| | | 50.000 | 0.250 | 0.267 | 34.39 | 31.68 |
| | | 100.000 | 0.252 | 0.246 | 33.87 | 37.05 |
| 5124 | 6 | 0.000 | 0.347 | 0.343 | 0.00 | 0.00 |
| | | 0.400 | 0.317 | 0.347 | 8.65 | −1.16 |
| | | 0.800 | 0.326 | 0.306 | 6.05 | 10.78 |
| | | 1.600 | 0.374 | 0.350 | −7.78 | −2.04 |
| | | 3.200 | 0.281 | 0.358 | 19.03 | −4.37 |
| | | 6.250 | 0.303 | 0.294 | 12.68 | 14.27 |
| | | 12.500 | 0.308 | 0.325 | 11.24 | 5.24 |
| | | 25.000 | 0.268 | 0.268 | 22.77 | 21.84 |
| | | 50.000 | 0.280 | 0.285 | 19.32 | 16.89 |
| | | 100.000 | 0.254 | 0.233 | 26.81 | 32.03 |
| 5132 | 7 | 0.000 | 0.378 | 0.378 | 0.00 | 0.00 |
| | | 0.400 | 0.315 | 0.353 | 16.67 | 6.61 |
| | | 0.800 | 0.341 | 0.332 | 9.79 | 12.16 |
| | | 1.600 | 0.315 | 0.345 | 16.67 | 8.72 |
| | | 3.200 | 0.315 | 0.337 | 16.67 | 10.84 |
| | | 6.250 | 0.318 | 0.312 | 15.88 | 17.44 |
| | | 12.500 | 0.293 | 0.324 | 22.49 | 14.27 |
| | | 25.000 | 0.291 | 0.328 | 23.02 | 13.21 |
| | | 50.000 | 0.360 | 0.402 | 4.76 | −6.34 |
| | | 100.000 | 0.430 | 0.385 | −13.76 | −1.85 |
| Gemcitabine | 8 | 0.000 | 0.333 | 0.341 | 0.00 | 0.00 |
| | | 0.400 | 0.313 | 0.337 | 6.01 | 1.17 |
| | | 0.800 | 0.275 | 0.310 | 17.42 | 9.08 |
| | | 1.600 | 0.201 | 0.264 | 39.65 | 22.56 |
| | | 3.200 | 0.151 | 0.192 | 54.68 | 43.65 |
| | | 6.250 | 0.101 | 0.105 | 69.70 | 69.13 |
| | | 12.500 | 0.066 | 0.053 | 80.21 | 84.36 |
| | | 25.000 | 0.033 | 0.035 | 90.12 | 89.64 |
| | | 50.000 | 0.064 | 0.064 | 80.81 | 81.14 |
| | | 100.000 | 0.034 | 0.007 | 89.82 | 97.84 |

Inhibition of Ovcar 3 Cells
Cells: Ovcar-3 cells, ATCC Passage 4, *Mycoplasma* free.
Medium: RPMI-1640 Medium (GIBCO Cat #22400121) supplemented with 10% fetal bovine serum (Hyclone Cat #SH30396.03).
Seeding: 3,000 cells/well (100 uL) were seeded into 96-wells plate, incubated overnight at 37° C. in a humidified, 5% CO2 atmosphere.
Treatment: Test compounds and Gemcitabine were prepared in a serial dilution (1:2) by culture medium. Fifty microliters (50 uL) of serially diluted solutions were added into each well. The final concentrations of the positive control and test compounds were shown in the graphs. The cells were incubated for 72 hours after addition of the test compounds.
MTS: 15 uL of MTS solution (Promega Cat #G5430) was added into each well and incubated with cells for 4 hours at 37° C. in a humidified, 5% CO2 atmosphere.
Measurement: Absorbance at 490 nm was measured using MD Spectramax Plus384 spectrophotometer. The regression curves were calculated by the GraphPad Prism 5 using "log (inhibitor) vs response—variable slope".
Calculation: % of inhibition=(ODzero ctrl−OD compound)/ODzero ctrl*100 Results are shown in Table 25:

TABLE 25

| Compound ID | IC50 NO. | Concentration (μM) | OD value 1 | OD value 2 | % of inhibition 1 | % of inhibition 2 |
|---|---|---|---|---|---|---|
| 5114 | 5 | 0.000 | 0.660 | 0.586 | 0.00 | 0.00 |
| | | 0.400 | 0.707 | 0.553 | −7.13 | 5.71 |
| | | 0.800 | 0.587 | 0.505 | 11.07 | 13.83 |
| | | 1.600 | 0.581 | 0.584 | 11.87 | 0.34 |
| | | 3.200 | 0.565 | 0.571 | 14.40 | 2.56 |
| | | 6.250 | 0.540 | 0.519 | 18.19 | 11.44 |
| | | 12.500 | 0.530 | 0.485 | 19.71 | 17.25 |
| | | 25.000 | 0.345 | 0.345 | 47.75 | 41.15 |
| | | 50.000 | 0.345 | 0.272 | 47.75 | 53.62 |
| | | 100.000 | 0.339 | 0.281 | 48.66 | 52.08 |
| 5124 | 6 | 0.000 | 0.605 | 0.567 | 0.00 | 0.00 |
| | | 0.400 | 0.609 | 0.553 | −0.79 | 2.45 |
| | | 0.800 | 0.557 | 0.471 | 7.94 | 16.94 |
| | | 1.600 | 0.464 | 0.521 | 23.32 | 8.12 |
| | | 3.200 | 0.533 | 0.480 | 11.91 | 15.35 |
| | | 6.250 | 0.439 | 0.423 | 27.46 | 25.41 |
| | | 12.500 | 0.497 | 0.453 | 17.86 | 20.12 |
| | | 25.000 | 0.364 | 0.346 | 39.86 | 39.00 |
| | | 50.000 | 0.353 | 0.384 | 41.68 | 32.30 |
| | | 100.000 | 0.263 | 0.351 | 56.56 | 38.12 |
| 5132 | 7 | 0.000 | 0.560 | 0.552 | 0.00 | 0.00 |
| | | 0.400 | 0.575 | 0.451 | −2.68 | 18.31 |
| | | 0.800 | 0.557 | 0.467 | 0.54 | 15.41 |
| | | 1.600 | 0.492 | 0.511 | 12.15 | 7.43 |
| | | 3.200 | 0.551 | 0.526 | 1.61 | 4.71 |
| | | 6.250 | 0.464 | 0.485 | 17.15 | 12.15 |
| | | 12.500 | 0.645 | 0.550 | −15.19 | 0.36 |
| | | 25.000 | 0.542 | 0.563 | 3.22 | −1.99 |
| | | 50.000 | 0.600 | 0.574 | −7.15 | −3.99 |
| | | 100.000 | 0.567 | 0.531 | −1.26 | 3.81 |
| Gemcitabine | 8 | 0.000 | 0.600 | 0.548 | 0.00 | 0.00 |
| | | 0.400 | 0.591 | 0.575 | 1.50 | −4.93 |
| | | 0.800 | 0.490 | 0.460 | 18.34 | 16.07 |
| | | 1.600 | 0.440 | 0.453 | 26.64 | 17.35 |
| | | 3.200 | 0.411 | 0.432 | 31.52 | 21.18 |
| | | 6.250 | 0.363 | 0.388 | 39.52 | 29.22 |
| | | 12.500 | 0.257 | 0.234 | 57.20 | 57.34 |
| | | 25.000 | 0.040 | 0.009 | 93.39 | 98.43 |
| | | 50.000 | 0.020 | 0.010 | 96.73 | 98.09 |
| | | 100.000 | 0.012 | 0.011 | 97.97 | 98.02 |

A summary of the cell line data, including IC50's, 50% viability concentration and maximal inhibition % is provided in Table 26:

TABLE 26

| cell line | compound ID | IC50 (μM) | 50% viability conc. | Maximal inhibition % |
|---|---|---|---|---|
| Caco-2 | 5114 | 22.1 | N.D. | 22.8 |
| | 5124 | N.D. | 397.5 | N.D. |
| | 5132 | N.D. | N.D. | N.D. |
| | Sorafenib | 9.367 | 8.767 | 100 |
| DU145 | 5114 | N.D. | 31.75 | N.D. |
| | 5124 | N.D. | N.D. | N.D. |
| | 5132 | N.D. | 59.6 | N.D. |
| | Gemcitabine | 1.167 | 1.28 | 97.55 |
| HCT116 | 5114 | 13.6 | 20.64 | 83.58 |
| | 5124 | N.D. | N.D. | N.D. |
| | 5132 | N.D. | N.D. | N.D. |
| | Gemcitabine | 1.42 | 1.293 | 96.25 |
| PC-3 | 5114 | N.D. | 143.7 | N.D. |
| | 5124 | N.D. | N.D. | N.D. |
| | 5132 | N.D. | N.D. | N.D. |
| | Gemcitabine | N.D. | 41.32 | N.D. |
| LNCaP | 5114 | N.D. | 51.52 | N.D. |
| | 5124 | N.D. | N.D. | N.D. |
| | 5132 | N.D. | 73.53 | N.D. |
| | Gemcitabine | 2.38 | 1.967 | 78.69 |
| MDA-MB-468 | 5114 | 3.704 | N.D. | 38.46 |
| | 5124 | 17.48 | N.D. | 29.42 |
| | 5132 | N.D. | N.D. | N.D. |
| | Gemcitabine | 2.526 | 3.34 | 93.83 |
| Ovcar3 | 5114 | 13.97 | 64.28 | 50.37 |
| | 5124 | N.D. | 115.9 | N.D. |
| | 5132 | N.D. | N.D. | N.D. |
| | Gemcitabine | 9.871 | 11.18 | 98 |

Example 72

In Vitro ADME assays of PAMPA and human and rat hepatic microsomal stability. The generic gradient HPLC and MS method summarized in Table 27 was used for the analysis of compound 5114.

TABLE 27

| HPLC conditions. | | | |
|---|---|---|---|
| Instrument | Applied Biosystems API 4000 mass spectrometer | | |
| Ionization Mode | Electrospray, positive ions | | |
| MRM | 5114: 365.2→ 232.1 | | |
| Column | ACE 2 C18, 2.1 × 50 mm, 3 μmPart Number ACE-111-0502 | | |
| Eluent A | 2 mM ammonium acetate, 0.1% formic acid in 95:5 water:methanol | | |
| Eluent B | 2 mM ammonium acetate, 0.1% formic acid in 95:5 methanol:water | | |
| | Time (min) | % A | % B |
| Pump Gradient Program | 0 | 75 | 25 |
| | 0.50 | 75 | 25 |
| | 1.00 | 0 | 100 |
| | 2.00 | 0 | 100 |
| | 2.10 | 75 | 25 |
| | 2.50 | 75 | 25 |
| Flow (mL/min) | 0.5 | | |
| Column Temperature | Ambient | | |
| Injection Volume | 3-30 | | |
| Sample Temperature | Ambient | | |
| Run Time (min) | 2.5 | | |

Parallel artificial membrane permeability assays (PAMPA) were performed with compound 5114. The target concentration in the assay was 10 μM, prepared by diluting (1000-fold) the 10 mM stock solutions in DMSO into PBS, pH 7.4. The final DMSO concentration was 0.1%. The 10 μM solutions were added, 300 μL, to wells in the donor plate. The receiver plate, which contained 200 μL of PBS, pH 7.4 per well, was placed in the donor plate and the assembly was incubated for 5 hours at ambient temperature. At the end of the incubation period the plates were separated and the compound concentrations in each solution were determined by LC/MS/MS. The assay was performed in triplicate. Dexamethasone and verapamil were used as reference compounds. The permeability, Pc, and mass retention, R, of each compound were calculated using the following equations, and the results are summarized in Table 28. The results for dexamethsone and verapamil were consistent with historical data.

$$P_c = \frac{-\ln(1 - C_{A(t)}/C_E] \times 10^7}{A \times (1/V_D + 1/V_A) \times t}$$

$$R = 1 - \frac{C_{D(t)}V_D + C_{A(t)}V_A}{C_0 V_D}.$$

Where:
C0 is the initial concentration in the donor well (μM)
CD(t) is the concentration in the donor well after incubation (μM)
CA(t) is the concentration in the acceptor well after incubation (μM)
VD is the volume in the donor well (0.3 mL)
VA is the volume in the acceptor well (0.2 mL)
CE is (CD(t)VD+CA(t)VA)/(VD+VA)
A is the filter area (0.3 cm2)
t is the incubation time (18,000 s).

TABLE 28

PAMPA Assay data summary.

| Compound | Permeability $P_e$ (nm/s) | Mass Retention R (%) |
|---|---|---|
| 5114 | 14 | 0 |
| Verapamil | 75 | 20 |
| Dexamethasone | 9.0 | 9 |

Hepatic microsmal assays were performed with compound 5114 in human and rat (Sprague-Dawley). Protein concentrations of 0.4 (human) and 0.2 mg/mL (rat) with an NADPH regenerating cofactor system (2.6 mM NADP+, 6.6 mM glucose-6-phosphate, 0.8 U/mL glucose-6-phosphate dehydrogenase, and 6.6 mM magnesium chloride) were used. A 100 μM 20% DMSO/80% acetonitrile working stock of each of the compounds was diluted 100 fold resulting in 1 μM compound/1% final organic reaction concentrations. Time points were removed at 0 and 60 minutes. At each time point, 100 μL of the incubation suspension was added to 200 μL of acetonitrile containing internal standard (tolbutamide), followed by centrifugation at 3,220 rcf for 10 minutes. Two hundred (200) μL of the resulting supernatants were removed, dried under nitrogen and reconstituted in 100 μL of 2 mM ammonium acetate, 0.1% formic acid in 50% methanol prior to analysis by LC/MS/MS. Testosterone and dexamethasone were used as reference compounds. Table 29 summarizes the results. The results for testosterone and dexamethasone were consistent with historical data.

TABLE 29

Hepatic microsomal stability summary

| | % remaining after incubation | |
|---|---|---|
| Compound | Rat Microsomes | Human Microsomes |
| 5114 | 6.4 | 71 |
| Testosterone | 0.6 | 42 |
| Dexamethasone | 91 | 85 |

Materials used are summarized in Table 30.

TABLE 30

Materials.

| Material | Supplier | Part No. | Lot No. |
|---|---|---|---|
| Testosterone | Sigma | T1500 | 087K1440 |
| Dexamethasone | Sigma | D1756 | 096K1805 |
| Verapamil | Aldrich | 381195 | 12731MA |
| Tolbutamide | Sigma | T0891 | 076K1277 |
| PBS | Sigma | P3813 | 096K8204 |
| Ammonium acetate | J.T. Baker | 0599-08 | E49H15 |
| Formic acid | Acros Organics | 147930250 | AO266198 |
| Acetonitrile | EMD | AX0145-1 | 49099 |

TABLE 30-continued

Materials.

| Material | Supplier | Part No. | Lot No. |
|---|---|---|---|
| DMSO | Alfa Aeser | 32434 | D04R008 |
| Isopropanol | J.T. Baker | 9827-03 | C38H23 |
| Methanol | EMD | MX0486-1 | 49178 |
| 0.5M Potassium Phosphate pH 7.4 | BD Gentest | 451201 | 06123 |
| PAMPA plate | BD Gentest | 353015 | 431256 |
| Human microsomes | BD Gentest | 452161 | 18888 |
| Rat microsomes | BD Gentest | 452501 | 21027 |
| NADPH Regeneration System Solution A | BD Gentest | 451220 | 51893 |
| NADPH Regeneration System Solution B | BD Gentest | 451220 | 47758 |
| water | House DI (Barnstead Nanopure) | | |

LC/MS Equipment:
Chromatograph: Shimadzu LC-20 AD
Autosampler: CTC HTS PAL
MS: API 4000
Software System: Analyst Software, Version 1.4.2.

Example 73

Protocols for Kinase Activity Screening: Kinase screening was performed by Millipore UK Ltd. Kinase dilution buffer composition: 20 mM MOPS, 1 mM EDTA, 0.01% Brij-35, 5% Glycerol, 0.1% b-mercaptoethanol, 1 mg/mL BSA.
The percent kinase activity of different kinases is measured after treatment with various compounds listed in Table 31.

TABLE 31

Percent Kinase Activity of Enzyme When Treated with 300 nM of Compound

| Example | CK1g2 | CK1 | CK2 | Pim-1 | Pim-2 | Pim-3 |
|---|---|---|---|---|---|---|
| 64 | 75 | 81 | 65 | 83 | 81 | 97 |
| 65 | 96 | 97 | 94 | 92 | 78 | 76 |
| 66 | 77 | 98 | 78 | 91 | 86 | 96 |
| 67 | 111 | 104 | 94 | 98 | 99 | 114 |
| 68 | 84 | 97 | 109 | 75 | 69 | 63 |
| 69 | 76 | 92 | 106 | 46 | 86 | 59 |

Example 74

Selected Cell Proliferation Inhibition Data

LNCaP Cells
Cells: LNCaP, ATCC Passage unknown, *Mycoplasma* free.
Medium: RPMI-1640 Medium (GIBCO Cat #31800-022) supplemented with 10% fetal bovine serum (Hyclone Cat #SH30396.03).
Seeding: 3,000 cells/well (100 μL) into 96-well plates, incubated overnight at 37° C. in a humidified 5% CO$_2$ atmosphere.
DU145 Cells
Cells: DU145 cells, ATCC Passage unknown, *Mycoplasma* free.
Medium: DMEM Medium (GIBCO Cat #11995073) supplemented with 10% fetal bovine serum (Hyclone Cat #SH30396.03).
Seeding: 750 cells/well (100 μL) into 96-well plates, incubated overnight at 37° C. in a humidified 5% CO$_2$ atmosphere.
K562 Cells
Cells: K562, ATCC Passage unknown, *Mycoplasma* free.

Medium: RPMI-1640 Medium (GIBCO Cat #31800-022) supplemented with 10% fetal bovine serum (Hyclone Cat #SH30396.03).
Seeding: 3,000 cells/well (100 μL) into 96-well plates, incubated overnight at 37° C. in a humidified 5% CO$_2$ atmosphere.
MV4-11
Cells: MV4-11, ATCC Passage unknown, *Mycoplasma* free.
Medium: IMDM Medium (GIBCO Cat #31800-02231800-022) supplemented with 10% fetal bovine serum (Hyclone Cat #SH30396.03).
Seeding: 3,000 cells/well (100 μL) into 96-well plates, incubated overnight at 37° C. in a humidified 5% CO$_2$ atmosphere.
RPMI-8226
Cells: RPMI-8226, 3,000 cells/well (100 μL) into 96-well plates, incubated overnight at 37° C. in a humidified 5% CO$_2$ atmosphere.
Medium: RPMI-1640 Medium (GIBCO Cat #31800-022) supplemented with 10% fetal bovine serum (Hyclone Cat #SH30396.03).
Seeding: 3,000 cells/well (100 μL) into 96-well plates, incubated overnight at 37° C. in a humidified 5% CO$_2$ atmosphere.
Treatment: Test compounds were first diluted 333-fold in the medium. Fifty microliters (50 μL) of diluted compounds were added into each well (i.e., another 3-fold dilution). The final concentration of test compounds was 10 μM. The final concentrations of the positive control (Gemcitabine, also 50 μL) added in each well) is shown in FIG. 48. The cells were incubated for 72 hours after addition of the test compounds.
MTS: Added 20 μL of MTS solution (Promega Cat #G5430) into each well and incubated for 4 hours.
Measurement: Absorbance at 490 nm using MD Spectramax Plus 384 spectrophotometer.
Calculation: % of inhibition+(AVE zero ctrl−AVE compound)/AVE zero ctrl*100.

Table 32 shows 1050 values (μM) for the inhibition of specific cell lines using various compounds.

TABLE 32

| | Cell Proliferation Data (MTS) | | | | |
|---|---|---|---|---|---|
| COMPOUND | DU145 | LNCaP | K562 | MV4-11 | RPMI-8226 |
| 10641 | | | | | |
| 10642 | 10.07 | | | 13.35 | |
| 10643 | 20.34 | 15.38 | 47.83 | 6.76 | 7.47 |
| 10647 | | | | | |

INCORPORATION BY REFERENCE

All of the U.S. patents and U.S. published patent applications cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:
1. A compound of formula 1:

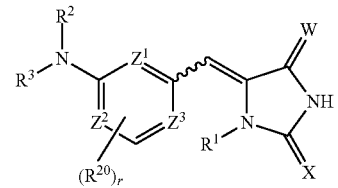

or a pharmaceutically acceptable salt thereof, wherein independently for each occurrence:

W and X are independently oxygen or sulfur;
$Z^1$, $Z^2$ and $Z^3$ are independently C—$R^{21}$ or N, provided that at least one of $Z^1$ and $Z^2$ is N;
$R^1$ is selected from the group consisting of hydrogen, alkyl, alkenyl, alkynyl, aralkyl, heteroaralkyl, —COR$^6$, and —C(O)OR$^6$;
$R^2$ is selected from the group consisting of alkyl, alkenyl, alkynyl, aryl, heteroaryl, heterocyclyl, aralkyl, heteroaralkyl, heterocyclylalkyl, —[C(R$^4$)$_2$]$_p$—R$^5$, —COR$^6$, —C(O)OR$^6$, —SO$_2$(R$^6$), —C(O)N(R$^6$)(R$^7$), —SO$_2$N(R$^6$)(R$^7$), —P(O)(OR$^6$)(OR$^7$);
$R^3$ is selected from the group consisting of hydrogen, alkyl, alkenyl, alkynyl, aryl, heteroaryl, heterocyclyl, aralkyl, heteroaralkyl, heterocyclylalkyl, —[C(R$^4$)$_2$]$_p$—R$^5$, —COR$^6$, —C(O)OR$^6$, —SO$_2$(R$^6$), —C(O)N(R$^6$)(R$^7$), —SO$_2$N(R$^6$)(R$^7$), —P(O)(OR$^6$)(OR$^7$); or $R^2$ and $R^3$ are joined together to form an optionally substituted heterocyclic ring;
$R^4$ is selected from the group consisting of hydrogen, alkyl, alkenyl, alkynyl, aryl, heterocyclylalkyl, aralkyl, heteroaryl, heteroaralkyl, halo, hydroxy, alkoxy, hydroxyalkyl, and alkoxyalkyl;
$R^5$ is selected from the group consisting of aryl, heteroaryl, heterocyclyl, —N(R$^8$)(R$^9$), —N(R$^8$)COR$^9$, —N(R$^8$)C(O)OR$^9$, —N(R$^8$)SO$_2$(R$^9$), —CON(R$^8$)(R$^9$), —OC(O)N(R$^8$)—(R$^9$), —SO$_2$N(R$^8$)(R$^9$), —OC(O)OR$^8$, —COOR$^9$, —C(O)N(OH)(R$^8$), —OS(O)$_2$OR$^8$, —S(O)$_2$OR$^8$, —S(O)$_2$R$^8$, —OR$^8$, —COR$^8$, —OP(O)(OR$^8$)(OR$^8$), —P(O)(OR$^8$)(OR$^8$) and —N(R$^8$)P(O)(OR$^9$)(OR$^9$);
p is 1, 2, 3, 4, 5, or 6;
$R^6$ is selected from the group consisting of hydrogen, alkyl, alkenyl, alkynyl, aryl, heteroaryl, heterocyclyl, aralkyl, heteroaralkyl, and heterocyclylalkyl;

R⁷ is selected from the group consisting of hydrogen, alkyl, alkenyl, alkynyl, aryl, heteroaryl, heterocyclyl, aralkyl, heteroaralkyl, and heterocyclylalkyl;

R⁸ is selected from the group consisting of hydrogen, alkyl, alkenyl, alkynyl, aryl, heteroaryl, heterocyclyl, aralkyl, heteroaralkyl, and heterocyclylalkyl;

R⁹ is selected from the group consisting of hydrogen, alkyl, alkenyl, alkynyl, aryl, heteroaryl, heterocyclyl, aralkyl, heteroaralkyl, and heterocyclylalkyl; or R⁸ and R⁹ are joined together to form a heterocyclic ring;

R²⁰ is selected from the group consisting of alkyl, alkenyl, alkynyl, aryl, heteroaryl, heterocyclyl, aralkyl, heteroaralkyl, heterocyclylalkyl, halo, haloalkyl, trifluoromethyl, fluoroalkyl, perfluoroalkyl, thio, cyano, hydroxy, methoxy, alkoxy, phenoxy, aryloxy, heteroaryloxy, carboxyl, alkoxycarbonyl, acyl, nitro, amino, alkylamino, arylamino, heteroarylamino, amido, acylamino, sulfate, sulfonate, sulfonyl, sulfoxido, sulfonamido, sulfamoyl, —[C(R⁴)₂]ₚ—R⁵, NR¹⁴R¹⁵, OR¹⁶, O—[C(R⁴)₂]ₚ—R⁵, NR¹⁴—[C(R⁴)₂]ₚ—R⁵ and SR¹⁶;

R²¹ is selected from the group consisting of hydrogen, alkyl, alkenyl, alkynyl, aryl, heteroaryl, heterocyclyl, aralkyl, heteroaralkyl, heterocyclylalkyl, halo, haloalkyl, thio, cyano, carboxyl, alkoxycarbonyl, acyl, nitro, amino, amido, acylamino, sulfate, sulfonate, sulfonyl, sulfoxido, sulfonamido, sulfamoyl, NR¹⁴R¹⁵, OR¹⁶, and SR¹⁶;

R¹⁴ and R¹⁵ are each independently selected from the group consisting of hydrogen, alkyl, alkenyl, alkynyl, aryl, heteroaryl, heterocyclyl, aralkyl, heteroaralkyl, heterocyclylalkyl, —[C(R⁴)₂]ₚ—R⁵, —COR⁶, —C(O)OR⁶, —SO₂(R⁶), —C(O)N(R⁶)(R⁷), —SO₂N(R⁶)(R⁷), and —P(O)(OR⁶)(OR⁷); or R¹⁴ and R¹⁵ are joined together to form an optionally substituted heterocyclic ring;

R¹⁶ is selected from the group consisting of hydrogen, alkyl, alkenyl, alkynyl, aryl, heteroaryl, heterocyclyl, aralkyl, heteroaralkyl, heterocyclylalkyl, —[C(R⁴)₂]ₚ—R⁵, —COR⁶, and —C(O)N(R⁶)(R⁷); and r is 0 or 1;

wherein any one of the aforementioned alkyl, alkenyl, alkynyl, aryl, heteroaryl, heterocyclyl, aralkyl, heteroaralkyl, and heterocyclylalkyl may be optionally substituted.

2. The compound of claim 1, wherein W and X are oxygen.

3. The compound of claim 1, wherein Z¹ and Z² are nitrogen; and Z³ is C—R²¹.

4. The compound of claim 1, wherein R¹ is hydrogen, alkyl, or aralkyl.

5. The compound of claim 1, wherein W and X are oxygen, Z¹ and Z² are each nitrogen, Z³ is C—R²¹, and R¹ is hydrogen, alkyl, or aralkyl.

6. The compound of claim 5, wherein R¹ is hydrogen.

7. The compound of claim 1, wherein R² and R³ are joined together to form an optionally substituted heterocyclic ring.

8. The compound of claim 7, wherein the optionally substituted heterocyclic ring is selected from the group consisting of piperazinyl, homopiperizinyl, pyrrolidinyl, piperidinyl, homopiperidinyl, morpholinyl, and quinolinyl.

9. The compound of claim 1, wherein R² is selected from the group consisting of alkyl, alkenyl, alkynyl, aryl, heteroaryl, heterocyclyl, —[C(R⁴)₂]ₚ—R⁵, —COR⁶, —C(O)OR⁶, —SO₂(R⁶), —C(O)N(R⁶)(R⁷), and —SO₂N(R⁶)(R⁷), and R³ is selected from the group consisting of hydrogen, alkyl, alkenyl, alkynyl, aryl, heteroaryl, heterocyclyl, —[C(R⁴)₂]ₚ—R⁵, —COR⁶, —C(O)OR⁶, —SO₂(R⁶), —C(O)N(R⁶)(R⁷), and —SO₂N(R⁶)(R⁷), wherein the alkyl, alkenyl, alkynyl, aryl, heteroaryl, and heterocyclyl may be optionally substituted.

10. The compound of claim 1, wherein R⁵ is aryl or heteroaryl, each of which may be optionally substituted.

11. A compound of formula 2:

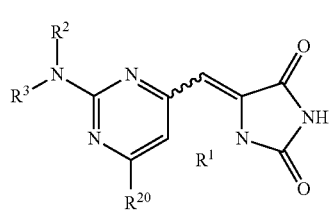

or a pharmaceutically acceptable salt thereof, wherein independently for each occurrence:

R¹ is selected from the group consisting of hydrogen, alkyl, alkenyl, alkynyl, aralkyl, heteroaralkyl, —COR⁶, and —C(O)OR⁶;

R² is selected from the group consisting of alkyl, alkenyl, alkynyl, aryl, heteroaryl, heterocyclyl, aralkyl, heteroaralkyl, heterocyclylalkyl, —[C(R⁴)₂]ₚ—R⁵, —COR⁶, —C(O)OR⁶, —SO₂(R⁶), —C(O)N(R⁶)(R⁷), —SO₂N(R⁶)(R⁷), —P(O)(OR⁶)(OR⁷);

R³ is selected from the group consisting of hydrogen, alkyl, alkenyl, alkynyl, aryl, heteroaryl, heterocyclyl, aralkyl, heteroaralkyl, heterocyclylalkyl, —[C(R⁴)₂]ₚ—R⁵, —COR⁶, —C(O)OR⁶, —SO₂(R⁶), —C(O)N(R⁶)(R⁷), —SO₂N(R⁶)(R⁷), —P(O)(OR⁶)(OR⁷); or R² and R³ are joined together to form an optionally substituted heterocyclic ring;

R⁴ is selected from the group consisting of hydrogen, alkyl, alkenyl, alkynyl, aryl, heterocyclylalkyl, aralkyl, heteroaryl, heteroaralkyl, halo, hydroxy, alkoxy, hydroxyalkyl, and alkoxyalkyl;

R⁵ is selected from the group consisting of aryl, heteroaryl, heterocyclyl, —N(R⁸)(R⁹), —N(R⁸)COR⁹, —N(R⁸)C(O)OR⁹, —N(R⁸)SO₂(R⁹), —CON(R⁸)(R⁹), —OC(O)N(R⁸)—(R⁹), —SO₂N(R⁸)(R⁹), —OC(O)OR⁸, —COOR⁹, —C(O)N(OH)(R⁸), —OS(O)₂OR⁸, —S(O)₂OR⁸, —S(O)₂R⁸, —OR⁸, —COR⁸, —OP(O)(OR⁸)(OR⁸), —P(O)(OR⁸)(OR⁸) and —N(R⁸)P(O)(OR⁹)(OR⁹);

p is 1, 2, 3, 4, 5, or 6;

R⁶ is selected from the group consisting of hydrogen, alkyl, alkenyl, alkynyl, aryl, heteroaryl, heterocyclyl, aralkyl, heteroaralkyl, and heterocyclylalkyl;

R⁷ is selected from the group consisting of hydrogen, alkyl, alkenyl, alkynyl, aryl, heteroaryl, heterocyclyl, aralkyl, heteroaralkyl, and heterocyclylalkyl;

R⁸ is selected from the group consisting of hydrogen, alkyl, alkenyl, alkynyl, aryl, heteroaryl, heterocyclyl, aralkyl, heteroaralkyl, and heterocyclylalkyl;

R⁹ is selected from the group consisting of hydrogen, alkyl, alkenyl, alkynyl, aryl, heteroaryl, heterocyclyl, aralkyl, heteroaralkyl, and heterocyclylalkyl; or R⁸ and R⁹ are joined together to form a heterocyclic ring; and R²⁰ is selected from the group consisting of hydrogen, alkyl, alkenyl, alkynyl, aryl, heteroaryl, heterocyclyl, aralkyl, heteroaralkyl, heterocyclylalkyl, halo, haloalkyl, trifluoromethyl, fluoroalkyl, perfluoroalkyl, thio, cyano, hydroxy, methoxy, alkoxy, phenoxy, aryloxy, heteroaryloxy, carboxyl, alkoxycarbonyl, acyl, nitro, amino, alkylamino, arylamino, heteroarylamino, amido, acylamino, sulfate, sulfonate, sulfonyl, sulfoxido, sulfonamido, sulfamoyl, —[C(R$^4$)$_2$]$_p$—R$^5$, NR$^{14}$R$^{15}$, OR$^{16}$, O—[C(R$^4$)$_2$]$_p$—R$^5$, NR$^{14}$—[C(R$^4$)$_2$]$_p$—R$^5$ and SR$^{16}$;

wherein any one of the aforementioned alkyl, alkenyl, alkynyl, aryl, heteroaryl, heterocyclyl, aralkyl, heteroaralkyl, and heterocyclylalkyl may be optionally substituted.

12. The compound of claim 11, wherein R$^1$ is hydrogen, alkyl, or aralkyl.

13. The compound of claim 11, wherein R$^2$ and R$^3$ are joined together to form an optionally substituted heterocyclic ring.

14. The compound of claim 13, wherein R$^2$ and R$^3$ are joined together to form an optionally substituted heterocyclic ring selected from the group consisting of:

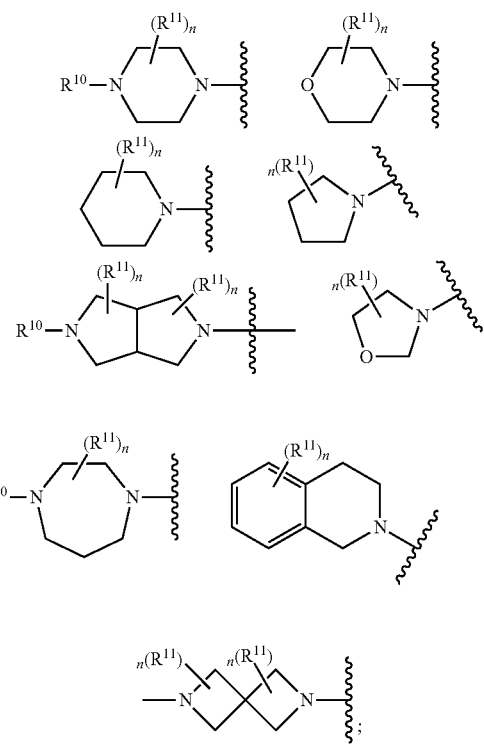

wherein, independently for each occurrence:

R$^{10}$ is selected from the group consisting of hydrogen, alkyl, alkenyl, alkynyl, aryl, heteroaryl, heterocyclyl, aralkyl, heteroaralkyl, heterocyclylalkyl, —[C(R$^4$)$_2$]$_p$—R$^5$, —COR$^6$, —C(O)OR$^6$, —SO$_2$(R$^6$), —C(O)N(R$^6$)(R$^7$), —SO$_2$N(R$^6$)(R$^7$); and —P(O)(OR$^6$)(OR$^7$);

R$^{11}$ is selected from the group consisting of alkyl, alkenyl, alkynyl, aryl, heteroaryl, heterocyclyl, halo, haloalkyl, thio, cyano, alkylthio, nitro, —N(R$^8$)(R$^9$), —N(R$^8$)COR$^9$, —N(R$^8$)C(O)OR$^9$, —N(R$^8$)SO$_2$(R$^9$), —CON(R$^8$)(R$^9$), —OC(O)N(R$^8$)—(R$^9$), —SO$_2$N(R$^8$)(R$^9$), —OC(O)OR$^8$, —COOR$^9$, —C(O)N(OH)(R$^8$), —OS(O)$_2$OR$^8$, —S(O)$_2$OR$^8$, —S(O)$_2$R$^8$, —OR$^8$, —COR$^8$, —OP(O)(OR$^8$)(OR$^8$), —P(O)(OR$^8$)(OR$^8$), —N(R$^8$)P(O)(OR$^9$)(OR$^9$) and —[C(R$^4$)$_2$]$_p$—R$^5$;
and —[C(R$^4$)$_2$]$_p$—R$^5$; and
n is 0, 1, 2, or 3;

wherein any one of the aforementioned alkyl, alkenyl, alkynyl, aryl, heteroaryl, heterocyclyl, aralkyl, heteroaralkyl, and heterocyclylalkyl may be optionally substituted.

15. The compound of claim 13, wherein R$^2$ and R$^3$ are joined together to form an optionally substituted heterocyclic ring of the formula:

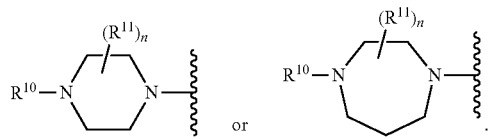

16. The compound of claim 15, wherein n is 0.

17. The compound of claim 15, wherein R$^1$ is hydrogen, alkyl, aryl, heteroaryl, —COR$^6$, —C(O)OR$^6$, or —SO$_2$(R$^6$), or —[C(R$^4$)$_2$]$_p$—R$^5$.

18. The compound of claim 13, wherein R$^2$ and R$^3$ are joined together to form an optionally substituted heterocyclic ring of the formula:

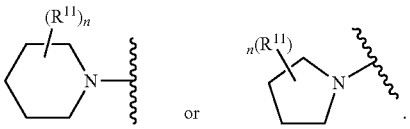

19. The compound of claim 18, wherein n is 0 or 1.

20. The compound of claim 18, wherein R$^{11}$ is alkyl, aryl, heteroaryl, heterocyclyl, —N(R$^8$)(R$^9$), —N(R$^8$)COR$^9$, —N(R$^8$)C(O)OR$^9$, —N(R$^8$)SO$_2$(R$^9$) and —[C(R$^4$)$_2$]$_p$—R$^5$.

21. The compound of claim 19, wherein R$^{11}$ is —[C(R$^4$)$_2$]$_p$—R$^5$, wherein p is 1 or 2, R$^4$ is hydrogen, and R$^5$ is selected from the group consisting of aryl, heteroaryl, heterocyclyl, —N(R$^8$)(R$^9$), —N(R$^8$)COR$^9$, —N(R$^8$)C(O)OR$^9$, and —N(R$^8$)SO$_2$(R$^9$).

22. The compound of claim 11, wherein R$^2$ and R$^3$ are each independently selected from the group consisting of alkyl, alkenyl, alkynyl, aryl, heteroaryl, heterocyclyl, —[C(R$^4$)$_2$]$_p$—R$^5$, —COR$^6$, —C(O)OR$^6$, —SO$_2$(R$^6$), —C(O)N(R$^6$)(R$^7$), and —SO$_2$N(R$^6$)(R$^7$), wherein the alkyl, alkenyl, alkynyl, aryl, heteroaryl, and heterocyclyl may be optionally substituted.

23. The compound of claim 19, wherein R$^2$ is selected from the group consisting of alkyl, alkenyl, alkynyl, aryl, heteroaryl, heterocyclyl, —COR$^6$, —C(O)OR$^6$, —SO$_2$(R$^6$), —C(O)N(R$^6$)(R$^7$), and —SO$_2$N(R$^6$)(R$^7$); and R$^3$ is —[C(R$^4$)$_2$]$_p$—R$^5$.

24. The compound of claim 22, wherein at least one of R$^2$ and R$^3$ is —[C(R$^4$)$_2$]$_p$—R$^5$.

25. The compound of claim 24, wherein R$^4$ is hydrogen.

26. The compound of claim 24, wherein R$^5$ is selected from the group consisting of aryl, heteroaryl, —N(R$^8$)(R$^9$), —N(R$^8$)COR$^9$, —N(R$^8$)C(O)OR$^9$, —N(R$^8$)SO$_2$(R$^9$), —CON(R$^8$)(R$^9$), —OC(O)N(R$^8$)—(R$^9$), —SO$_2$N(R$^8$)(R$^9$), —OC(O)OR$^8$, —COOR$^9$, —C(O)N(OH)(R$^8$), —OS(O)$_2$OR$^8$, —S(O)$_2$OR$^8$, —S(O)$_2$R$^8$, —OR$^8$, —COR$^8$, —OP(O)(OR$^8$)(OR$^8$), —P(O)(OR$^8$)(OR$^8$) and —N(R$^8$)P(O)(OR$^9$)(OR$^9$).

27. A compound, or a pharmaceutically acceptable salt thereof, selected from the group consisting of:
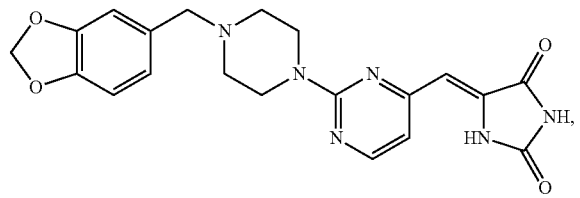
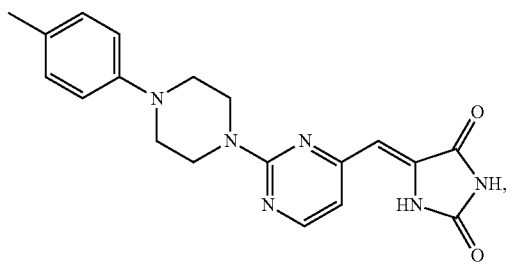
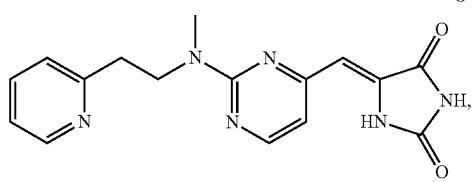
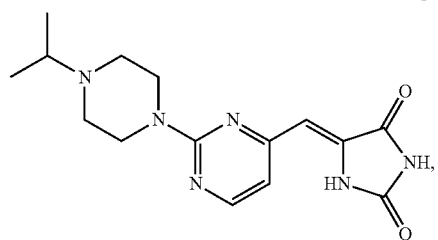
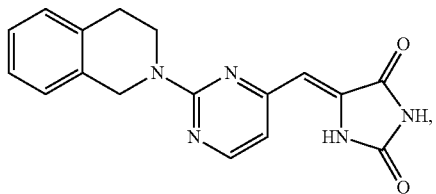
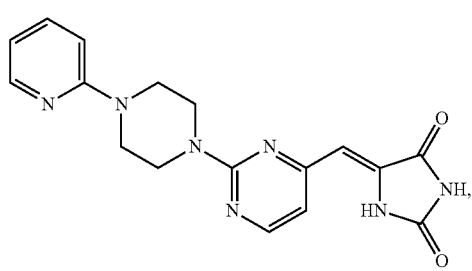
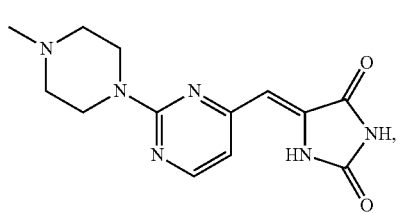
-continued
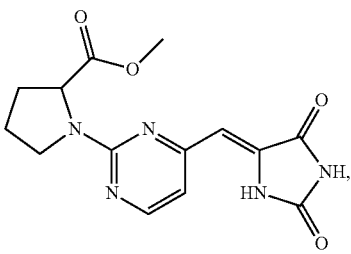
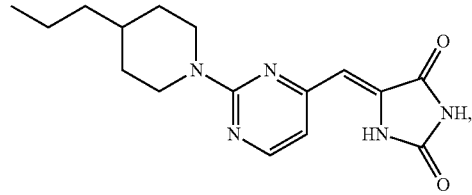
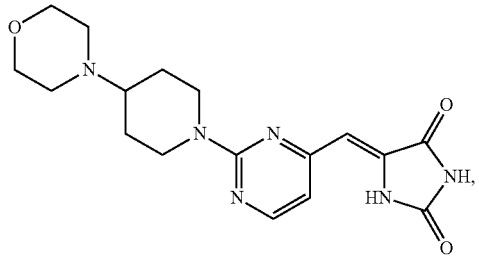
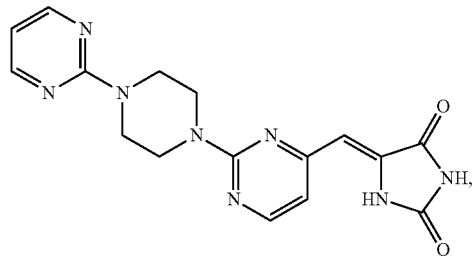
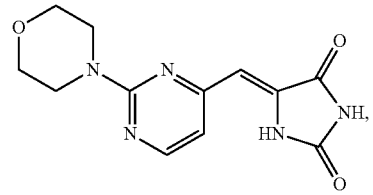
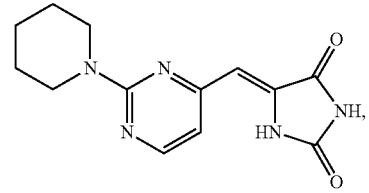
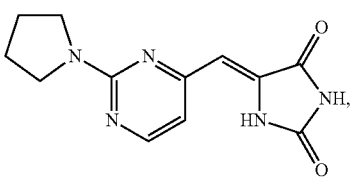

119
-continued
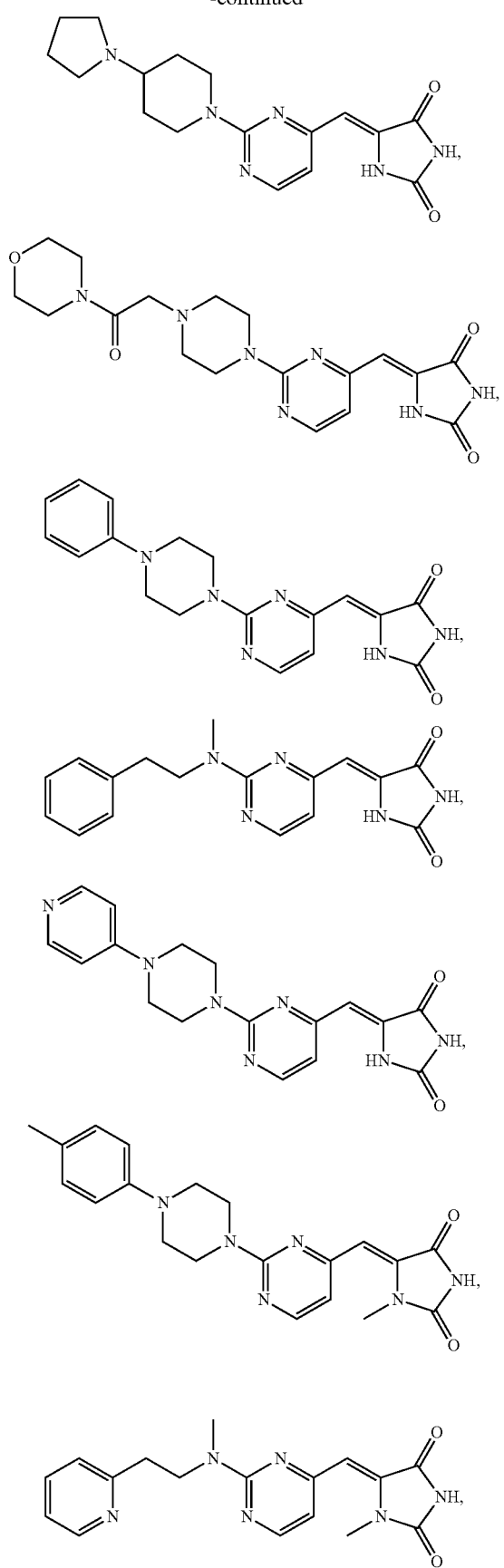
120
-continued
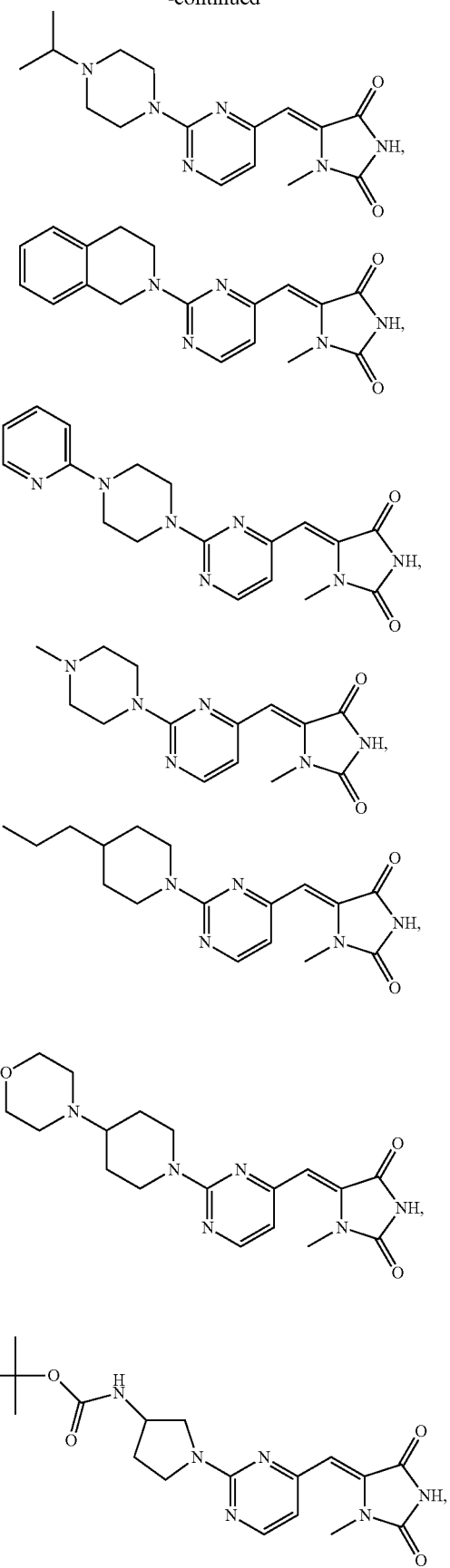

121
-continued
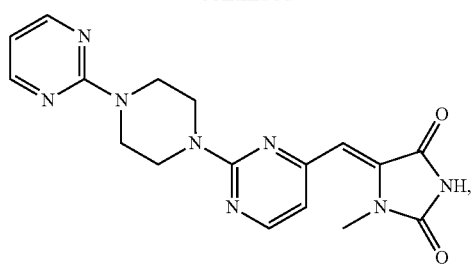
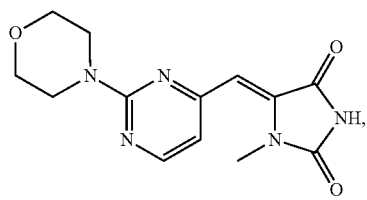
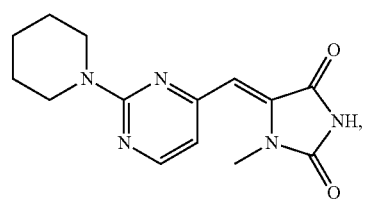
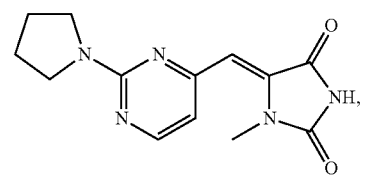
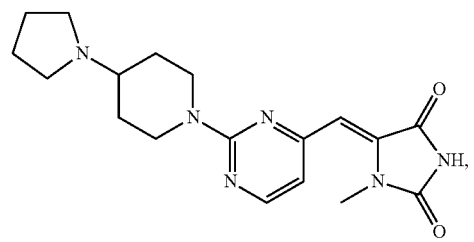
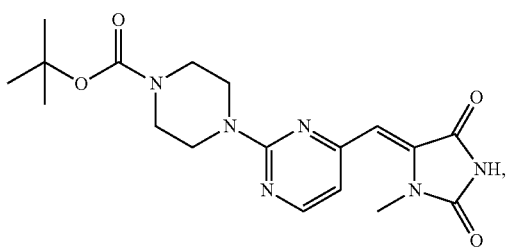
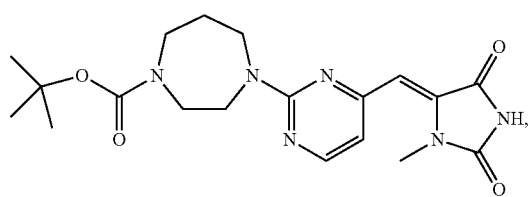
122
-continued
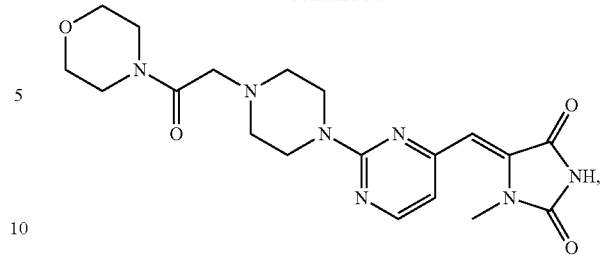
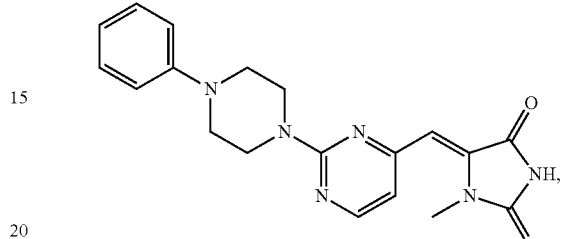
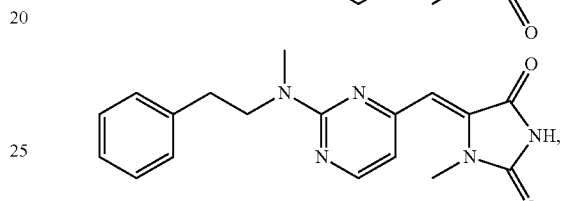
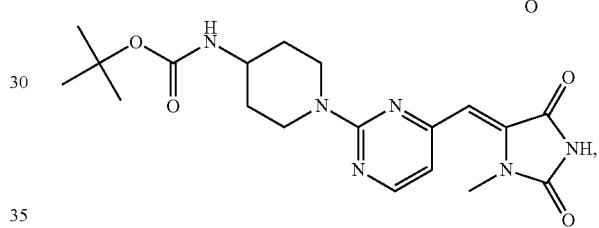
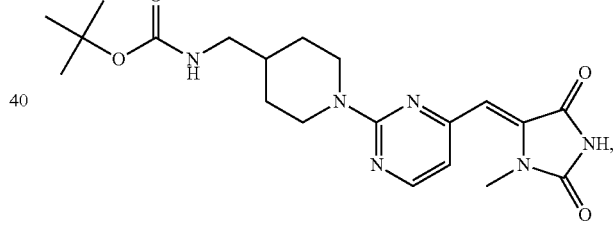
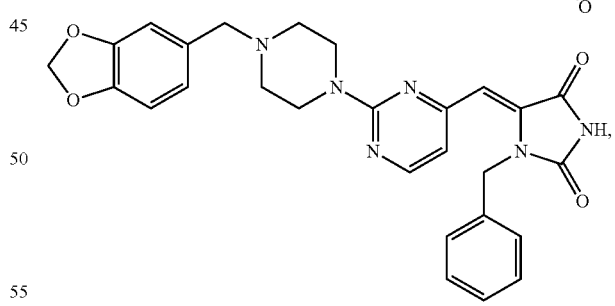
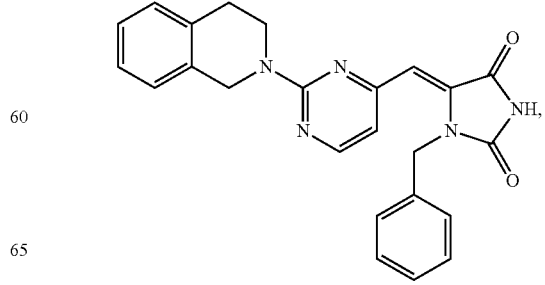

| 123 -continued | 124 -continued |
|---|---|
| 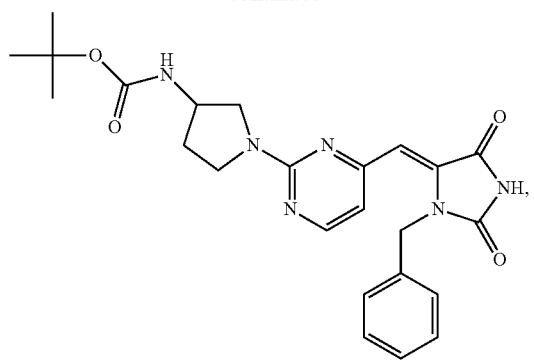 | 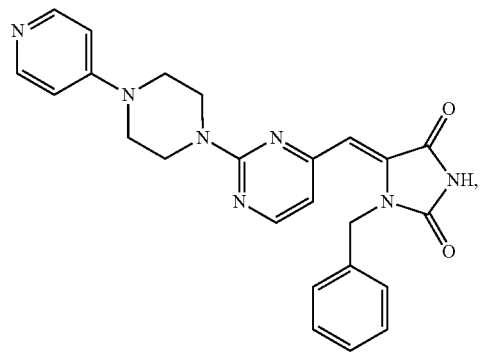 |
| 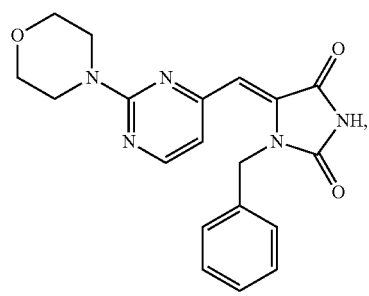 | 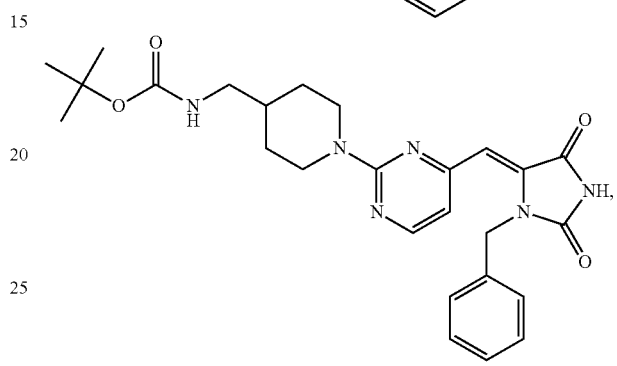 |
| 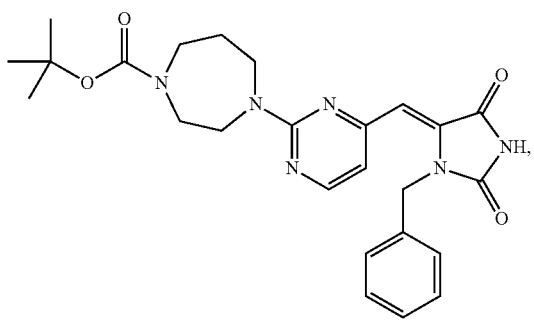 | 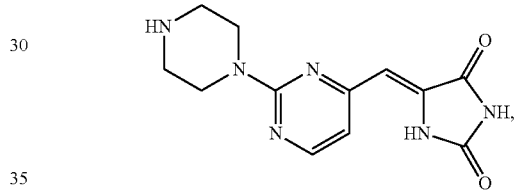 |
| | 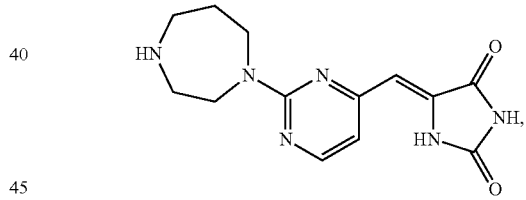 |
| 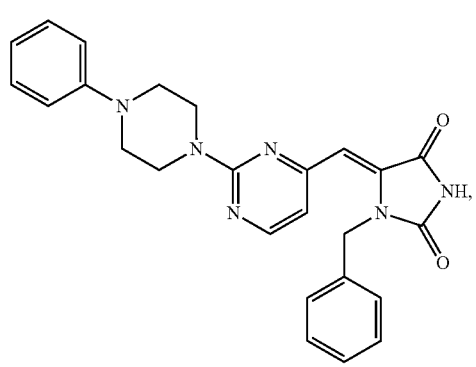 | 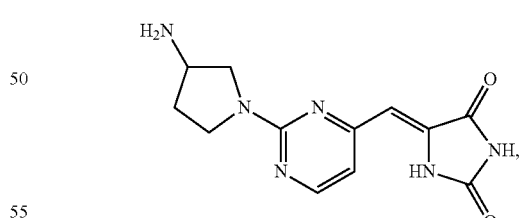 |
| 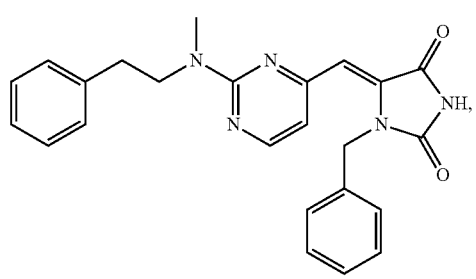 | 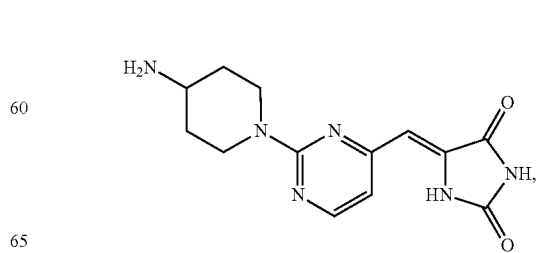 |

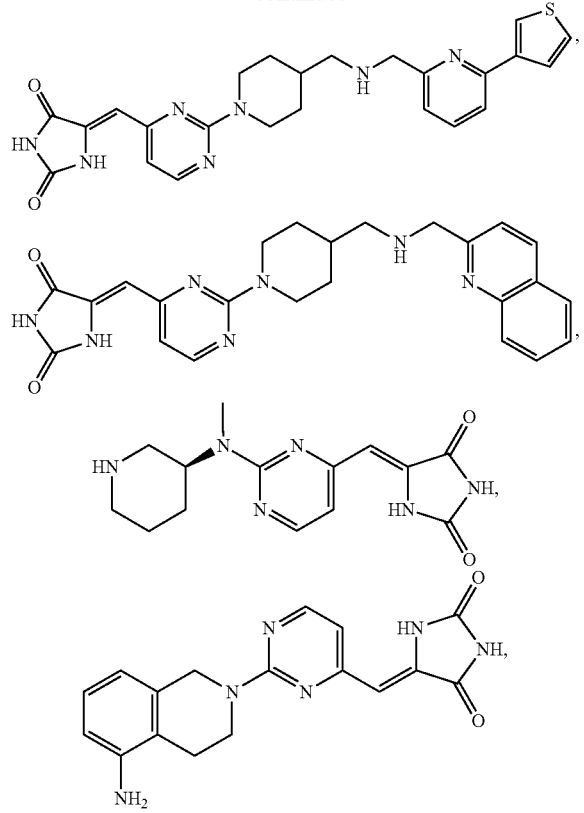
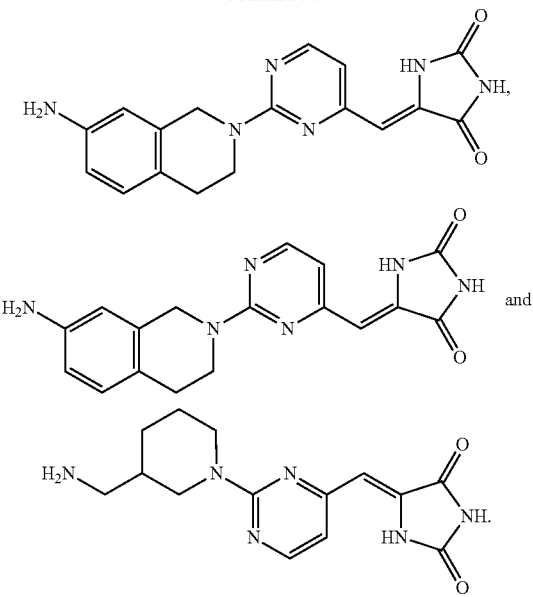
28. A pharmaceutical composition, comprising a compound of claim 1; and a pharmaceutically acceptable excipient.
29. The compound of claim 1, wherein r is 0.
30. The compound of claim 11, wherein $R^{20}$ is hydrogen.
* * * * *